US010603164B2

(12) United States Patent
Girard et al.

(10) Patent No.: US 10,603,164 B2
(45) Date of Patent: Mar. 31, 2020

(54) PROSTHETIC HEART VALVE AND ENDOPROSTHESIS COMPRISING A PROSTHETIC HEART VALVE AND A STENT

(71) Applicant: JenaValve Technology, Inc., Irvine, CA (US)

(72) Inventors: Michael J. Girard, Lino Lakes, MN (US); Randy Lane, Langley (CA); Arnulf Mayer, Markt Schwaben (DE)

(73) Assignee: JenaValve Technology, Inc., Irvine, CA (US)

( * ) Notice: Subject to any disclaimer, the term of this patent is extended or adjusted under 35 U.S.C. 154(b) by 125 days.

(21) Appl. No.: 15/658,955

(22) Filed: Jul. 25, 2017

(65) Prior Publication Data
US 2018/0008405 A1 Jan. 11, 2018

Related U.S. Application Data

(63) Continuation of application No. 13/114,582, filed on May 24, 2011, now Pat. No. 9,744,031.
(Continued)

(30) Foreign Application Priority Data

May 25, 2010 (EP) .................................. 10163831

(51) Int. Cl.
*A61F 2/24* (2006.01)
(52) U.S. Cl.
CPC .......... *A61F 2/2412* (2013.01); *A61F 2/2418* (2013.01); *A61F 2220/0025* (2013.01); *A61F 2220/0075* (2013.01); *A61F 2240/001* (2013.01)
(58) Field of Classification Search
CPC .................. A61F 2/2412; A61F 2/2418; A61F 2002/30317; A61F 2013/00608;
(Continued)

(56) References Cited

U.S. PATENT DOCUMENTS

| 4,922,905 | A | 5/1990 | Strecker |
| 5,002,566 | A | 3/1991 | Carpentier et al. |

(Continued)

FOREIGN PATENT DOCUMENTS

| AU | 2006308187 A1 | 5/2007 |
| AU | 2006310681 A1 | 5/2007 |

(Continued)

OTHER PUBLICATIONS

Aortenklappenbioprothese erfolgreich in der Entwicklung, May 16, 2003 (1 page).

(Continued)

*Primary Examiner* — Paul B Prebilic
(74) *Attorney, Agent, or Firm* — Bookoff McAndrews, PLLC

(57) ABSTRACT

The invention relates to a prosthetic heart valve (100) for an endoprosthesis (1) used in the treatment of a stenotic cardiac valve and/or a cardiac valve insufficiency. The prosthetic heart valve (100) comprises of a plurality of leaflets (102), which consist of a natural and/or synthetic material and have a first opened position for opening the heart chamber and a second closed position for closing the heart chamber, the leaflets (102) being able to switch between their first and second position in response to the blood flow through the heart. In addition, the prosthetic heart valve (100) comprises a leaflet support portion (103), consisting of biological and/or synthetic material for mounting of the prosthetic heart valve (100) to a stent (10), and a bendable transition area (104) which forms a junction between the leaflets (102) and the leaflet support portion (103), the transition area (104) progressing essentially in a U-shaped manner similar to a cusp shape of a natural aortic or pulmonary heart valve for reducing tissue stresses during opening and closing motion of the leaflets (102). The invention further relates to (Continued)

an endoprosthesis (1) comprising a prosthetic heart valve (100) and a stent (10).

12 Claims, 28 Drawing Sheets

Related U.S. Application Data

(60) Provisional application No. 61/348,036, filed on May 25, 2010.

(58) Field of Classification Search
 CPC ...... A61F 2210/0076; A61F 2220/0025; A61F 2220/0075; A61F 2230/0067; A61F 2230/0069; A61F 2250/0017
 See application file for complete search history.

(56) References Cited

U.S. PATENT DOCUMENTS

| | | |
|---|---|---|
| 5,061,277 A | 10/1991 | Carpentier et al. |
| 5,094,661 A | 3/1992 | Levy et al. |
| 5,104,407 A | 4/1992 | Lam et al. |
| 5,197,979 A | 3/1993 | Quintero et al. |
| 5,279,612 A | 1/1994 | Eberhardt |
| 5,332,402 A | 7/1994 | Teitelbaum |
| 5,336,258 A | 8/1994 | Quintero et al. |
| 5,352,240 A | 10/1994 | Ross |
| 5,368,608 A | 11/1994 | Levy et al. |
| 5,411,552 A | 5/1995 | Andersen et al. |
| 5,456,713 A | 10/1995 | Chuter |
| 5,469,868 A | 11/1995 | Reger |
| 5,509,930 A | 4/1996 | Love |
| 5,549,666 A | 8/1996 | Hata et al. |
| 5,595,571 A | 1/1997 | Jaffe et al. |
| 5,613,982 A | 3/1997 | Goldstein |
| 5,632,778 A | 5/1997 | Goldstein |
| 5,674,298 A | 10/1997 | Levy et al. |
| 5,679,112 A | 10/1997 | Levy et al. |
| 5,683,451 A | 11/1997 | Lenker et al. |
| 5,697,972 A | 12/1997 | Kim et al. |
| 5,713,953 A | 2/1998 | Vallana et al. |
| 5,746,775 A | 5/1998 | Levy et al. |
| 5,755,777 A | 5/1998 | Chuter |
| 5,824,041 A | 10/1998 | Lenker et al. |
| 5,824,080 A | 10/1998 | Lamuraglia |
| 5,840,081 A | 11/1998 | Andersen et al. |
| 5,841,382 A | 11/1998 | Walden et al. |
| 5,843,181 A | 12/1998 | Jaffe et al. |
| 5,876,434 A | 3/1999 | Flomenblit et al. |
| 5,880,242 A | 3/1999 | Hu et al. |
| 5,899,936 A | 5/1999 | Goldstein |
| 5,928,281 A | 7/1999 | Huynh et al. |
| 5,935,163 A | 8/1999 | Gabbay |
| 5,104,407 B1 | 9/1999 | Lam et al. |
| 6,001,126 A | 12/1999 | Nguyen-Thien-Nhon |
| 5,061,277 B1 | 2/2000 | Carpentier et al. |
| 6,077,297 A | 6/2000 | Robinson et al. |
| 6,093,530 A | 7/2000 | McIlroy et al. |
| 6,102,944 A | 8/2000 | Huynh et al. |
| 6,117,169 A | 9/2000 | Moe |
| 6,126,685 A | 10/2000 | Lenker et al. |
| 6,168,614 B1 | 1/2001 | Andersen et al. |
| 6,177,514 B1 | 1/2001 | Pathak et al. |
| 6,183,481 B1 | 2/2001 | Lee et al. |
| 6,200,336 B1 | 3/2001 | Pavcnik et al. |
| 6,214,055 B1 | 4/2001 | Simionescu et al. |
| 6,231,602 B1 | 5/2001 | Carpentier et al. |
| 6,254,564 B1 | 7/2001 | Wilk et al. |
| 6,254,636 B1 | 7/2001 | Peredo |
| 6,283,995 B1 | 9/2001 | Moe et al. |
| 6,287,338 B1 | 9/2001 | Sarnowski et al. |
| 6,338,740 B1 | 1/2002 | Carpentier |
| 6,342,070 B1 | 1/2002 | Nguyen-Thien-Nhon |
| 6,344,044 B1 | 2/2002 | Fulkerson et al. |
| 6,350,278 B1 | 2/2002 | Lenker et al. |
| 6,379,740 B1 | 4/2002 | Rinaldi et al. |
| 6,391,538 B1 | 5/2002 | Vyavahare et al. |
| 6,425,916 B1 | 7/2002 | Garrison et al. |
| 6,454,799 B1 | 9/2002 | Schreck |
| 6,461,382 B1 * | 10/2002 | Cao ............... A61F 2/2409 623/2.17 |
| 6,471,723 B1 | 10/2002 | Ashworth et al. |
| 6,478,819 B2 | 11/2002 | Moe |
| 6,508,833 B2 | 1/2003 | Pavcnik et al. |
| 6,509,145 B1 | 1/2003 | Torrianni |
| 6,521,179 B1 | 2/2003 | Girardot et al. |
| 6,540,782 B1 | 4/2003 | Snyders |
| 6,558,417 B2 | 5/2003 | Peredo |
| 6,558,418 B2 | 5/2003 | Carpentier et al. |
| 6,572,642 B2 | 6/2003 | Rinaldi et al. |
| 6,582,462 B1 | 6/2003 | Andersen et al. |
| 6,585,766 B1 | 7/2003 | Huynh et al. |
| 6,613,086 B1 | 9/2003 | Moe et al. |
| 6,682,559 B2 | 1/2004 | Myers et al. |
| 6,719,789 B2 | 4/2004 | Cox |
| 6,730,118 B2 | 5/2004 | Spenser et al. |
| 6,736,845 B2 | 5/2004 | Marquez et al. |
| 6,767,362 B2 | 7/2004 | Schreck |
| 6,790,230 B2 | 9/2004 | Beyersdorf et al. |
| 6,797,000 B2 | 9/2004 | Simpson et al. |
| 6,808,529 B2 | 10/2004 | Fulkerson |
| 6,821,211 B2 | 11/2004 | Otten et al. |
| 6,821,297 B2 | 11/2004 | Snyders |
| 6,824,970 B2 | 11/2004 | Vyavahare et al. |
| 6,830,584 B1 | 12/2004 | Seguin |
| 6,861,211 B2 | 3/2005 | Levy et al. |
| 6,872,226 B2 | 3/2005 | Cali et al. |
| 6,881,199 B2 | 4/2005 | Wilk et al. |
| 6,893,460 B2 | 5/2005 | Spenser et al. |
| 6,908,481 B2 | 6/2005 | Cribier |
| 6,911,043 B2 | 6/2005 | Myers et al. |
| 6,945,997 B2 | 9/2005 | Huynh et al. |
| 6,974,474 B2 | 12/2005 | Pavcnik et al. |
| 7,014,655 B2 | 3/2006 | Barbarash et al. |
| 7,018,406 B2 | 3/2006 | Seguin et al. |
| 7,037,333 B2 | 5/2006 | Myers et al. |
| 7,050,276 B2 | 5/2006 | Nishiyama |
| 7,078,163 B2 | 7/2006 | Torrianni |
| 7,081,132 B2 | 7/2006 | Cook et al. |
| 7,101,396 B2 | 9/2006 | Artof et al. |
| 7,137,184 B2 | 11/2006 | Schreck et al. |
| 7,141,064 B2 | 11/2006 | Scott et al. |
| 7,163,556 B2 | 1/2007 | Xie et al. |
| 7,189,259 B2 | 3/2007 | Simionescu et al. |
| 7,198,646 B2 | 4/2007 | Figulla et al. |
| 7,201,772 B2 | 4/2007 | Schwammenthal et al. |
| 7,238,200 B2 | 7/2007 | Lee et al. |
| 7,252,682 B2 | 8/2007 | Seguin |
| 7,276,084 B2 | 10/2007 | Yang et al. |
| 7,318,278 B2 | 1/2008 | Zhang et al. |
| 7,318,998 B2 | 1/2008 | Goldstein et al. |
| 7,322,932 B2 | 1/2008 | Xie et al. |
| 7,329,278 B2 | 2/2008 | Seguin et al. |
| 7,381,218 B2 | 6/2008 | Schreck |
| 7,393,360 B2 | 7/2008 | Spenser et al. |
| 7,399,315 B2 | 7/2008 | Iobbi |
| 7,452,371 B2 | 11/2008 | Pavcnik et al. |
| 7,473,275 B2 | 1/2009 | Marquez |
| 7,510,575 B2 | 3/2009 | Spenser et al. |
| 7,896,915 B2 | 3/2011 | Guyenot et al. |
| 7,914,569 B2 | 3/2011 | Nguyen et al. |
| 7,914,575 B2 | 3/2011 | Guyenot et al. |
| 7,972,378 B2 | 7/2011 | Tabor et al. |
| 8,398,704 B2 | 3/2013 | Straubinger et al. |
| 8,403,983 B2 | 3/2013 | Quadri et al. |
| 8,465,540 B2 | 6/2013 | Straubinger et al. |
| 8,468,667 B2 | 6/2013 | Straubinger et al. |
| 8,551,160 B2 | 10/2013 | Figulla et al. |
| 8,568,475 B2 | 10/2013 | Nguyen |
| 8,696,743 B2 * | 4/2014 | Holecek ............ A61F 2/2412 623/1.24 |
| 8,778,020 B2 * | 7/2014 | Gregg ............... A61F 2/24 623/2.13 |

(56) References Cited

U.S. PATENT DOCUMENTS

| | | | |
|---|---|---|---|
| 9,717,593 B2* | 8/2017 | Alkhatib | A61F 2/2412 |
| 10,363,134 B2* | 7/2019 | Figulla | A61F 2/24 |
| 2001/0011187 A1 | 8/2001 | Pavcnik et al. | |
| 2001/0039450 A1 | 11/2001 | Pavcnik et al. | |
| 2002/0010489 A1 | 1/2002 | Gayzel et al. | |
| 2002/0032481 A1 | 3/2002 | Gabbay | |
| 2002/0052651 A1* | 5/2002 | Myers | A61F 2/2412 623/2.15 |
| 2002/0055775 A1 | 5/2002 | Carpentier et al. | |
| 2002/0123790 A1 | 9/2002 | White et al. | |
| 2002/0133226 A1 | 9/2002 | Marquez et al. | |
| 2002/0193871 A1 | 12/2002 | Beyersdorf et al. | |
| 2002/0198594 A1 | 12/2002 | Schreck | |
| 2003/0027332 A1 | 2/2003 | Lafrance et al. | |
| 2003/0036791 A1 | 2/2003 | Philipp et al. | |
| 2003/0036795 A1 | 2/2003 | Andersen et al. | |
| 2003/0040792 A1 | 2/2003 | Gabbay | |
| 2003/0050694 A1 | 3/2003 | Yang et al. | |
| 2003/0055495 A1* | 3/2003 | Pease | A61F 2/2418 623/2.11 |
| 2003/0065386 A1 | 4/2003 | Weadock | |
| 2003/0114913 A1 | 6/2003 | Spenser et al. | |
| 2003/0125795 A1 | 7/2003 | Pavcnik et al. | |
| 2003/0139796 A1 | 7/2003 | Sequin et al. | |
| 2003/0139803 A1 | 7/2003 | Sequin et al. | |
| 2003/0149476 A1 | 8/2003 | Damm et al. | |
| 2003/0149478 A1 | 8/2003 | Figulla et al. | |
| 2003/0153974 A1 | 8/2003 | Spenser et al. | |
| 2003/0195620 A1 | 10/2003 | Huynh et al. | |
| 2003/0236570 A1 | 12/2003 | Cook et al. | |
| 2004/0006380 A1 | 1/2004 | Buck et al. | |
| 2004/0039436 A1 | 2/2004 | Spenser et al. | |
| 2004/0049262 A1 | 3/2004 | Obermiller et al. | |
| 2004/0073289 A1 | 4/2004 | Hartley | |
| 2004/0078950 A1 | 4/2004 | Schreck et al. | |
| 2004/0117004 A1 | 6/2004 | Osborne et al. | |
| 2004/0117009 A1 | 6/2004 | Cali et al. | |
| 2004/0148018 A1 | 7/2004 | Carpentier et al. | |
| 2004/0153145 A1 | 8/2004 | Simionescu et al. | |
| 2004/0186558 A1 | 9/2004 | Pavcnik et al. | |
| 2004/0186563 A1* | 9/2004 | Lobbi | A61F 2/2418 623/2.11 |
| 2004/0186565 A1 | 9/2004 | Schreck | |
| 2004/0193244 A1 | 9/2004 | Hartley et al. | |
| 2004/0210301 A1 | 10/2004 | Obermiller et al. | |
| 2004/0210304 A1 | 10/2004 | Seguin et al. | |
| 2004/0260389 A1 | 12/2004 | Case et al. | |
| 2005/0009000 A1 | 1/2005 | Wilhelm et al. | |
| 2005/0033220 A1 | 2/2005 | Wilk et al. | |
| 2005/0033398 A1 | 2/2005 | Seguin | |
| 2005/0043790 A1 | 2/2005 | Seguin | |
| 2005/0049692 A1 | 3/2005 | Numamoto et al. | |
| 2005/0075725 A1 | 4/2005 | Rowe | |
| 2005/0075776 A1 | 4/2005 | Cho | |
| 2005/0096726 A1 | 5/2005 | Sequin et al. | |
| 2005/0096735 A1 | 5/2005 | Hojeibane et al. | |
| 2005/0096736 A1 | 5/2005 | Osse et al. | |
| 2005/0098547 A1 | 5/2005 | Cali et al. | |
| 2005/0113910 A1 | 5/2005 | Paniagua et al. | |
| 2005/0119728 A1 | 6/2005 | Sarac | |
| 2005/0119736 A1 | 6/2005 | Zilla et al. | |
| 2005/0137682 A1 | 6/2005 | Justino | |
| 2005/0137687 A1 | 6/2005 | Salahieh et al. | |
| 2005/0137688 A1 | 6/2005 | Salahieh et al. | |
| 2005/0137690 A1 | 6/2005 | Salahieh et al. | |
| 2005/0137697 A1 | 6/2005 | Salahieh et al. | |
| 2005/0137698 A1 | 6/2005 | Salahieh et al. | |
| 2005/0137702 A1 | 6/2005 | Haug et al. | |
| 2005/0143804 A1 | 6/2005 | Haverkost | |
| 2005/0143807 A1 | 6/2005 | Pavcnik et al. | |
| 2005/0149166 A1 | 7/2005 | Schaeffer et al. | |
| 2005/0150775 A1 | 7/2005 | Zhang et al. | |
| 2005/0171597 A1 | 8/2005 | Boatman et al. | |
| 2005/0171598 A1 | 8/2005 | Schaeffer | |
| 2005/0192665 A1 | 9/2005 | Spenser et al. | |
| 2005/0197695 A1 | 9/2005 | Stacchino et al. | |
| 2005/0222668 A1 | 10/2005 | Schaeffer et al. | |
| 2005/0234546 A1 | 10/2005 | Nugent et al. | |
| 2005/0267560 A1 | 12/2005 | Bates | |
| 2006/0009842 A1 | 1/2006 | Huynh et al. | |
| 2006/0025857 A1 | 2/2006 | Bergheim et al. | |
| 2006/0047343 A1 | 3/2006 | Oviatt et al. | |
| 2006/0058864 A1 | 3/2006 | Schaeffer et al. | |
| 2006/0074484 A1 | 4/2006 | Huber | |
| 2006/0111770 A1 | 5/2006 | Pavcnik et al. | |
| 2006/0142846 A1 | 6/2006 | Pavcnik et al. | |
| 2006/0149360 A1 | 7/2006 | Schwammenthal et al. | |
| 2006/0155366 A1 | 7/2006 | LaDuca et al. | |
| 2006/0167543 A1 | 7/2006 | Bailey et al. | |
| 2006/0178740 A1 | 8/2006 | Stacchino et al. | |
| 2006/0193885 A1 | 8/2006 | Neethling et al. | |
| 2006/0210597 A1 | 9/2006 | Hiles | |
| 2006/0224183 A1 | 10/2006 | Freudenthal | |
| 2006/0229718 A1 | 10/2006 | Marquez | |
| 2006/0229719 A1 | 10/2006 | Marquez et al. | |
| 2006/0246584 A1 | 11/2006 | Covelli | |
| 2006/0259134 A1 | 11/2006 | Schwammenthal et al. | |
| 2006/0259136 A1 | 11/2006 | Nguyen et al. | |
| 2006/0259137 A1 | 11/2006 | Artof et al. | |
| 2006/0265056 A1 | 11/2006 | Nguyen et al. | |
| 2006/0271161 A1 | 11/2006 | Meyer et al. | |
| 2006/0287717 A1 | 12/2006 | Rowe et al. | |
| 2006/0287719 A1 | 12/2006 | Rowe et al. | |
| 2006/0290027 A1 | 12/2006 | O'Connor et al. | |
| 2006/0293745 A1 | 12/2006 | Carpentier et al. | |
| 2007/0005129 A1 | 1/2007 | Damm et al. | |
| 2007/0005131 A1 | 1/2007 | Taylor | |
| 2007/0005132 A1 | 1/2007 | Simionescu et al. | |
| 2007/0010876 A1 | 1/2007 | Salahieh et al. | |
| 2007/0020248 A1 | 1/2007 | Everaerts et al. | |
| 2007/0021826 A1 | 1/2007 | Case et al. | |
| 2007/0027535 A1 | 2/2007 | Purdy, Jr. et al. | |
| 2007/0032856 A1 | 2/2007 | Limon | |
| 2007/0038291 A1 | 2/2007 | Case et al. | |
| 2007/0038295 A1 | 2/2007 | Case et al. | |
| 2007/0043435 A1 | 2/2007 | Seguin et al. | |
| 2007/0050014 A1 | 3/2007 | Johnson | |
| 2007/0088431 A1 | 4/2007 | Bourang et al. | |
| 2007/0093887 A1 | 4/2007 | Case et al. | |
| 2007/0100435 A1 | 5/2007 | Case et al. | |
| 2007/0100440 A1 | 5/2007 | Figulla et al. | |
| 2007/0112422 A1 | 5/2007 | Dehdashtian | |
| 2007/0123700 A1 | 5/2007 | Ueda et al. | |
| 2007/0123979 A1 | 5/2007 | Perier et al. | |
| 2007/0142906 A1 | 6/2007 | Figulla et al. | |
| 2007/0162103 A1 | 7/2007 | Case et al. | |
| 2007/0173932 A1 | 7/2007 | Cali et al. | |
| 2007/0179592 A1 | 8/2007 | Schaeffer | |
| 2007/0185565 A1 | 8/2007 | Schwammenthal et al. | |
| 2007/0203576 A1 | 8/2007 | Lee et al. | |
| 2007/0208550 A1 | 9/2007 | Cali et al. | |
| 2007/0213813 A1 | 9/2007 | Von Segesser et al. | |
| 2007/0233228 A1 | 10/2007 | Eberhardt et al. | |
| 2007/0239271 A1 | 10/2007 | Nguyen | |
| 2007/0244551 A1 | 10/2007 | Stobie | |
| 2007/0260327 A1 | 11/2007 | Case et al. | |
| 2007/0288087 A1 | 12/2007 | Fearnot et al. | |
| 2008/0004688 A1 | 1/2008 | Spenser et al. | |
| 2008/0021546 A1 | 1/2008 | Patz et al. | |
| 2008/0033534 A1 | 2/2008 | Cook et al. | |
| 2008/0065011 A1 | 3/2008 | Marchand et al. | |
| 2008/0071361 A1 | 3/2008 | Tuval et al. | |
| 2008/0071362 A1 | 3/2008 | Tuval et al. | |
| 2008/0071363 A1 | 3/2008 | Tuval et al. | |
| 2008/0071366 A1 | 3/2008 | Tuval et al. | |
| 2008/0071368 A1 | 3/2008 | Tuval et al. | |
| 2008/0071369 A1 | 3/2008 | Tuval et al. | |
| 2008/0077236 A1 | 3/2008 | Letac et al. | |
| 2008/0086205 A1 | 4/2008 | Gordy et al. | |
| 2008/0097586 A1 | 4/2008 | Pavcnik et al. | |
| 2008/0102439 A1 | 5/2008 | Tian et al. | |
| 2008/0133003 A1 | 6/2008 | Seguin et al. | |
| 2008/0140189 A1 | 6/2008 | Nguyen et al. | |
| 2008/0154355 A1 | 6/2008 | Benichou et al. | |

(56) References Cited

U.S. PATENT DOCUMENTS

| | | |
|---|---|---|
| 2008/0200977 A1 | 8/2008 | Paul et al. |
| 2008/0215143 A1 | 9/2008 | Seguin |
| 2008/0255660 A1 | 10/2008 | Guyenot et al. |
| 2008/0255661 A1 | 10/2008 | Straubinger et al. |
| 2008/0262602 A1 | 10/2008 | Wilk et al. |
| 2008/0269878 A1 | 10/2008 | Iobbi |
| 2008/0275549 A1 | 11/2008 | Rowe |
| 2009/0157175 A1 | 6/2009 | Benichou |
| 2009/0216310 A1 | 8/2009 | Straubinger et al. |
| 2009/0216312 A1 | 8/2009 | Straubinger et al. |
| 2009/0216313 A1 | 8/2009 | Straubinger et al. |
| 2009/0222076 A1 | 9/2009 | Figulla et al. |
| 2009/0234443 A1 | 9/2009 | Ottma et al. |
| 2009/0240320 A1 | 9/2009 | Tuval et al. |
| 2009/0259306 A1 | 10/2009 | Rowe |
| 2010/0011564 A1 | 1/2010 | Millwee et al. |
| 2010/0174362 A1 | 7/2010 | Straubinger et al. |
| 2010/0185277 A1 | 7/2010 | Braido et al. |
| 2010/0249915 A1 | 9/2010 | Zhang |
| 2010/0249916 A1 | 9/2010 | Zhang |
| 2010/0249917 A1 | 9/2010 | Zhang |
| 2010/0249918 A1 | 9/2010 | Zhang |
| 2010/0292779 A1 | 11/2010 | Straubinger et al. |
| 2011/0015616 A1 | 1/2011 | Straubinger et al. |
| 2011/0106244 A1 | 5/2011 | Ferrari et al. |
| 2011/0238159 A1 | 9/2011 | Guyenot et al. |
| 2011/0238167 A1 | 9/2011 | Dove et al. |
| 2011/0288626 A1 | 11/2011 | Straubinger et al. |
| 2011/0295363 A1 | 12/2011 | Girard et al. |
| 2013/0079869 A1 | 3/2013 | Straubinger et al. |
| 2013/0144203 A1 | 6/2013 | Wilk et al. |
| 2013/0178930 A1 | 7/2013 | Straubinger et al. |
| 2013/0204359 A1 | 8/2013 | Thubrikar et al. |
| 2013/0253635 A1 | 9/2013 | Straubinger et al. |
| 2014/0058501 A1 | 2/2014 | Bonhoeffer et al. |
| 2016/0354203 A1 | 12/2016 | Tuval et al. |

FOREIGN PATENT DOCUMENTS

| | | |
|---|---|---|
| CA | 2436258 A1 | 1/2005 |
| CA | 2595233 A1 | 7/2006 |
| CA | 2627555 A1 | 5/2007 |
| DE | 19 546 692 A1 | 6/1997 |
| DE | 20 00 3874 U1 | 6/2000 |
| DE | 19 857 887 A1 | 7/2000 |
| DE | 10 010 073 A1 | 9/2001 |
| DE | 10 010 074 A1 | 10/2001 |
| DE | 10 121 210 A1 | 11/2002 |
| DE | 19 546 692 C2 | 11/2002 |
| DE | 10 301 026 A1 | 2/2004 |
| DE | 10 302 447 A1 | 2/2005 |
| DE | 10 010 074 B4 | 4/2005 |
| DE | 19857887 B4 | 5/2005 |
| DE | 10 010 073 B4 | 12/2005 |
| DE | 10 2005 051 849 | 5/2007 |
| DE | 10 2005 052628 A1 | 5/2007 |
| DE | 20 2007 005 491 U1 | 7/2007 |
| EP | 0 084 395 A1 | 7/1983 |
| EP | 0 402 036 B1 | 12/1990 |
| EP | 0 402 176 B1 | 12/1990 |
| EP | 0 458 877 B1 | 4/1991 |
| EP | 0 515 324 A1 | 11/1992 |
| EP | 0 547 135 B1 | 6/1993 |
| EP | 0 592 410 B1 | 11/1995 |
| EP | 0 729 364 B1 | 9/1996 |
| EP | 0 756 498 B1 | 5/1997 |
| EP | 0 778 775 B1 | 6/1997 |
| EP | 0 928 615 A1 | 7/1999 |
| EP | 0 986 348 B1 | 3/2000 |
| EP | 1 041 942 B1 | 10/2000 |
| EP | 1 041 943 B1 | 10/2000 |
| EP | 1 117 446 B1 | 7/2001 |
| EP | 1 206 179 B1 | 5/2002 |
| EP | 1 251 804 B1 | 10/2002 |
| EP | 0 971 649 B1 | 12/2002 |
| EP | 1 281 375 A2 | 2/2003 |
| EP | 1281357 A2 | 2/2003 |
| EP | 1 017 868 B1 | 9/2003 |
| EP | 1354569 A1 | 10/2003 |
| EP | 1 452 153 A1 | 9/2004 |
| EP | 0 987 998 B1 | 10/2004 |
| EP | 1 087 727 B1 | 11/2004 |
| EP | 1 499 366 B1 | 1/2005 |
| EP | 1 253 875 B1 | 4/2005 |
| EP | 1 251 803 B1 | 6/2005 |
| EP | 1 469 797 B1 | 11/2005 |
| EP | 1 690 515 A1 | 8/2006 |
| EP | 1 251 805 B1 | 3/2007 |
| EP | 1 255 510 B1 | 3/2007 |
| EP | 1 112 042 B1 | 11/2007 |
| EP | 1 878 407 A1 | 1/2008 |
| EP | 1 886 649 A2 | 2/2008 |
| EP | 1 900 343 A2 | 3/2008 |
| EP | 1 980 220 A1 | 10/2008 |
| EP | 1 99 4913 A2 | 11/2008 |
| EP | 2 000 115 A2 | 12/2008 |
| FR | 2 828 263 A1 | 2/2003 |
| GB | 2433700 A | 7/2007 |
| GB | 2440809 A | 2/2008 |
| JP | 2003-523262 | 8/2003 |
| JP | 2003-524504 | 8/2003 |
| JP | 2005-118585 | 5/2005 |
| JP | 2007-296375 | 11/2007 |
| WO | WO 90/09102 | 8/1990 |
| WO | WO 95/11055 A1 | 4/1995 |
| WO | WO 95/24873 | 9/1995 |
| WO | WO 95/28183 | 10/1995 |
| WO | WO 96/13227 | 5/1996 |
| WO | WO 97/32615 | 9/1997 |
| WO | WO 98/43556 | 10/1998 |
| WO | WO 98/46165 | 10/1998 |
| WO | WO 99/37337 | 7/1999 |
| WO | WO 99/66863 | 12/1999 |
| WO | WO 00/15148 | 3/2000 |
| WO | WO 00/18445 | 4/2000 |
| WO | WO 2000/25702 A1 | 5/2000 |
| WO | WO 00/47139 A1 | 8/2000 |
| WO | WO 00/53125 | 9/2000 |
| WO | WO 00/62714 | 10/2000 |
| WO | WO 01/10209 A1 | 2/2001 |
| WO | WO 2001/35870 A1 | 5/2001 |
| WO | WO 01/41679 A1 | 6/2001 |
| WO | WO 01/51104 A1 | 7/2001 |
| WO | WO 01/54625 A1 | 8/2001 |
| WO | WO 01/58503 A1 | 8/2001 |
| WO | WO 01/62189 A1 | 8/2001 |
| WO | WO 01/64137 A1 | 9/2001 |
| WO | WO 2002/36048 A1 | 5/2002 |
| WO | WO 02/058745 A1 | 8/2002 |
| WO | WO 02/100301 A1 | 12/2002 |
| WO | WO 02/102286 A1 | 12/2002 |
| WO | WO 03/007795 A2 | 1/2003 |
| WO | WO 2003/003949 A2 | 1/2003 |
| WO | WO 03/009785 A1 | 2/2003 |
| WO | WO 03/013239 | 2/2003 |
| WO | WO 2003/011195 A2 | 2/2003 |
| WO | WO 03/028592 A1 | 4/2003 |
| WO | WO 03/047468 A1 | 6/2003 |
| WO | WO 03/079928 A2 | 10/2003 |
| WO | WO 2003/096935 A1 | 11/2003 |
| WO | WO 2004/004597 A2 | 1/2004 |
| WO | WO 2004/016200 A1 | 2/2004 |
| WO | WO 2004/016201 A2 | 2/2004 |
| WO | WO 2004/019825 A1 | 3/2004 |
| WO | WO 2004/026117 A2 | 4/2004 |
| WO | WO 2004/026173 A2 | 4/2004 |
| WO | WO 2004/028399 A2 | 4/2004 |
| WO | WO 2004/043301 A1 | 5/2004 |
| WO | WO 2004/082527 A2 | 9/2004 |
| WO | WO 2004/082528 A2 | 9/2004 |
| WO | WO 2004/096100 A1 | 11/2004 |

(56) References Cited

FOREIGN PATENT DOCUMENTS

| | | |
|---|---|---|
| WO | WO 2005/021063 A2 | 3/2005 |
| WO | WO 2005/034812 A1 | 4/2005 |
| WO | WO 2005/062980 A2 | 7/2005 |
| WO | WO 2005/072654 A1 | 8/2005 |
| WO | WO 2006/066327 A1 | 6/2006 |
| WO | WO 2006/076890 A1 | 7/2006 |
| WO | WO 2006/102063 A2 | 9/2006 |
| WO | WO 2006/108090 A2 | 10/2006 |
| WO | WO 2006/124649 A2 | 11/2006 |
| WO | WO 2006/127756 A2 | 11/2006 |
| WO | WO 2006/127765 A1 | 11/2006 |
| WO | WO 2006/132948 A1 | 12/2006 |
| WO | WO 2007/047488 A2 | 4/2007 |
| WO | WO 2007/047945 A2 | 4/2007 |
| WO | WO 2007/048529 A1 | 5/2007 |
| WO | WO 2007/051620 A1 | 5/2007 |
| WO | WO 2007/059252 A1 | 5/2007 |
| WO | WO 2007/071436 A2 | 6/2007 |
| WO | WO 2007/098232 A2 | 8/2007 |
| WO | WO 2007/120543 A1 | 10/2007 |
| WO | WO 2008/028569 A1 | 3/2008 |
| WO | WO 2008/035337 A | 3/2008 |
| WO | WO 2008/045949 | 4/2008 |
| WO | WO 2008/070797 A2 | 6/2008 |
| WO | WO 2008/079962 A1 | 7/2008 |
| WO | WO 2008/101083 A2 | 8/2008 |
| WO | WO 2008/125153 A1 | 10/2008 |
| WO | WO 2008/138584 A1 | 11/2008 |
| WO | WO 2008/150529 A | 12/2008 |
| WO | WO 2011/147849 A1 | 12/2011 |

OTHER PUBLICATIONS

English translation of Aortenklappenbioprotheseerfolgreich in der Entwicklung (2 pages), (May 2003).

Screen shots from http://www.fraunhofer.de/presse/filme/2006/index.jsp, 2006 (2 pages).

Liang, Ma, et al., "Double-crowned valved stents for off-pump mitral valve replacement," *Eur. J. Cardio-Thoracic Surgery*, vol. 28, pp. 194-198 (2005) (5 pages).

Huber, Christoph H., et al. "Direct Access Valve Replacement (DAVR)—are we entering a new era in cardiac surgery?" *Eur. J. Cardio-Thoracic Surgery*, vol. 29, pp. 380-385 (2006) (6 pages).

English translation of DE 19 546 692 A1 (4 pages), (Jun. 1997).

English translation of EP 1 469 797 B1 (16 pages), (Nov. 2005).

File history for German Patent DE 19 546 692 filed Dec. 14, 1995 and patented Jul. 11, 2002 (111 pages).

Klein, Allan L. et al., "Age-related Prevalence of Valvular Regurgitation in Normal Subjects: A Comprehensive Color Flow Examination of 118 Volunteers," *J. Am. Soc. Echocardiography*, vol. 3, No. 1, pp. 54-63 (1990) (10 pages).

Gummert, J.F. et al., "Cardiac Surgery in Germany During 2007: A Report on Behalf of the German Society for Thoracic and Cardiovascular Surgery," *Thorac. Cardiov. Surg.*, vol. 56, pp. 328-336 (2008) (9 pages).

Gummert, J.F. et al., "Cardiac Surgery in Germany During 2006: A Report on Behalf of the German Society for Thoracic and Cardiovascular Surgery," *Thorac. Cardiov. Surg.*, vol. 55, pp. 343-350 (2007) (8 pages).

International Search Report for PCT/EP2011/058506, dated Nov. 3, 2011 (3 pages).

\* cited by examiner

PROSTHETIC HEART VALVE AND ENDOPROSTHESIS COMPRISING A PROSTHETIC HEART VALVE AND A STENT

CROSS-REFERENCE TO RELATED APPLICATIONS

This application is a continuation of U.S. application Ser. No. 13/114,582, filed on May 24, 2011, now U.S. Pat. No. 9,744,031, which claims priority to U.S. Provisional Application No. 61/348,036 filed on May 25, 2010 and to EP Application No. 10163831.0 filed on May 25, 2010, the entire disclosures of each of which are incorporated herein by reference.

SUMMARY

The present disclosure relates to a prosthetic heart valve. Specifically, the present disclosure relates to a prosthetic heart valve for a transcatheter delivered endoprosthesis used in the treatment of a stenotic cardiac valve and/or a cardiac valve insufficiency.

The present disclosure also relates to a transcatheter delivered endoprosthesis that includes a prosthetic heart valve and a stent for positioning and anchoring of the prosthetic heart valve at the implantation site in the heart of a patient. Specifically, the present disclosure also relates to a collapsible and expandable prosthesis incorporating a prosthetic heart valve and a stent that can be delivered to the implant site using a catheter for treatment of a stenosis (narrowing) of a cardiac valve and/or a cardiac valve insufficiency.

The expression "narrowing (stenosis) of a cardiac valve and/or cardiac valve insufficiency" may include a functional defect of one or more cardiac valves, which is either genetic or has developed. A cardiac defect of this type might affect each of the four heart valves, although the aortic and mitral valves are affected much more often than the right-sided part of the heart (pulmonary and tricuspid valves). The functional defect can result in narrowing (stenosis), inability to close (insufficiency) or a combination of the two (combined vitium). This disclosure relates to a prosthetic heart valve as well as a transcatheter delivered endoprosthesis that includes a prosthetic heart valve and an expandable stent capable of being implanted transluminally in a patient's body and enlarged radially after being introduced by transcatheter delivery for treating such a heart valve defect.

The human heart has four valves which control the blood flow circulating through the human body. On the left side of the heart are the mitral valve, located between the left atrium and the left ventricle, and the aortic valve, located between the left ventricle and the aorta. Both of these valves direct the oxygenated blood, coming from the lungs into the aorta for distribution through the body. The tricuspid valve, located between the right atrium and the right ventricle, and the pulmonary valve, located between the right ventricle and the pulmonary artery, however, are situated on the right side of the heart and direct deoxygenated blood, coming from the body, to the lungs.

The native heart valves are passive structures that open and close in response to differential pressures induced by the pumping motions of the heart. They consist of moveable leaflets designed to open and close in response to the said differential pressure. Normally, the mitral valve has two leaflets and the tricuspid valve has at least two, preferably three leaflets. The aortic and pulmonary valves, however, have normally at least two, preferably three leaflets, also often referred to as "cusps" because of their half-moon like appearance. In the present disclosure, the terms "leaflet" and "cusps" have the same meaning.

Heart valve diseases are classified into two major categories, named stenosis and insufficiency. In the case of a stenosis, the native heart valve does not open properly, whereby insufficiency represents the opposite effect showing deficient closing properties. Medical conditions like high blood pressure, inflammatory and infectious processes can lead to such cardiac valve dysfunctions. Either way in most cases the native valves have to be treated by surgery. In this regard, treatment can either include reparation of the diseased heart valve with preservation of the patient's own valve or the valve could be replaced by a mechanical or biological substitutes also referred to as prosthetic heart valves. Particularly for aortic heart valves, however, it is frequently necessary to introduce a heart valve replacement.

In principle, there are two possibilities of treating the diseased heart valve, when inserting a prosthetic heart valve: The first way includes extracting at least major parts of the diseased heart valve. The second alternative way provides leaving the diseased heart valve in place and pressing the diseased leaflets aside to create space for the prosthetic heart valve.

Biological or mechanical prosthetic heart valves are typically surgically sewn into the cardiac valve bed through an opening in the chest after removal of the diseased cardiac valve. This operation necessitates the use of a heart-lung machine to maintain the patient's circulation during the procedure and cardiac arrest is induced during implantation of the prosthesis. This is a risky surgical procedure with associated dangers for the patient, as well as a long post-operative treatment and recovery phase. Such an operation can often not be considered with justifiable risk in the case of polypathic patients.

Minimally-invasive forms of treatment have been developed recently which are characterized by allowing the procedure to be performed under local anesthesia. One approach provides for the use of a catheter system to implant a self-expandable stent to which is connected a collapsible heart valve. Such a self-expandable endoprosthesis can be guided via a catheter system to the implantation site within the heart through an inguinal artery or vein. After reaching the implantation site, the stent with the prosthetic heart valve affixed thereto can then be unfolded.

An increasing number of patients suffer from stenosis (narrowing) of cardiac valve and/or cardiac valve insufficiency. In this regard, the issue concerning the provision of long term durability is involved with developing prosthetic heart valves. Each of the four major heart valves open and close about 100,000 times a day and stability requirements for replacements valves are particularly high.

Moreover, there is the danger that—due to the dynamic fluid pressure from blood flow through the prosthetic heart valve, the leaflet material, or the threads (e.g. sutures) used in fastening the prosthetic heart valve to the stent may tear or break. These component failures over the course of time may result in loss of overall valve function.

On the basis of the problems outlined above and other issues with current transcatheter technologies, certain embodiments of the present disclosure address the issue of providing a prosthetic heart valve, as well as a self-expandable endoprosthesis for treating a narrowed cardiac valve or a cardiac valve insufficiency which realizes optimum long term durability, excellent hemodynamics (e.g. low pressure gradients and minimal regurgitation), minimization of paravalvular leakage, accurate device alignment and positioning, no coronary obstruction, prevention of device migration and avoidance of heart block. In addition, the disclosure provides an improved attachment of a prosthetic heart valve to a corresponding collapsible stent structure, thereby distributing stress loads over a greater surface area and thus reducing the potential for stress concentration points throughout the prosthetic heart valve, resulting in improved durability.

In this regard and as it will be described later in detail, the disclosure provides a prosthetic heart valve for a transcatheter delivered endoprosthesis used in the treatment of a stenosis (narrowing) of a cardiac valve and/or a cardiac valve insufficiency. The prosthetic heart valve comprises at least two leaflets, a skirt portion, and a transition area representing a junction between the leaflets and the skirt portion. Each of the at least two leaflets of the prosthetic heart valve consists of natural tissue or synthetic material and has a first opened position for opening the patient's heart chamber and a second closed position for closing the patient's heart chamber, the at least two leaflets being able to switch between their first and second position in response to the blood flow through the patient's heart. The skirt portion consists of natural tissue or synthetic material and is used for mounting of the prosthetic heart valve to a stent. The transition area, which represents a junction between the at least two leaflets of the prosthetic heart valve and the skirt portion, progresses approximately in a U-shaped manner, similar to a cusp shape of a natural aortic or pulmonary heart valve, thereby reducing stresses within the heart valve material during opening and closing motion of the at least two leaflets.

The expression "natural tissue" as used herein means naturally occurring tissue, i.e. biological tissue obtained from the patient, from another human donor, or from a nonhuman animal. On the other hand, the herein used expression "natural tissue" shall also cover tissue fabricated by tissue engineering in the laboratory, for example, from combinations of engineered extracellular matrices ("scaffolds"), cells, and biologically active molecules.

As it will be described in detail later on, in some embodiments of the present disclosure, the prosthetic heart valve either comprises xenografts/homografts or synthetic, non-biological, non-thrombogenic materials. Homografts are either human donor valves, e.g., heart valves, or replacements made of human tissue, e.g., pericardial tissue. In contrast, xenografts describe valves received from animals, e.g., heart valves, or made of animal tissue, e.g., pericardial tissue, typically porcine or bovine respectively. These natural tissues normally contain tissue proteins (i.e., collagen and elastin) acting as a supportive framework and determining the pliability and firmness of the tissue.

It is conceivable to increase the stability of said natural tissues by applying chemical fixation. That is, the natural tissue may be exposed to one or more chemical fixatives (i.e. tanning agents) that form cross-linkages between the polypeptide chains within the protein structures of the natural tissue material. Examples of these chemical fixative agents include: formaldehyde, glutaraldehyde, dialdehyde starch, hexamethylene diisocyanate and certain polyepoxy compounds.

So far, a major problem with the implantation of conventional biological prosthetic heart valves is that the natural tissue material can become calcified, resulting in undesirable stiffening or degradation of the prosthetic heart valve.

Even without calcification, high valve stresses can lead to mechanical failure of components of the heart valve. In order to overcome problems with mechanical failure and potential stress induced calcification that limit valve durability, some embodiments of the disclosure describe an improved construction of the prosthetic heart valve, the design of the disclosed prosthetic heart valve is suited for reducing stresses, and reducing the potential for calcification to improve durability of the heart valve.

In addition, the disclosure provides an improved attachment of a prosthetic heart valve to a corresponding collapsible stent structure, thereby distributing stress loads over a greater surface area and thus reducing the potential for stress concentration points throughout the prosthetic heart valve, resulting in improved durability.

In some embodiment of the disclosure, the prosthetic heart valve may be made of one piece of flat pericardial tissue. This pericardial tissue can either be extracted from an animal's heart (xenograft) or a human's heart (homograft). Subsequently, the extracted tissue may be cut by a laser cutting system, a die press, a water jet cutting system or by hand with a variety of cutting instruments in order to form a pattern representing each of the at least two leaflets or in another embodiment individual leaflets. This pattern may also include the skirt portion in some embodiments. The skirt portion represents an area of the prosthetic heart valve that is used for connecting the prosthetic heart valve to a stent, for example, by means of sutures. Current prosthetic heart valves consist of separated leaflets and skirt portions, wherein the separated leaflets and skirt portions are sewn together by the time the biological heart valve is connected to the stent. According to the "one piece" embodiment described herein, however, the leaflets are integrally formed with the leaflet support portion, that is the prosthetic heart valve is made of one piece of flat pericardial tissue.

The pattern of the prosthetic heart valve, which represents each of the at least two and preferably three leaflets and the skirt portion, shall substantially be constructed like a native aortic or pulmonary heart valve. To this end, the pattern is preferably designed so as to form leaflets in the aforementioned cusp manner, having three half-moon shaped leaflets like the aortic or pulmonary heart valve. The leaflets can be designed in various shapes such as the geometry of an ellipse, U-shape or substantially oval. In this regard, preferably each of the three different leaflets is formed in such a manner that all of them have the same extent; however, it is also conceivable to design them in different sizes.

The shaping of the leaflets into said pattern, for minimizing stresses in the closed position of the prosthetic heart valve, can be achieved in several ways. Most importantly, the mechanical properties of the leaflets of the prosthetic heart valve are influenced by the free margin and the shape of the supported edges. To this end, in an advantageous embodiment disclosed herein, the leaflets are formed into a predetermined 3D shape, by means of a cross-linking the flat tissue on a mandrel. Subsequently, potentially occurring excess material is trimmed off by means of a laser, knife, or water jet respectively to form the edges of the 3D shape. Between the leaflets and the skirt portion, the valve pattern shows a transition area progressing in a substantial U-shaped manner, similar to the cusp shape of a natural aortic or pulmonary heart valve.

In another embodiment of the present disclosure, the lower end section of the prosthetic heart valve exhibits a tapered or flared shape. Such a tapered or flared shape may be advantageous regarding the attachment of the prosthetic heart valve to a corresponding stent. As will be explained in more detail hereinafter, a corresponding stent may comprise a tapered or flared lower end section in order to improve the anchoring of the stent at the implantation site. As a consequence, it may be useful to construct the lower end section of the prosthetic heart valve in a tapered or flared shape, so as to prevent paravalvular leakage between the stent and the blood vessel.

According to another embodiment of the present disclosure, the leaflets may have a cuspidal geometry, which is formed in an elliptically, u-shaped or oval manner. Such a cuspdial geometry reduces the potential for stress concentrations and therefore minimizes the potential for areas of wear and calcium deposition. In another embodiment of the present disclosure all three leaflets are shaped to the same extent, absorbing loads equally throughout the cardiac cycle. However, it is conceivable to assemble a device with leaflets of varying designs.

With reference to another embodiment of the present disclosure, the leaflet portion of the prosthetic heart valve is designed to provide redundant coaptation for potential annular distortion. In particular, redundant coaptation means that each of the leaflets covers more than one third of the inner diameter of the respective stent, in the closed position of the valve. The redundant coaptation may reduce stress on the leaflets and provides reliable closure of the heart chamber in the second closed position of the leaflets, even in the case of an annular distortion. That is, the prosthetic heart valve of the present disclosure is capable of preventing regurgitation even if the size of the heart valve annulus has been altered (annular distortion).

In another embodiment of the present disclosure, the prosthetic heart valve comprises a plurality of fastening holes provided along the progression of the bendable transition area. These fastening holes are preferably introduced into the tissue of the prosthetic heart valve before the valve is attached to the corresponding stent. This plurality of fastening holes may reduce the time needed for attachment of the prosthetic heart valve to the retaining arches of the corresponding stent.

According to another aspect of the present disclosure, the prosthetic heart valve is designed for collapsing and delivering in a catheter. To this end, the prosthetic heart valve can be designed in such a way as to fit inside the corresponding stent structure. Furthermore, it is conceivable that the design of the prosthetic heart valve comprises certain folds in order to allow for collapsing to very small diameters.

In another embodiment of the invention, the tissue material of the prosthetic heart valve has a thickness of 160 µm to 300 µm, preferably from 220 µm to 260 µm. However, it should be noted that the thickness may be dependent on the tissue material of the prosthetic heart valve. In general, the thickness of bovine tissue is thicker than the thickness of porcine tissue.

The blood vessels and heart valve orifices of the individual patients can have significantly varying diameter, accordingly, the prosthetic heart valve may have a diameter ranging form 19 mm to 28 mm. Thus, the prosthetic heart valve of the present disclosure is adapted to fit to the individual characteristics of individual patient's heart anatomy.

In another embodiment of the present disclosure, the bendable transition area of the prosthetic heart valve is attached to retaining arches of the stent by means of sutures, having a diameter larger than the diameter of the sutures used for attachment of the prosthetic heart valve to an annular collar of the stent. Due to this, the prosthetic heart valve can be reliably attached to the stent without adding too much bulk to the stent, in order to collapse the endoprosthesis to a small diameter.

The disclosure also provides a transcatheter delivered endoprosthesis having a prosthetic heart valve affixed to a stent. The stent provides retaining arches which are configured once in the expanded state to be in a gradually uniform U-shape. The transition area of the tissue is attached to the retaining arches of the stent in a number of possible embodiments. The purpose of the retaining arches is to control the motion of the leaflets during the opening and closing phases of the valve in a manner which minimizes the stresses associated with the cyclic motion.

In general, current transcatheter prosthetic heart valves consist of separated leaflets and skirt portions, wherein the separated leaflets and skirt portions are sewn together by the time the biological heart valve is connected to the stent. Hence, with the conventional prosthetic heart valves, additional suture lines are necessary, causing stress concentration and reduced flexibility of the heart valve, thus leading to earlier calcification of the prosthetic heart valves.

In order to reduce or minimize stress concentration and to enhance flexibility of the heart valve, in some embodiments as disclosed herein the leaflets are integrally formed with the skirt portion. For example, a single piece of pericardium may be used for forming the prosthetic heart valve. As an alternative, the skirt portion may consist of multiple pieces of tissue, e.g. three pieces of tissue, which are sewn together by the time the biological heart valve is connected to the stent, wherein the leaflets are integrally formed with the tissue material of the pieces which together form the skirt portion. For example, three individual tissue panels may be utilized to construct the valve portion of the prosthetic heart valve. Whether a single piece of pericardium or three panels are used, the tissue structure is sutured to the stent structure to create the desired U-shape of the leaflets. This U-shape helps distribute the load on the leaflets throughout the cardiac cycle, but especially when in the closed position.

By avoiding that the leaflets must be sewn to the skirt portion(s), greater strength and durability of the heart valve assembly may be provided, as the strength and integrity of a uniform piece of tissue is improved from separate pieces of tissue sewn together. Additionally, the advantages of not having a seam include reduced assembly time (less suturing), less overall bulk when collapsing the prosthesis for small catheter delivery and more flexible leaflets at the transition area that could improve leaflet motion and hemodynamics.

The natural tissue material used for the manufacture of prosthetic heart valves typically contains connective tissue proteins (i.e., collagen and elastin) that act as supportive framework of the tissue material. In order to strengthen this compound of tissue proteins, a chemical fixation process may be performed, linking the proteins together. This technique usually involves the exposure of the natural tissue material to one or more chemical fixatives that form the cross-linkages between the polypeptide chains of the collagen molecules. In this regard, it is conceivable to apply different cross-linking techniques for different parts of the prosthetic heart valve tissue. For instance, the leaflets of the prosthetic heart valve could be treated by a different chemical fixative agent than the skirt portion in order to obtain diverse rigidity within the prosthetic heart valve.

In addition, it is conceivable to have leaflets and a skirt which are not integral. In this case, different cross-linking techniques may be applied to the leaflets and the skirt.

Examples of chemical fixative agents conceivably used for cross-linking of the prosthetic heart valve, according to the present disclosure include: aldehydes, (e.g. formaldehyde, glutaraldehyde, dialdehyde starch, para formaldehyde, glyceroaldehyde, glyoxal acetaldehyde, acrolein), diisocyanates (e.g., hexamethylene diisocyanate), carbodiimides, photooxidation, and certain polyepoxy compounds (e.g., Denacol-810, -512).

According to some of the disclosed embodiments, the prosthetic heart valve is mounted to the inner surface of a support stent. This arrangement facilitates protection of the prosthetic heart valve material during collapse and deployment. This is because the prosthetic heart valve is not in contact with the inner wall of the implantation catheter, and thus may not get stuck on the inner surface thereof. On this account, damage to the prosthetic heart valve is avoided. Also, such an endoprosthesis can be collapsed to a smaller diameter compared with a prosthetic heart valve mounted to the outer surface of the stent, hence providing the possibility to use smaller catheters.

On the other hand, it is conceivable to mount the prosthetic heart valve to the outer surface of a support stent. That is, the skirt portion could be in direct contact with the diseased native heart valve and could be attached to the stent by means of sutures. Mounting the prosthetic heart valve to the outer surface of the stent supports the load transfer from the leaflet to the stent. This greatly reduces stresses on the leaflets during closing and consequently improves the durability thereof. Also, it is possible to design the valve to obtain improved hemodynamics in the case of mounting the skirt portion and commissures to the outer surface of the stent. Additionally, the heart valve material which is in direct contact with the diseased native heart valve provides a good interface for sealing against leakage (i.e., paravalvular leakage), tissue in-growth and attachment. The stent designs for this endoprosthesis uniquely accommodate this valve embodiment and advantages, whereas for cage-like transcatheter delivered stent designs this is not possible.

The prosthetic heart valve can be made from pericardial tissue, for example, human pericardial tissue, preferably animal pericardial tissue, whereby bovine or porcine pericardial tissue is preferred. However, it is conceivable to employ kangaroo, ostrich, whale or any other suitable xeno- or homograft tissue of any feasible dimension.

Preferably, porcine tissue thicknesses of 220 to 260 μm after fixation shall be used to manufacture the biological prosthetic heart valves. Of course, this example is not a limitation of the possible kinds of tissues and their dimensions. Rather, it is conceivable to employ kangaroo, ostrich, whale or any other suitable xeno- or homograft tissue of any feasible dimension.

Many aspects of the disclosed prosthetic heart valve embodiments may become clear considering the structure of a corresponding stent to which the prosthetic heart valve may be attached in order to form a transcatheter delivered endoprosthesis used in the treatment of a stenosis (narrowing) of a cardiac valve and/or a cardiac valve insufficiency.

According to an aspect of the disclosure, a stent suitable for implantation with the aforementioned prosthetic heart valve may comprise positioning arches configured to be positioned within the pockets of the patient's native heart valve. Furthermore, the stent may comprise retaining arches. In detail, for each positioning arch one retaining arch may be provided. In the implanted state of the stent, the respective head portions of the positioning arches are positioned within the pockets of the patient's native heart valve such that the positioning arches are located on a first side of a plurality of native heart valve leaflets. On the other hand, in the implanted state of the stent, the retaining arches of the stent are located on a second side of the native heart valve leaflets opposite the first side. In this respect, the positioning arches on the one hand and the retaining arches on the other hand clamp the native heart valve leaflets in a paper-clip manner.

Hence, the positioning arches of the stent are designed to engage in the pockets of the native (diseased) cardiac valve which allows accurate positioning of the stent and a prosthetic heart valve affixed to the stent. Furthermore, in the implanted state, each positioning arch co-operates with a corresponding retaining arch resulting in clipping of the native leaflet between the two arches. In this way, the positioning and retaining arches hold the stent in position and substantially eliminate axial rotation of the stent In a preferred embodiment, the positioning arch may be formed such as to have a substantially convex shape. In this way, the shape of each positioning arch provides an additional clipping force against the native valve leaflet.

The at least one retaining arch of the stent may be connected to a corresponding positioning arch by a connecting web. The retaining arch may extend substantially parallel to the positioning arch, thus having essentially the same shape. The shape of the retaining arch basically represents a U-shape with a small gap at its lower end. This gap is surrounded by a connection portion which originates during the fabrication of the tip of the positioning arches. The connection portion may be similar to a U- or V-shape and links the two sides of a retaining arch.

Along the retaining arches of the stent, a plurality of fastening holes and optionally one or more notches may be provided. Preferably, these fastening holes and notches are longitudinally distributed at given positions along the retaining arches and guide at least one thread or thin wire to fasten the tissue components of the prosthetic heart valve to the stent, thereby enabling a precise positioning of the tissue components on the stent. The means provided for fastening the tissue components of the biological prosthetic heart valve to the retaining arches of the stent (thread or thin wire) is guided by way of the fastening holes and notches to ensure accurate repeatable securement of the bioprosthetic heart valve within the stent structure. This accurate securement of the biological prosthesis substantially reduces the potential for longitudinal displacement of the biological prosthetic heart valve relative to the stent.

According to another embodiment of the present disclosure, the aforementioned plurality of retaining arches are provided with one or more fastening notches which can be used to fix the bendable transition area to the stent. To this end, the retaining arches may be segmented by a plurality of bending edges forming said fastening notches and defining bending points of the retaining arches. The fastening notches simplify the attachment of the bendable transition area of the prosthetic heart valve to the retaining arches.

In another aspect of the stent which is suitable for implantation with a biological prosthetic heart valve as disclosed herein, the retaining arches are cut from the material portion of a small metal tube in an shape that when expanded essentially form the U-shaped structure corresponding to the aforementioned progression of the transition area.

At the lower end of the stent, an annular collar may be provided. The annular collar may serve as a supporting body through which the radial forces, developing due to the self-expansion, are transmitted to the vascular wall. Attached to the annular collar is the skirt portion of the biological prosthetic heart valve. Typically, this attachment is implemented by means of suturing.

The intent of the self expanding annular collar in combination with the attached skirt region of the valve is to provide sufficient radial forces so as to seal and prevent paravalvular leakage. In addition, the collar aids in anchoring the prosthesis in the annulus to prevent migration. This collar may incorporate a flared or tapered structure to further enhance securement.

As mentioned above, a prosthetic heart valve can be attached to a corresponding stent in order to provide a transcatheter delivered endoprosthesis which can be used in the treatment of a stenosis (narrowing) of a cardiac valve and/or a cardiac valve insufficiency.

A prosthetic heart valve made from pericardial tissue material may be attached to the retaining arches and annular collar of the afore-mentioned stent by means of braided multi-filament polyester sutures. These sutures may have any suitable diameter, typically about 0.07 mm.

In order to increase the strength of the connection of biological prosthetic heart valve to the stent, however, it is conceivable to increase the size of the multi-filament sutures, for example, up to 0.2 mm. In this way, it is possible that the fundamental bond between the transition area of the prosthetic heart valve and the retaining arches of the stent exhibits additional stability. On the other hand, the remaining sutures shall be kept as thin as possible to enable collapsing of the endoprosthesis to a small diameter.

A common running stitch pattern may be used to obtain said bonding. According to the disclosure, the stitch pattern is preferably a locking stitch or a blanket stitch respectively. Of course, any other suitable stitch pattern (i.e. overlocking stitch, slipstitch or topstitch) is also possible.

Considering the stress concentration due to direct stitching in the heart valve material, another aspect of the disclosure may provide that the material of the prosthetic heart valve is reinforced to improve its suture retention force. To this end, laser cut suturing holes may be introduced into the prosthetic heart valve tissue with the laser cutting process strengthening the tissue area around the cut hole. Predefined laser cutting holes might also ease the suturing process itself and reduce stresses on the material of the prosthetic heart valve due to the penetration of the needle during stitching.

In another embodiment of the present disclosure, the connection of the prosthetic heart valve material to a stent may be reinforced by means of reinforcement elements. Such reinforcement elements are intended to reduce stress concentrations in the material of the prosthetic heart valve that may occur from direct stitching in the valve material. In particular, the reinforcement elements might reduce stress concentration in the tissue material of the prosthetic heart valve at the connection between the bendable transition area and the retaining arches of the stent. The reinforcement elements may be placed between an inner suture and the prosthetic heart valve material, thus distributing aforementioned stresses, caused by the stitching, over a larger area of the valve material. These reinforcement elements can be used at discrete locations or continuously along the path of the stitching. For example, they can be placed opposite to the retaining arches of the stent on the other side of the prosthetic heart valve material.

Reinforcement elements may be applied in order to avoid direct contact between knots of the sutures and the tissue of the prosthetic heart valve, thereby reducing abrasion of the prosthetic heart valve tissue due to rubbing against said sutures. To reduce direct contact between the heart valve tissue and the stent structure or any other metallic component of the endoprosthesis, reinforcement elements can further be used to prevent the tissue of the prosthetic heart valve from directly contacting the stent structure or any other metallic component respectively.

In this regard, it is also conceivable to locate reinforcement elements along the entire surface of the prosthetic heart valve. Preferably, such reinforcement elements could also be located at or near the upper edge of the leaflets. These upper edges, building the commissures of the endoprosthesis, are exposed to an increased tension, which are more likely to tear during the operation of the prosthetic heart valve.

Moreover, it is also feasible to place said reinforcement elements inside the tissue of the prosthetic heart valve, instead of a mere attachment on the surface of the prosthetic heart valve. In this regard, it may be advantageous to have a layer of tissue or synthetic material of different mechanical properties inside the aforementioned prosthetic heart valve. This alternative embodiment may be especially useful in order to reinforce the leaflets of the prosthetic heart valve in order to increase their ability to yield mechanical stresses occurring during the operation of the endoprosthesis.

Reinforcement elements can be used at discrete locations or continuously along the path of the stitching. For example, they can be placed opposite to the retaining arches of the stent on the other side of the prosthetic heart valve material.

The reinforcement elements may be folded or formed in such a way that round edges are formed. These round edges are designed to reduce or avoid abrasion of the valve material during opening and closing of the prosthetic heart valve.

With regard to a further embodiment of the present disclosure, the reinforcement elements comprise at least one inner cushion, which is mounted to the inner surface of the bendable transition area of the prosthetic heart valve. This inner cushion is arranged essentially opposite the retaining arches and/or to the commissure attachment region of the stent. Opposite in this context means that the inner cushion is mounted on an opposite side of the prosthetic heart valve. The inner cushion is designed to reduce the stress concentrations in the tissue that occur from direct stitching in the tissue. In more detail, the inner cushion prevents the prosthetic heart valve tissue from directly contacting knots of the suture. Due to this, wear of the heart valve tissue is reduced, as said knots do not rub on the surface of the tissue, during opening and closing of the heart valve.

In a further embodiment, the at least one inner cushion may be a pledget made of one or multiple layer materials. The inner cushion may consist of materials, for examples, like polyester velour, PTFE, pericardial tissue or any other material suitable for forming round edges, distributing or buffering stresses in the valve material, due to the sutures. On this account, the material of the inner cushion can be made from flat sheets or fabrics such as knits or woven constructions. It is to be noted that the reinforcement elements can be applied in order to span between stent struts, in particular across a gap, located at the lower end of the retaining arches, to help support the valve material across said gap.

In an alternative implementation, the reinforcement elements may consist of a wire rail placed at the inner surface of the bendable transition area of the prosthetic heart valve, essentially opposite the retaining arch of the stent. The wire rail may be secured in place using a stitch pattern meant to accommodate the wire rail and the valve material to the stent. In comparison to the inner cushion mentioned above, such a wire rail could be easier to attach to the material of the prosthetic heart valve. Furthermore the already rounded shape of the rail does not require the wire rail to be folded in order to obtain rounded edges for prevention of valve material abrasion.

It is preferable that said wire rail is made of Nitinol in order to allow collapsing of the reinforcement element simultaneously with the stent structure.

Moreover, in another realisation, the reinforcement elements may be essentially of the same size and form as the retaining arches of the stent, hence forming an inner attachment rail. The reinforcement elements, however, shall be of thinner material than the retaining arches. This is due to the fact that thick material may limit the ability of the endoprosthesis to be collapsed to a small size.

In particular, the inner attachment rail may have the same fastening holes and notches longitudinally distributed at given locations as the retaining arches of the stent. Again, the attachment rail may be placed on the inner surface of the bendable transition area of the prosthetic heart valve, opposite to the retaining arches of the stent. Thus, the material of the prosthetic heart valve may be clamped in between the stent and the reinforcement element, which are connected through sutures. The reinforcement element thus may act as an inner attachment rail for the leaflets of the prosthetic heart valve to bend over and evenly distribute stress loads affecting the valve material over a large attachment rail rather than individual suture points.

Although most embodiments of the disclosure use sutures to fix the reinforcement element or valve material to the stent, it is conceivable to use different attachment methods like welding, soldering, locking fixture and rivets. For instance, these methods could be used to attach the aforementioned inner attachment rail to the retaining arches of the stent. This would result in clamping the prosthetic heart valve material in between the inner surface of the stent and the outer surface of the reinforcement element without penetrating the valve material with needles of suture.

Another alternative attachment concept includes a reinforcing element attached to the back side of the prosthetic heart valve material. This concept may be suitable for attachment in a high stress area of a commissure attachment region on top of the retaining arches, which is described in more detail below. This concept involves creating a strengthened region by folding the prosthetic heart valve material and wrapping it with the reinforcing element. Thus, the reinforcement element forms an outer wrapping element which is mounted to the outer surface of the bendable transition area of the prosthetic heart valve, at the commissure attachment region of the stent. The reinforced bendable transition area of the prosthetic heart valve can then be securely attached to the retaining arches of the stent or the commissure attachment region of the stent.

The aforementioned outer wrapping element of the reinforcing element is preferably made of a polymer material such as PTFE or a PET fabric or sheet. However, it could also be a more rigid U-shaped clip or bendable material that can pinch the folded valve material. One advantage this concept has over the other reinforcing elements is that the reinforcing material is not placed on the inner surface of the prosthetic heart valve, hence does not disrupt the blood flow or potentially be a site for thrombus formation.

The outer wrapping element of the reinforcing element may also provide an opening buffer to keep the valve leaflet material from opening too wide and hitting the stent, which would cause wear of the valve material. Similar to the rounded edges of the other reinforcement elements, these buffers should be rounded, smooth or soft to avoid wear when the open valve material hits them. The buffer should be small enough to not significantly over restrict leaflet material opening.

An especially beneficial embodiment of the present invention includes an attachment concept with reinforcement elements attached to the inner surface and to the outer surface of the transition area of the prosthetic heart valve. This configuration optimally prevents stress concentration and resulting wear of the prosthetic heart valve.

In particular, a first reinforcement element is connected to the outer surface of the bendable area of the prosthetic heart valve, preferably lining the retaining arches and the commissure attachment region over their entire length. The said reinforcement element, which is connected to the outer surface of the prosthetic heart valve, can be made of animal pericardial tissue, such as the one used for the prosthetic heart valve itself. Of course, it is conceivable to use any other suitable material for the reinforcement element, such as synthetic materials or even homograft (human) tissue. The reinforcement element, connected to the outer surface of the prosthetic heart valve, has several advantages, such as preventing any rubbing and wear between the leaflet and the stent at the retaining arches or commissure attachment region respectively. Even if the attachment is tightly sutured, the tissue will have strain cycles at the surface during opening and closing motion of the leaflets, which can cause wear against the stent from micro movements. Furthermore, the reinforcement element allows for an additional spring-like compression to tighten the attachment of the leaflet to the stent, providing a more durable attachment than the one achieved by suturing the leaflets to a rigid surface. Also, the reinforcement element serves as a bumper during opening to limit full opening and reduce the accompanied shock affecting the prosthetic heart valve at opening.

In another embodiment, the reinforcement element, which is connected to the outer surface of the prosthetic heart valve, extends along the retaining arches and along the commissure attachment region, having a wider surface than the surface of the retaining arches or the surface of the commissure attachment region respectively. For this reason, the reinforcement element provides a surface, sufficient to cover the retaining arches and the commissure attachment region completely. Thus, abrasion or wear of the tissue at the retaining arches or commissure attachment region respectively is avoided reliably.

Concerning the attachment of the aforementioned reinforcement element another advantageous embodiment includes wrapping the reinforcement element around the retaining arches and the commissure attachment region and securing this connection by means of wrapping and stitching. That is to say that the reinforcement element is secured firmly to the retaining arches or commissure attachment region respectively, providing a stable surface for attachment of the prosthetic heart valve.

With regard to the reinforcement element, which is connected to the inner surface of the transition area of the prosthetic heart valve, in another realisation, the reinforcement element consists of a folded strip of porcine pericardium and is attached to the transition area and stent by means of sutures. This folded strip of porcine pericardium allows the sutures to spread out the compressive forces that secure the leaflet tissue. A tight suture attachment is required to avoid any movement or slipping under physiological loads. If attached tightly, the loads from the leaflet will be at least partially transferred to the stent through friction and not directly to the sutures at the needle holes. This minimizes the stress concentration by spreading out the stresses, especially at the commissure attachment region. Also, the strip of porcine pericardium serves as a bumper to absorb the impact of the tissue during closing and reduces the dynamic stresses transferred to the sutures. Of course, it is conceivable to use different materials to implement the reinforcement element, which is connected to the inner surface of the prosthetic heart valve, such as wires, brackets, synthetic materials or even homograft (human) tissue. In order to reduce or prevent leakage during closed state of the prosthetic heart valve, however, the aforementioned reinforcement element has to be constructed with a minimal size, so as to avoid the formation of a gap in between the closed leaflets.

According to another embodiment of the present invention, the reinforcement elements are wrapped in tissue to avoid wear of the prosthetic heart valve tissue during operation. This is especially advantageous in the case of the implementation of rigid reinforcement elements, such as wires or brackets. The tissue, wrapped around the reinforcement elements, provides a soft contact surface for the prosthetic heart valve tissue and hence prevents it from rubbing and reduces wear.

In addition to the reinforcement elements, other stent structures may also be wrapped in tissue or any other suitable synthetic cover. That is, in order to avoid abrasion of the prosthetic heart valve against the stent structure (e.g. retaining arches), the stent may be wrapped in tissue or any other suitable material. In accordance with this particular embodiment of the present disclosure, the heart valve tissue may not be sutured directly to the metallic stent structure but to the tissue or synthetic material covering it. This could provide a closer contact between the prosthetic heart valve and the stent so as to reliably prevent paravalvular leakage.

Yet another modification of the present disclosure includes exposing the prosthetic heart valve material surface and structure to polymeric material in order to reinforce it. Materials according to this embodiment could be cyanoacrylates or polyepoxides which imply excellent bonding of body tissue and could even be used for suture-less surgery.

In a similar realisation the bendable transition portion of the prosthetic heart valve material includes a layering of various materials with differing mechanical properties used to improve the durability of the prosthetic heart valve. To this end, layer materials with very high suture retention strength overlapping the valve material in regions of very high stress load may be applied. As to that, material layers with high suture retention in lower parts of the transition area of the prosthetic heart valve may be provided, whereas the upper parts of the transition area shall be designed to be flexible for improving the durability of the valve. Examples for such layer materials will be explained in more detail, with reference to the "reinforcement elements" below.

With regard to another embodiment of the present disclosure, an attachment for the prosthetic heart valve material that reduces the concentration of stresses at the bendable transition portion is disclosed. In this embodiment, the bendable transition portion of the prosthetic heart valve is attached to the retaining arches of the stent by folding the valve material from the outside of the stent through slots provided along the retaining arches. As mentioned previously, the edges of the slotted retaining arches may be rounded and smooth to avoid abrading or wearing of the valve material. In this design, there is some material thickness on the outside of the stent, which could impinge on the anchoring of the stent at the position of the diseased natural prosthetic heart valve.

To accommodate this issue, a thinning of the retaining arches relative to the rest of the stent structure could be conducted. This would also allow for a recess when the stent is compressed so that the collapsed prosthesis does not require a larger delivery catheter.

According to an alternative embodiment of the present disclosure, the prosthetic heart valve is assembled with three separate pieces of pericardial tissue. According to this, the three separate pieces of pericardial tissue are advantageous regarding the thickness of the prosthetic heart valve tissue. When using a one piece flat tissue in order to form the prosthetic heart valve, the thickness of the leaflets can vary and result in less desirable valve performance, unsymmetrical valve opening and closure or less desirable hemodynamics, such as a short durability or insufficient leaflet closure. Therefore, three smaller pieces of pericardial tissue provide the possibility to form prosthetic heart valve with more uniform thicknesses and mechanical properties.

To this end, another embodiment of the present disclosure includes that each of the three separate pieces has a flat tissue pattern in an essentially T-shirt like shape, exhibiting sleeves for connection between the adjacent pieces. As mentioned previously, the adjacent pieces can be constructed, as to reinforce the contiguous edges of the adjacent pieces. To accomplish this, the sleeves of adjacent pieces can be folded to the outside and sutured together to reinforce the joining connection. Attaching this reinforced area to the stent commissure attachment region helps to more uniformly distribute leaflet stresses supported by the commissure attachment.

In order to further improve the reinforcement of the contiguous edges of the separate pieces, in another embodiment of the present invention, the reinforcement elements consist of outer wrapping elements, wrapped around the sleeves of the three separate pieces, in order to reinforce the prosthetic heart valve and attach it to the commissure attachment region of the stent. That is, an outer wrapping element can be used in order to further improve the durability of the prosthetic heart valve. In this regard, the outer wrapping element can consist of a piece of pericardial tissue or a synthetic material respectively. Also, the outer wrapping element is used to attach the reinforced prosthetic heart valve to the commissure attachment region of the stent by means of sutures. Therefore, the stresses due to the suturing between the stent and the prosthetic heart valve is mainly introduced into the material of the reinforcement element, avoiding high stress concentrations in the prosthetic heart valve.

The following will make reference to the attached drawings in describing preferred embodiments of the prosthetic heart valve, a corresponding stent and a transcatheter delivered endoprosthesis according to the present disclosure in greater detail.

BRIEF DESCRIPTION OF THE DRAWINGS

Shown are.

DETAILED DESCRIPTION

Figure 1:
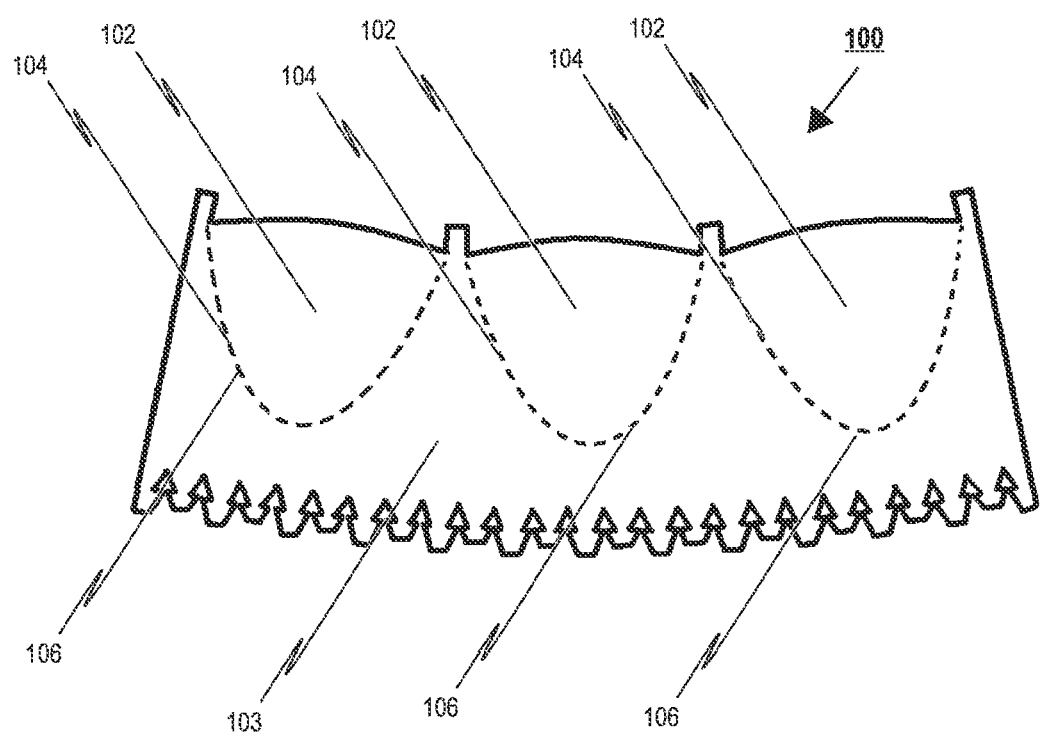
FIG. 1 a roll-out view of a prosthetic heart valve according to an exemplary embodiment of the disclosure.

FIG. 1 shows a view of a flat tissue pattern for a prosthetic heart valve 100 according to an exemplary disclosed embodiment. The prosthetic heart valve 100 may comprise at least two leaflets, and as shown in the exemplary embodiment of the flat tissue pattern for a prosthetic heart valve 100 depicted in FIG. 1 three leaflets 102. Each of the leaflets 102 comprises a natural tissue and/or synthetic material. The leaflets 102 are attached to a skirt portion 103. As will be discussed later on in detail, the skirt portion 103 is used for mounting the prosthetic heart valve 100 to a stent 10.

The leaflets 102 of the prosthetic heart valve 100 are adapted to be moveable from a first opened position for opening the heart chamber and a second closed position for closing the heart chamber. In particular, in the implanted state of the prosthetic heart valve 100, the leaflets 102 may switch between their first and second position in response to the blood flow through the patient's heart. During ventricular systole, pressure rises in the left ventricle of the patient's heart. When the pressure in the left ventricle of the patient's heart rises above the pressure in the aorta the leaflets 102 of prosthetic heart valve 100 opens, allowing blood to exit the left ventricle into the aorta. When ventricular systole ends, pressure in the left ventricle rapidly drops. When the pressure in the left ventricle decreases, the aortic pressure forces the leaflets 102 of the prosthetic heart valve 100 to close.

Figure 2A:
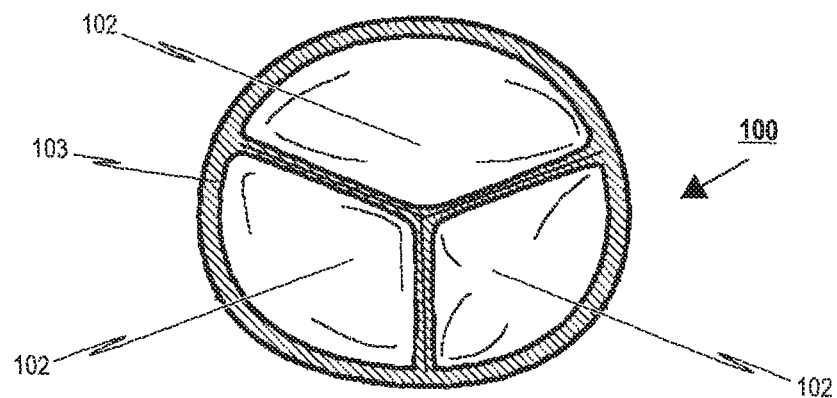
FIG. 2a a plan view of the upper end of the prosthetic heart valve in its closed state.
Figure 2B:
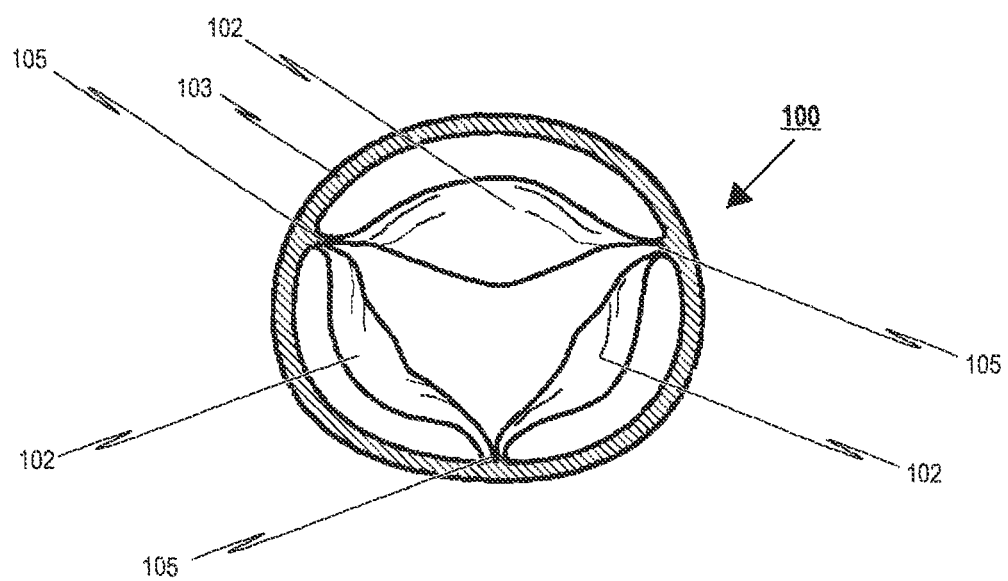
FIG. 2b a plan view of the upper end of the prosthetic heart valve in its opened state.

FIGS. 2a and 2b respectively show a plan view of the upper end of a prosthetic heart valve 100 in the closed and opened state. In the closed position of the prosthetic heart valve 100 (see FIG. 2a), the three leaflets 102 come together in the centre of the prosthetic heart valve 100 thereby creating a region of sealing.

During the opening phase the leaflets pivot about a bendable transition area 104, as depicted in FIG. 1. The bendable transition area 104 forms a junction between the leaflets 102 and the skirt portion 103 and progresses in a substantial U-shaped manner, similar to the cusp shape of a natural aortic or pulmonary heart valve. Still within the opening phase, the commissure region 105 and the leaflets 102 move radially outwards opening the valve in response to increased differential pressure allowing blood to flow through the prosthesis.

In the exemplary embodiment depicted in FIG. 1, the prosthetic heart valve 100 is made of one piece of flat pericardial tissue. This pericardial tissue can either be extracted from an animal's heart (xenograft) or a human's heart (homograft). The extracted tissue may be cut by a laser or knife or might be pressed in order to form a flat tissue pattern representing each of the leaflets 102 and the skirt portion 103. After said forming of the flat tissue pattern, the so made heart valve tissue may be sewn into a cylindrical or conical shape, ready to be attached to a corresponding stent structure 10. As will be discussed in detail with respect to FIGS. 6a, 6b, the skirt portion 103 represents an area of the prosthetic heart valve 100 that is used for connecting the prosthetic heart valve 100 to a stent 10, for example, by means of sutures 101.

As can be seen from FIGS. 1 and 2, the pattern of the prosthetic heart valve 100 represents each of the leaflets 102, commissure region 105 and the skirt portion 103 of the intended prosthetic heart valve 100. Hence, the flat tissue pattern is designed so as to form the leaflets 102 in a manner, having three half-moon shaped leaflets like the aortic or pulmonary heart valve. The leaflets 102 can be designed in various shapes such as the geometry of an ellipse, U-shape or substantially oval. Preferably the three leaflets 102 are formed in such a manner that all of them have the same general shape.

Another aspect shown by FIG. 1 is a flared lower end section of prosthetic heart valve 100. As will be explained in more detail below, such a flared lower end section may be advantageous in order to fit the prosthetic heart valve 100 to an annular collar 40 of a respective cardiac heart valve 10. Alternatively, it is further conceivable to produce a prosthetic heart valve 100 comprising a tapered lower end section. A flare or taper at the lower end section of the prosthetic heart valve 100 may be adapted to the geometry of the blood vessel at the implantation site of the prosthesis, so as to obtain the most reliable fit of said prosthesis to said blood vessel.

Between the leaflets 102 and the skirt portion 103, the valve pattern shows the bendable transition area 104 progressing in a substantial U-shaped manner, similar to the cusp-shape of a natural aortic or pulmonary heart valve.

As can be derived from FIG. 2a, the leaflet portion of the prosthetic heart valve 100 is designed to provide redundant coaptation for potential annular distortion. Accordingly, the redundant coaptation may reduce stress on the leaflets 102 and assures a reliable closure of the heart chamber in the second closed position of the leaflets 102. This redundant coaptation provides for more surface contact between the leaflets, allowing for the prosthetic heart valve of the present disclosure to be implanted in a distorted valve annulus, still maintaining sufficient coaptation.

Although not depicted in FIG. 1, the prosthetic heart valve 100 can comprise a plurality of fastening holes 106 provided along the progression of the transition area 104. These fastening holes 106 are introduced into the tissue material of the prosthetic heart valve 100 by means of laser cutting for strengthening the tissue area around the fastening holes 106. Alternatively, however, it is conceivable that fastening holes 106 are introduced by the needle during the sewing process.

The bendable transition area 104 shown in FIG. 1 may include a layering of various materials with differing mechanical properties. Accordingly, the lower parts, particularly associated with retaining arches of a cardiac valve stent, may be more rigid to provide high suture retention, whereas the upper parts, particularly associated with a commissure attachment region 11b of the stent, may be designed to be more flexible in order to support the movement of the leaflets 102. On the same note, the leaflets 102 and the leaflet support portion 103 may exhibit different stability characteristics. This might be achieved by the use of different cross-linking processes for the leaflets 102 or the leaflet support portion 103 respectively. Alternatively, the leaflets 102 or the leaflet support portion 103 could be reinforced by attaching small sheets of tissue or synthetic material in order to increase the mechanical stability.

As the size and diameter of different blood vessels of different patients varies to a certain extent, it may be advantageous to provide prosthetic heart valves 100 of different designs. In particular, tissue material with a thickness of 160 µm to 300 µm, more preferably 220 µm to 260 µm may be used, depending on the particular tissue material used to manufacture the prosthetic heart valve. Furthermore, the prosthetic heart valve 100, according to the present disclosure, may have a diameter ranging form 19 mm to 28 mm.

Figure 6A:
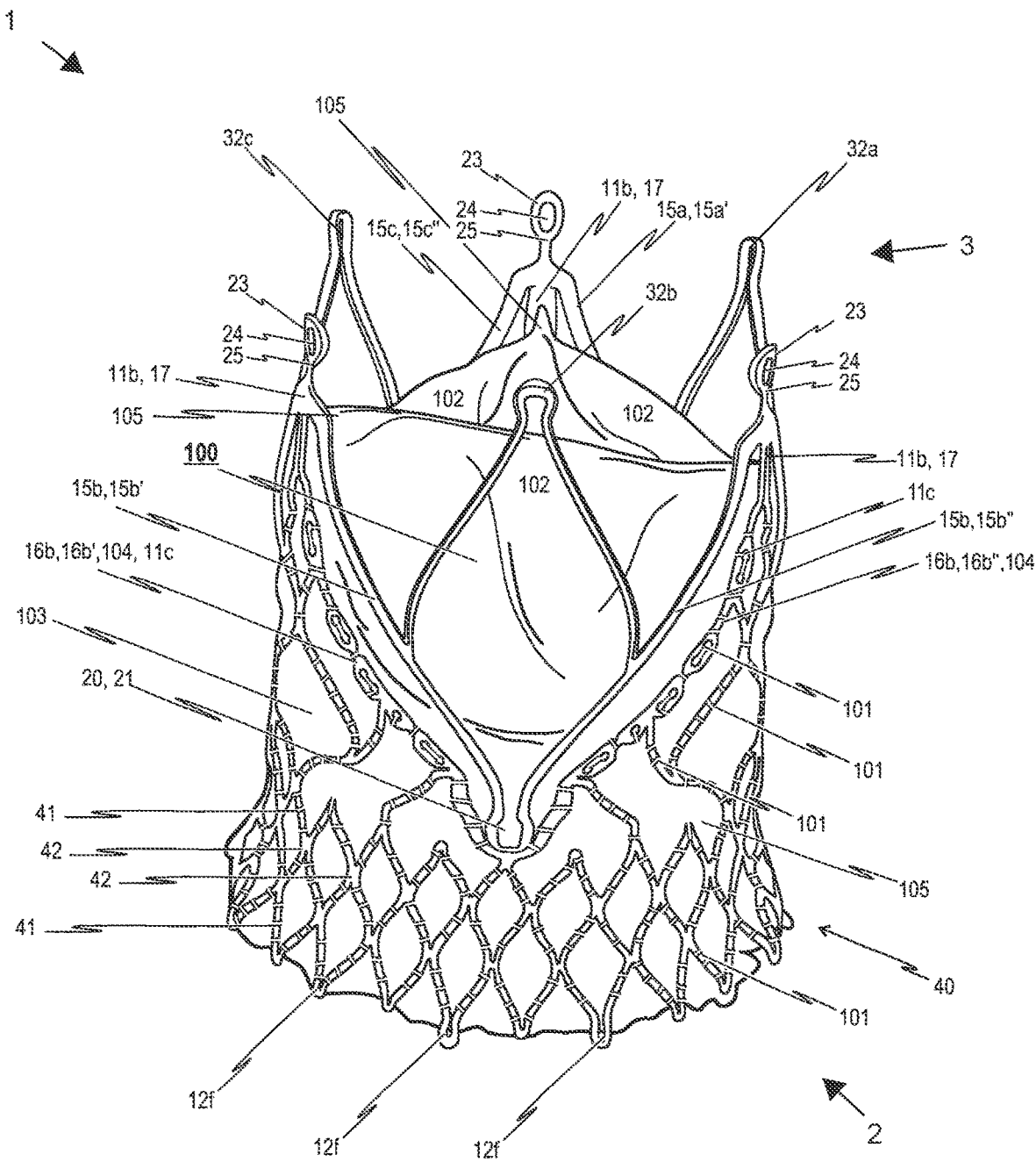
FIG. 6a a first perspective side view of an endoprosthesis for treating a narrowed cardiac valve or a cardiac valve insufficiency, where the endoprosthesis is shown in an expanded state and where the endoprosthesis comprises a cardiac valve stent and a prosthetic heart valve according to an exemplary embodiment of the disclosure, said cardiac valve stent is used for holding the prosthetic heart valve.

Reference is made in the following to FIGS. 6a, b which respectively show a first and second perspective side view of an endoprosthesis 1 for treating a narrowed cardiac valve or a cardiac valve insufficiency, where the endoprosthesis 1 comprises an exemplary embodiment of a cardiac valve stent 10 for holding a prosthetic heart valve 100. In the illustrations according to FIGS. 6a, b, the endoprosthesis 1 is shown in an expanded state.

As can be seen from the illustrations according to FIGS. 6a, b, in the affixed state of the prosthetic heart valve 100, the transition area 104 of the prosthetic heart valve 100 extends along the retaining arches 16a, 16b, 16c and, in particular, along the lower leaflet attachment region 11c and the commissure attachment region 11b of the retaining arches 16a, 16b, 16c of the stent 10. The bendable transition area 104 of the prosthetic heart valve 100 is attached to retaining arches 16a, 16b, 16c of the stent 10 such as to enable the leaflets 102 of the prosthetic heart valve 100 to bend inwards in a controlled manner to the centre of the stent 10 forming the valvular leaflets 102.

For adapting the prosthetic heart valve 100 to a corresponding stent 10 so that the valvular leaflets 102 are properly formed and prosthetic heart valve is properly fitted to the stent structure, the pattern of the flat-tissue material of the prosthetic heart valve 100 shall be cut so as to incorporate the leaflet structures, the annular skirt portion 103 and the transition area 104 in between them. In other words, after the prosthetic heart valve material is sewn into its cylindrical or conical shape, the valve exhibits a flared portion at the lower end. This flared geometry fits the structure of the stent 10 and is constructed to optimally fit the vascular wall at the implantation site of the diseased heart valve.

In the exemplary embodiment of the transcatheter delivered endoprosthesis 1 depicted in FIGS. 6a, b, the prosthetic heart valve 100, which is affixed to the stent 10, consists of a one piece flat pericardial tissue material extracted from an animal or human pericardial sack and cut into a pattern representing each of the three leaflets 102 and the skirt portion 103, wherein the pattern is sewn into a cylindrical shape before attachment to the stent 10. In addition, the prosthetic heart valve 100 includes a transition area 104 which is connected to the retaining arches 16a, 16b, 16c and commissure attachment regions 11b of the stent. The transition area 104 connects the leaflets 102 with the skirt portion 103. In particular, the transition area 104 is essentially U-shaped, similar to the cusp shape of a natural aortic or pulmonary heart valve. For this reason, the transition area 104 allows for an opening and closing motion of the leaflets 102, causing minimal stresses within the biological prosthetic heart valve tissue.

Upon assembly of this tissue pattern (see FIG. 1) to a stent 10, the regions of tissue between the retaining arches 10 become the valve leaflets 102. These leaflets can be folded inwards so as to form three essentially closed leaflets. In case of a pressure gradient in a downstream direction (in response to a rising blood pressure in the heart chamber), the leaflets 102 are forced apart, in the direction of the stent 10, enabling blood to exit the heart chambers. On the other hand, if there is a pressure gradient in the opposite, upstream direction (retrograde gradient, in response to an intake pressure in the heart chamber), the blood rushes into the leaflets 102, thereby pressing the leaflets 102 together in the centre of stent 10 and closing the transcatheter delivered endoprosthesis 1.

As has been described in more detail with reference to FIGS. 5a-e and FIGS. 8 to 10, a suitable stent 10, to which the prosthetic heart valve 100 may be attached for forming an endoprosthesis 1, may include an annular collar 40 arranged to a lower section of stent 10. The annular collar 40 of the stent 10 serves as an additional anchoring measure to hold the transcatheter delivered endoprosthesis 1 in a desired location at the site of the diseased heart valve. In the exemplary embodiment of the transcatheter delivered endoprosthesis 1 depicted in FIGS. 6a, b, FIGS. 7a, b and FIGS. 11a to 11c, the annular collar 40 of the stent 100 has a flared shape.

Accordingly, the lower part of leaflet support portion 103 of the prosthetic heart valve 100 affixed to the stent 10 also exhibits an extended diameter in order to accommodate the flared shape of the annular collar 40.

The prosthetic heart valve 100 is fixed to the stent 10 by means of sutures, threads or wires 101 which are attached to the skirt portion 103 and/or the transition area 104 of the prosthetic heart valve 100. The skirt portion 103 serves for keeping the prosthetic heart valve 100 in a predefined position relative to the stent 10.

As will be described in more detail below, a suitable stent 10, to which the prosthetic heart valve 100 may be attached for forming an endoprosthesis 1, may include an annular collar 40 arranged to a lower section of stent 10. The annular collar 40 of the stent 10 serves as an additional anchoring measure to hold the transcatheter delivered endoprosthesis 1 in a desired location at the site of the diseased heart valve.

As can be seen from the illustrations in FIGS. 6a, b, the skirt portion 103 of the prosthetic heart valve 100 may also be attached to the annular collar 40 of the stent 10 by means of sutures, threads or wires 101. For this purpose, multifilament sutures 101 of a diameter up to 0.2 mm, preferably between 0.1 mm and 0.2 mm may be used.

Moreover, a common running stitch pattern may be used to obtain said bonding. According to the disclosure, the stitch pattern is preferably a locking stitch or a blanket stitch respectively. Of course, any other suitable stitch pattern (i.e. overlocking stitch, slipstitch or topstitch) is also possible.

Figure 6B:
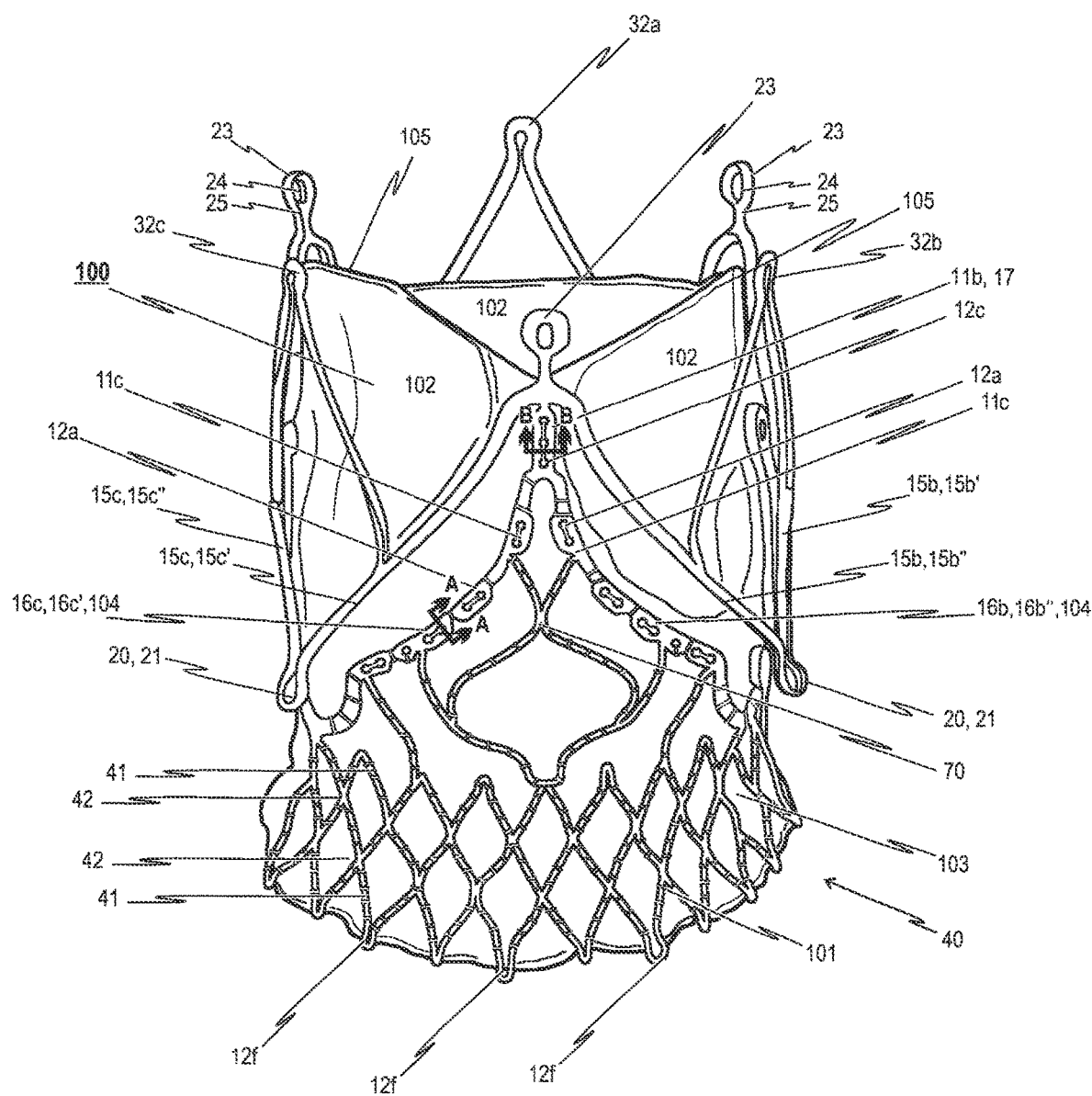
FIG. 6b a second perspective side view of an endoprosthesis for treating a narrowed cardiac valve or a cardiac valve insufficiency, where the endoprosthesis is shown in an expanded state and where the endoprosthesis comprises a cardiac valve stent and a prosthetic heart valve according to an exemplary embodiment of the disclosure, said cardiac valve stent is used for holding the prosthetic heart valve.

As indicated by FIGS. 6a and 6b, the bendable transition area 104 of the prosthetic heart valve may be attached to retaining arches 16a, 16b, 16c of the stent 10 by means of sutures 101, having a diameter larger than the diameter of the sutures 101 used for attachment of the prosthetic heart valve to an annular collar 40 of the stent 10. Due to this, the prosthetic heart valve 100 can be reliably attached to the stent without adding too much bulk to the stent 10, in order to collapse the endoprosthesis to a small diameter.

In the exemplary embodiment of the transcatheter delivered endoprosthesis 1 depicted in FIGS. 6a, b, the annular collar 40 of the stent 100 has a flared shape. Accordingly, the lower part of skirt portion 103 of the prosthetic heart valve 100 affixed to the stent 10 also exhibits an extended diameter in order to accommodate the flared shape of the annular collar 40.

The scope of the present disclosure will become more clear by considering some of the possible embodiments of a stent 10 with the prosthetic heart valve 100 attached thereto thereby forming an endoprosthesis. Hence, reference is made in the following to FIGS. 5*a-e* for describing an exemplary embodiment of a stent 10 to which a prosthetic heart valve 100 may be affixed in order to form the transcatheter delivered endoprosthesis 1 depicted in FIGS. 6*a, b*.

Figure 5A:
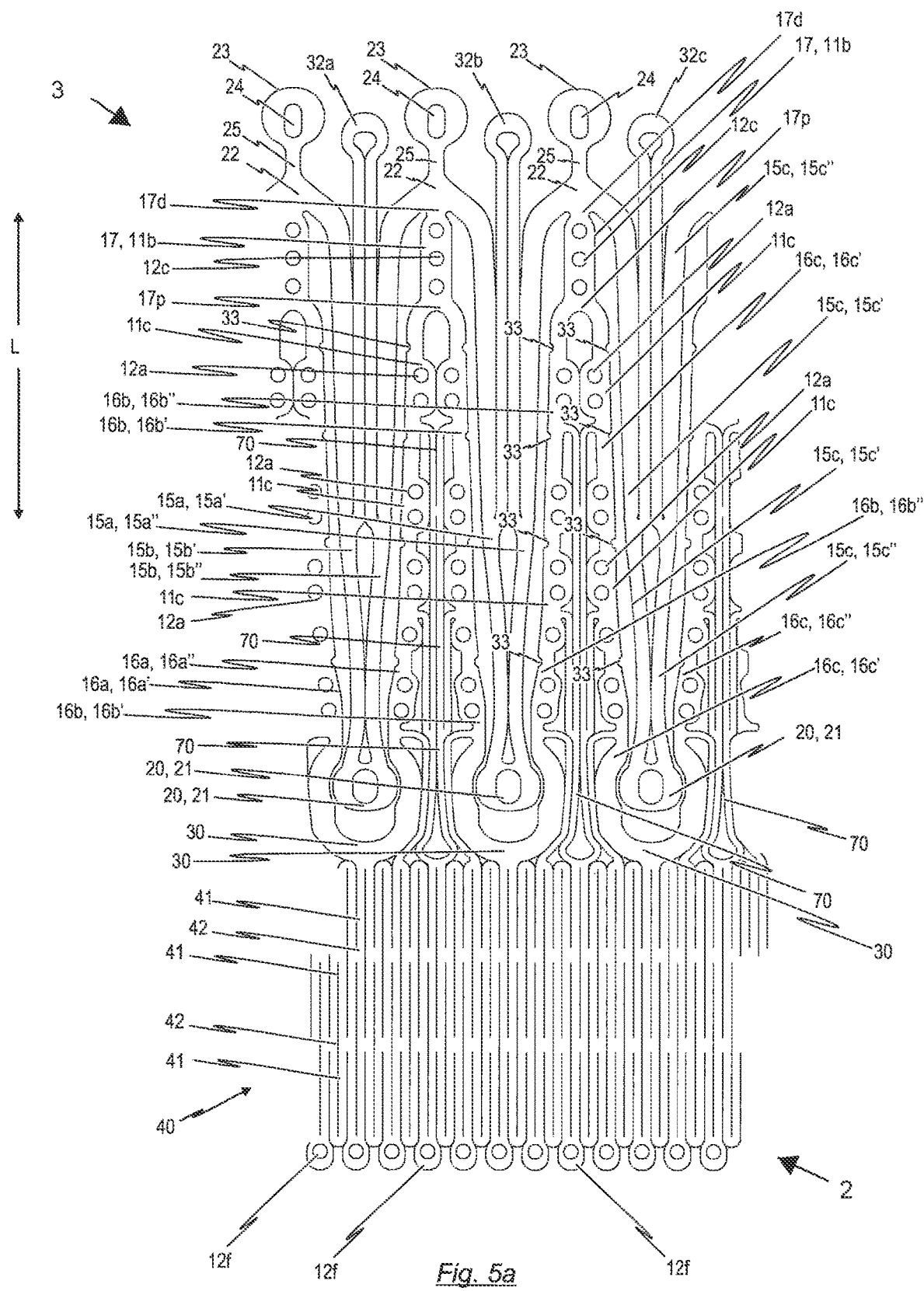
FIG. 5a a flat roll-out view of an exemplary embodiment of a first cardiac valve stent which may be used in the endoprosthesis according to FIG. 6a, 6b, 7a or 7b for fixing a prosthetic heart valve according to an exemplary embodiment of the disclosure.
Figure 5B:
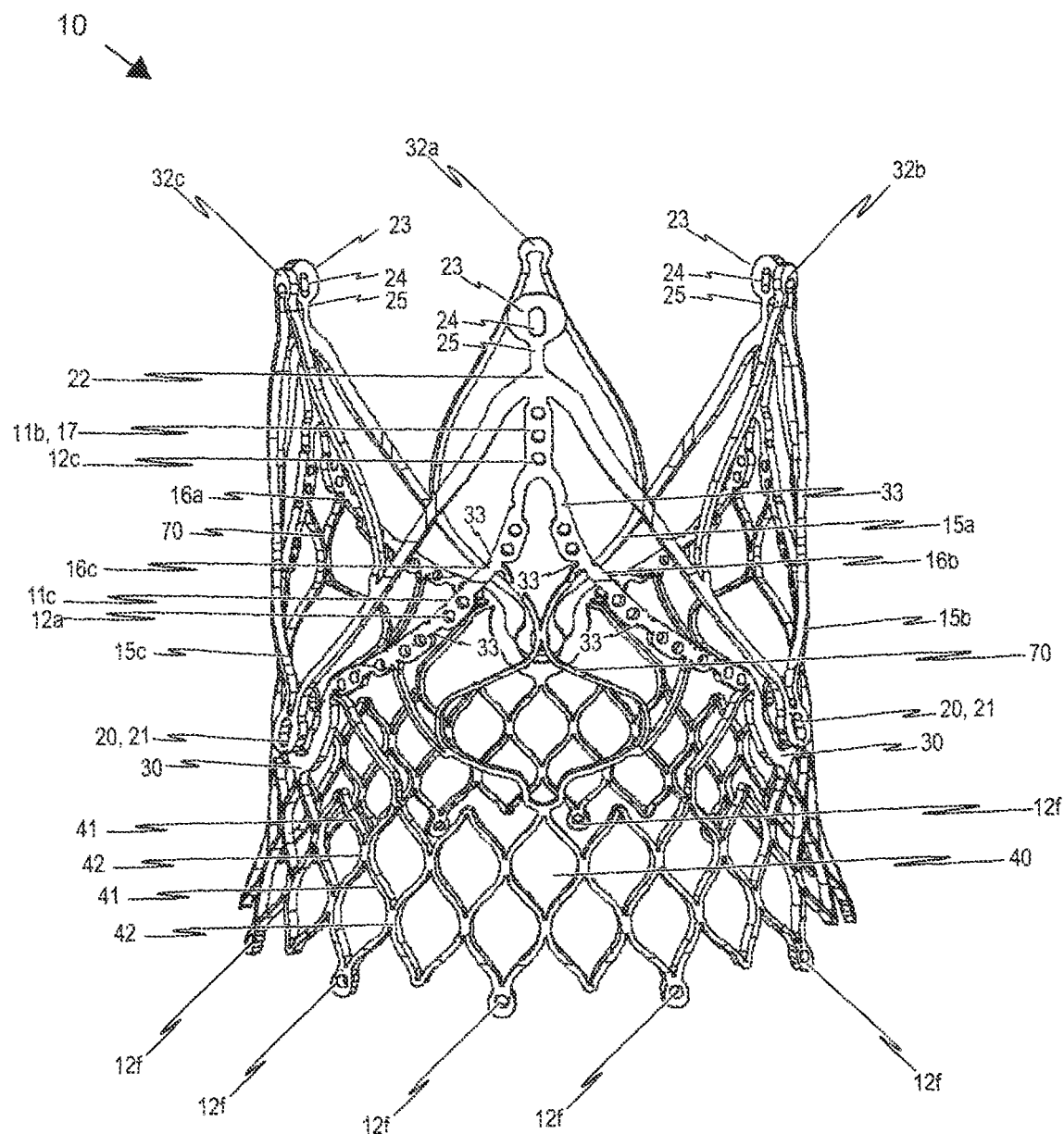
FIG. 5b a first perspective side view of a first cardiac valve stent capable of supporting and anchoring a prosthetic heart valve according to an exemplary embodiment of the disclosure, whereby the cardiac valve stent is shown in its expanded state.
Figure 5C:
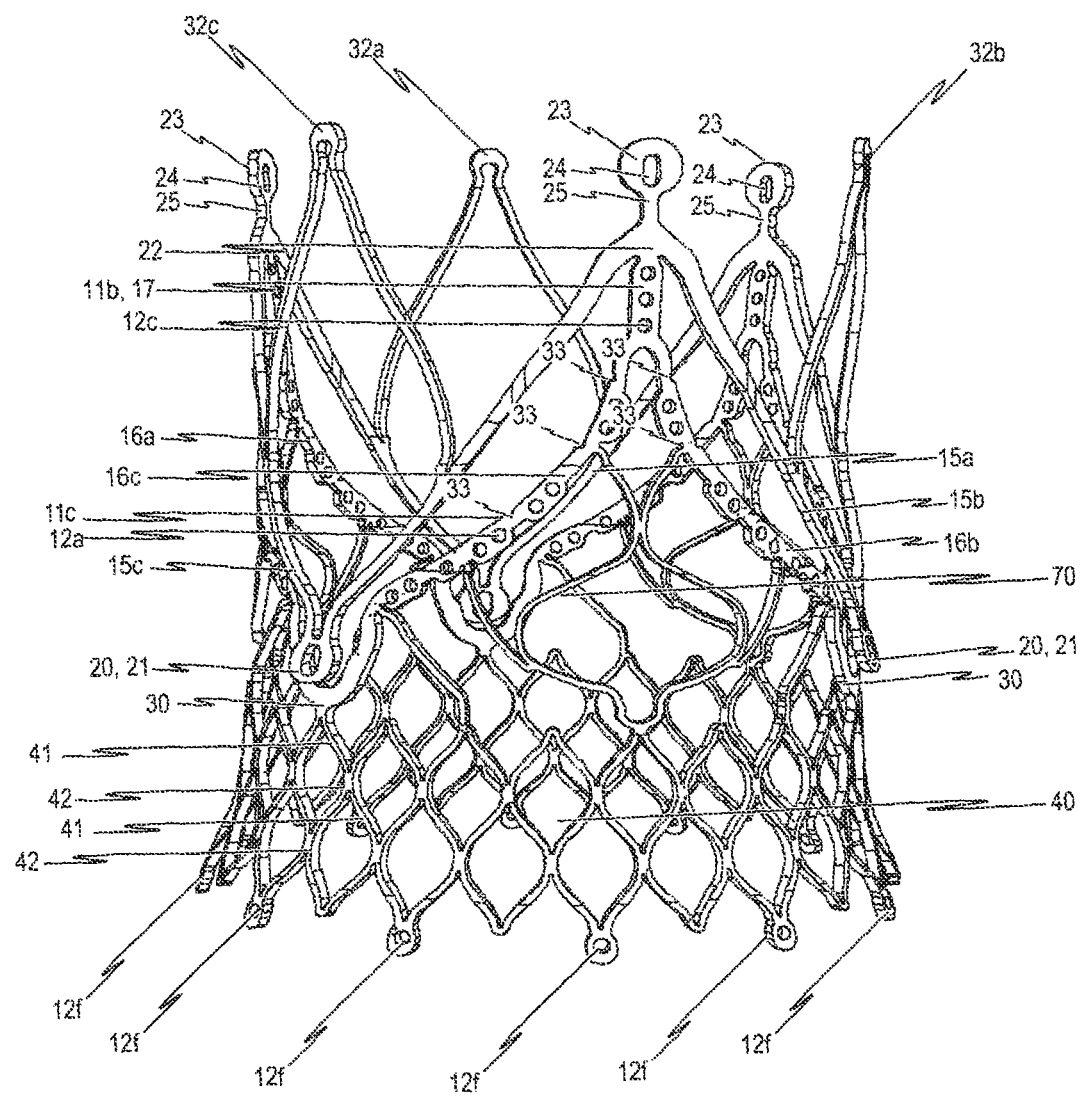
FIG. 5c a second perspective side view of a first cardiac valve stent capable of supporting and anchoring a prosthetic heart valve according to an exemplary embodiment of the disclosure, whereby the cardiac valve stent is shown in its expanded state.
Figure 5D:
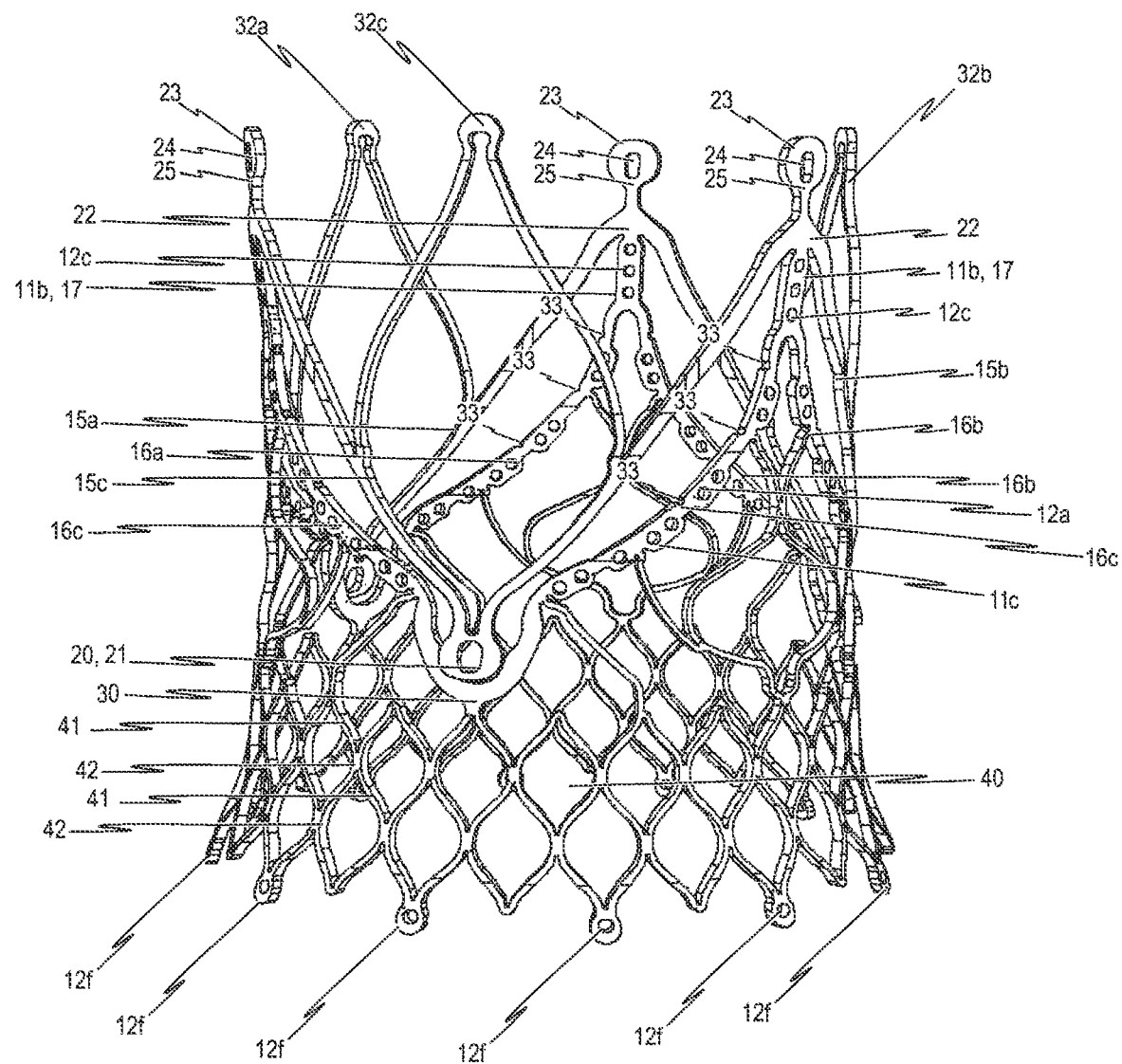
FIG. 5d a third perspective side view of a first cardiac valve stent capable of supporting and anchoring a prosthetic heart valve according to an exemplary embodiment of the disclosure, whereby the cardiac valve stent is shown in its expanded state.

In particular, FIG. 5*b* is a first perspective side view of a cardiac valve stent 10, whereby the cardiac valve stent 10 is shown in its expanded state. Second and third side views of the cardiac valve stent 10 in its expanded state are shown in FIGS. 5*c* and 5*d*.

Figure 5E:
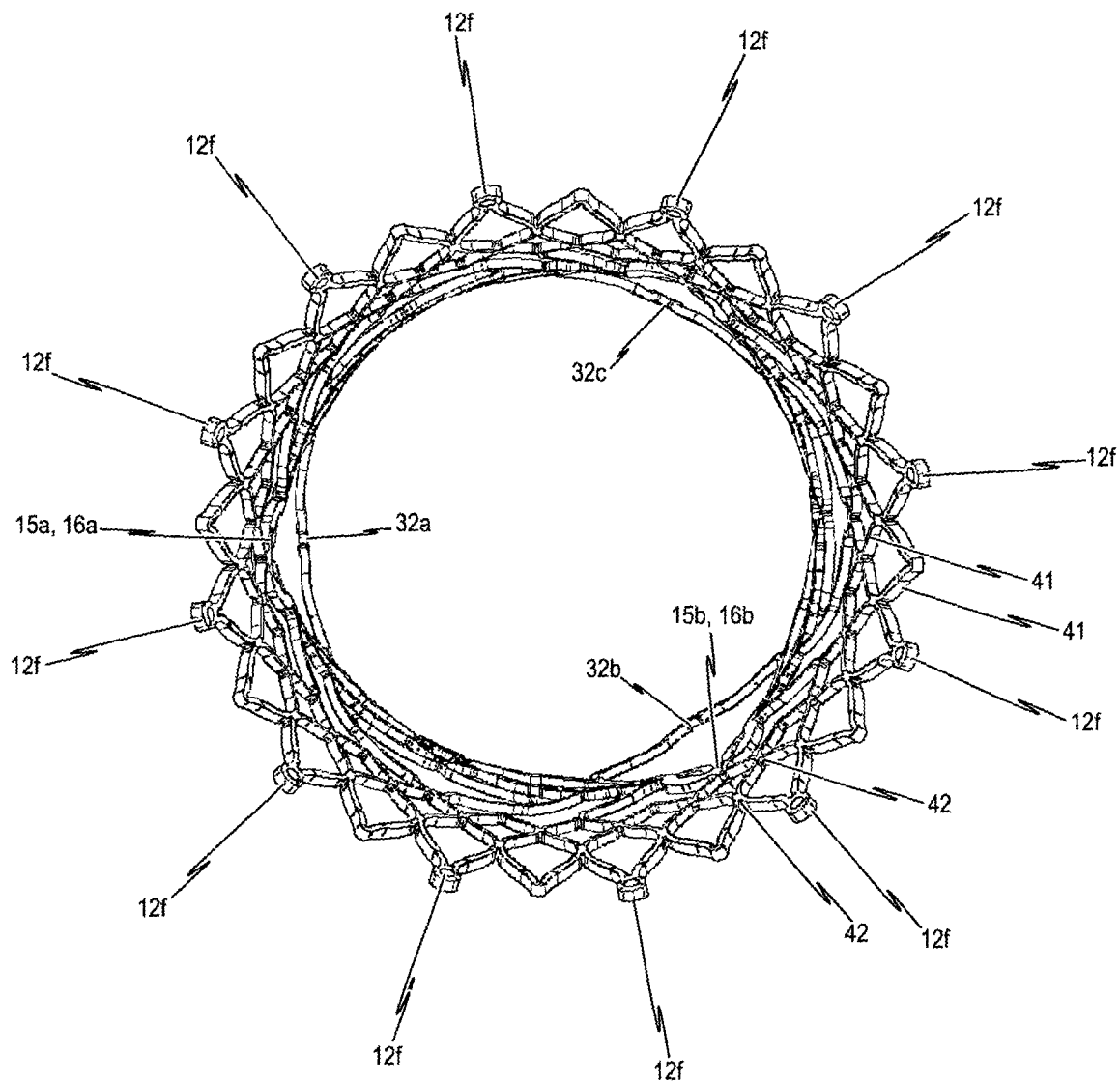
FIG. 5e a plan view of the lower end of a first cardiac valve stent capable of supporting and anchoring a prosthetic heart valve according to an exemplary embodiment of the disclosure, whereby the cardiac valve stent is shown in its expanded state.

On the other hand, FIG. 5*e* shows a plan view of the lower end of the cardiac valve stent 10 according to the exemplary embodiment of the disclosure in its expanded state, whereas a flat roll-out view of a stent 10 according to the exemplary embodiment is shown in FIG. 5*a*.

The stent 10 depicted in FIGS. 5*a-e* is also provided with an annular collar 40 which is arranged at the lower end section of the stent body. The at least one collar 40 may serve as an additional anchoring measure for the stent 10.

In addition, the stent 10 according to the exemplary embodiment has a total of three positioning arches 15*a*, 15*b*, 15*c*, which undertake the function of automatic positioning of the stent 10. Each of the positioning arches 15*a*, 15*b*, 15*c* has a radiused head portion 20, which engages in the pockets of the native heart valve being treated during positioning of the stent 10 at the implantation site in the heart.

The exemplary embodiment of the stent 10 also includes radial arches 32*a*, 32*b*, 32*c*. In particular, the stent 10 has three radial arches 32*a*, 32*b*, 32*c*, with each arch 32*a*, 32*b*, 32*c* located between the two arms 15*a*, 15*a'*, 15*b*, 15*b'*, 15*c*, 15*c'* of each positioning arch 15*a*, 15*b*, 15*c*. Each radial arch 32*a*, 32*b*, 32*c* has a shape that is roughly inverse to each positioning arch 15*a*, 15*b*, 15*c* and extends in the opposite direction to each one of the positioning arches 15*a*, 15*b*, 15*c*.

In addition, the stent 10 according to the exemplary embodiment depicted in FIGS. 5*a-e* is provided with corresponding retaining arches 16*a*, 16*b*, 16*c*. Each one of the retaining arches 16*a*, 16*b*, 16*c* is allocated to one of the positioning arches 15*a*, 15*b*, 15*c*. Also, according to this exemplary embodiment of the stent 10, a number of commissure attachment regions 11*b* with a number of additional fastening holes 12*c* is configured at one end of each arm 16*a'*, 16*a"*, 16*b'*, 16*b"*, 16*c'*, 16*c"* of the retaining arches 16*a*, 16*b*, 16*c*.

In addition to the commissure attachment regions 11*b*, the stent 10 also comprises second lower leaflet attachment regions 11*c* for additional fastening of the tissue component(s) of a prosthetic heart valve 100 (see FIGS. 6*a, b*). In this regard, the stent 10 according to the exemplary embodiment depicted in FIGS. 5*a-e* has a configuration with a number of attachment regions 11*b*, 11*c* to attach the material of a prosthetic heart valve 100.

The stent 10 may also be provided with leaflet guard arches, wherein one leaflet guard arch may be provided in between each positioning arch 15*a*, 15*b*, 15*c*. The structure and function of the leaflet guard arches will be described later with reference to FIGS. 7*a* and 7*b*. Hence, although for reasons of clarity not explicitly shown, in the stent design according to the exemplary embodiment depicted in FIGS. 5*a-e*, one leaflet guard arch may be allocated to each positioning arch 15*a*, 15*b*, 15*c*.

The exemplary embodiment of the sent 10 is characterized by a specific structure of the respective arms 16*a'*, 16*a"*, 16*b'*, 16*b"*, 16*c'*, 16*c"* of the retaining arches 16*a*, 16*b*, 16*c*.

In detail, in the expanded state of the stent 10, the respective arms 16*a'*, 16*a"*, 16*b'*, 16*b"*, 16*c'*, 16*c"* of the retaining arches 16*a*, 16*b*, 16*c* have a shape similar to a prosthetic heart valve 100. Furthermore, the respective arms 16*a'*, 16*a"*, 16*b'*, 16*b"*, 16*c'*, 16*c"* of the retaining arches 16*a*, 16*b*, 16*c* are provided with a number of lower leaflet attachment regions 11*c*, each having a number of additional fastening holes 12*a* or eyelets provided for fastening the tissue component(s) of a prosthetic heart valve 100. These additional fastening holes 12*a* or eyelets provide attachment points for the bendable transition area 104 of a prosthetic heart valve 100 attached to the stent 10.

As will be described in more detailed below, in an alternative embodiment, the respective arms 16*a'*, 16*a"*, 16*b'*, 16*b"*, 16*c'*, 16*c"* of the retaining arches 16*a*, 16*b*, 16*c* may be provided with a number of fastening notches which can be used to fix the bendable transition area 104 to stent 10. Thus, in this alternative embodiment, there are no additional fastening holes 12*a* needed along the respective arms 16*a'*, 16*a"*, 16*b'*, 16*b"*, 16*c'*, 16*c"* of the retaining arches 16*a*, 16*b*, 16*c*.

According to the stent designs of the embodiments depicted in FIGS. 5*a-e* and FIGS. 8 to 10, in the expanded state of the stent 10, the respective arms 16*a'*, 16*a"*, 16*b'*, 16*b"*, 16*c'*, 16*c"* of the retaining arches 16*a*, 16*b*, 16*c* have a shape that substantially matches the transition area 104 of a prosthetic heart valve 100 attached to the stent 10 (see FIG. 6*a, b* or 11*a, b*).

This specific design of the respective arms 16*a'*, 16*a"*, 16*b'*, 16*b"*, 16*c'*, 16*c"* of the retaining arches 16*a*, 16*b*, 16*c* has valve durability advantages. The so formed arms 16*a'*, 16*a"*, 16*b'*, 16*b"*, 16*c'*, 16*c"* of the retaining arches 16*a*, 16*b*, 16*c* serve for supporting the skirt portion 103 and edge of the leaflets 102 of a prosthetic heart valve 100 attached to the stent 10.

As depicted, for example, in FIGS. 6*a, b* and 11*a, b*, the respective arms 16*a'*, 16*a"*, 16*b'*, 16*b"*, 16*c'*, 16*c"* of the retaining arches 16*a*, 16*b*, 16*c* follow the shape of the bendable transition area 104 of a prosthetic heart valve 100 affixed to the stent 10 in its expanded state. Furthermore, the respective arms 16*a'*, 16*a"*, 16*b'*, 16*b"*, 16*c'*, 16*c"* of the retaining arches 16*a*, 16*b*, 16*c* are designed to have a minimized unsupported gap from one arm to the other arm of a retaining arch 16*a*, 16*b*, 16*c* at the location behind the positioning arches 15*a-c*.

In detail and as depicted in the cutting pattern shown in FIG. 5*a*, the respective arms 16*a'*, 16*a"*, 16*b'*, 16*b"*, 16*c'*, 16*c"* of the retaining arches 16*a*, 16*b*, 16*c* are provided with a plurality of bending edges 33. These bending edges 33 divide each arm 16*a'*, 16*a"*, 16*b'*, 16*b"*, 16*c'*, 16*c"* into a plurality of arm segments. The arm segments of a single arm 16*a'*, 16*a"*, 16*b'*, 16*b"*, 16*c'*, 16*c"* of the retaining arches 16*a*, 16*b*, 16*c* are interconnected thereby constituting a retaining arch arm which describes an essentially straight line in the not-expanded state of the stent 10. In this regard, reference is also made to the cutting pattern depicted in FIG. 5*a* which shows the uncurved configuration of the respective arms 16*a'*, 16*a"*, 16*b'*, 16*b"*, 16*c'*, 16*c"* of the retaining arches 16*a*, 16*b*, 16*c*.

When manufacturing the stent 10, the stent structure and in particular the structure of the retaining arches 16*a*, 16*b*, 16*c* is programmed such that the respective arms 16*a'*, 16*a"*, 16*b'*, 16*b"*, 16*c'*, 16*c"* of the retaining arches 16*a*, 16*b*, 16*c* have a curved shape in the expanded state of the stent 10. The shape of the respective arms 16*a'*, 16*a"*, 16*b'*, 16*b"*, 16*c'*, 16*c"* of the retaining arches 16*a*, 16*b*, 16*c* is such defined that the arms follow the shape of the transition area 104 of a prosthetic heart valve 100 to be affixed to the stent 10 (see FIGS. 6*a* and 6*b*).

Hence, the respective arms 16*a*', 16*a*", 16*b*', 16*b*", 16*c*', 16*c*" of the retaining arches 16*a*, 16*b*, 16*c* of the stent 10, onto which the transition area 104 of a prosthetic heart valve 100 is sewn or sewable, will change their shape when the stent 10 expands, wherein the retaining arches 16*a*, 16*b*, 16*c* are curved in the expanded state of the stent 10, but relatively straight when the stent 10 is collapsed.

Figure 9:
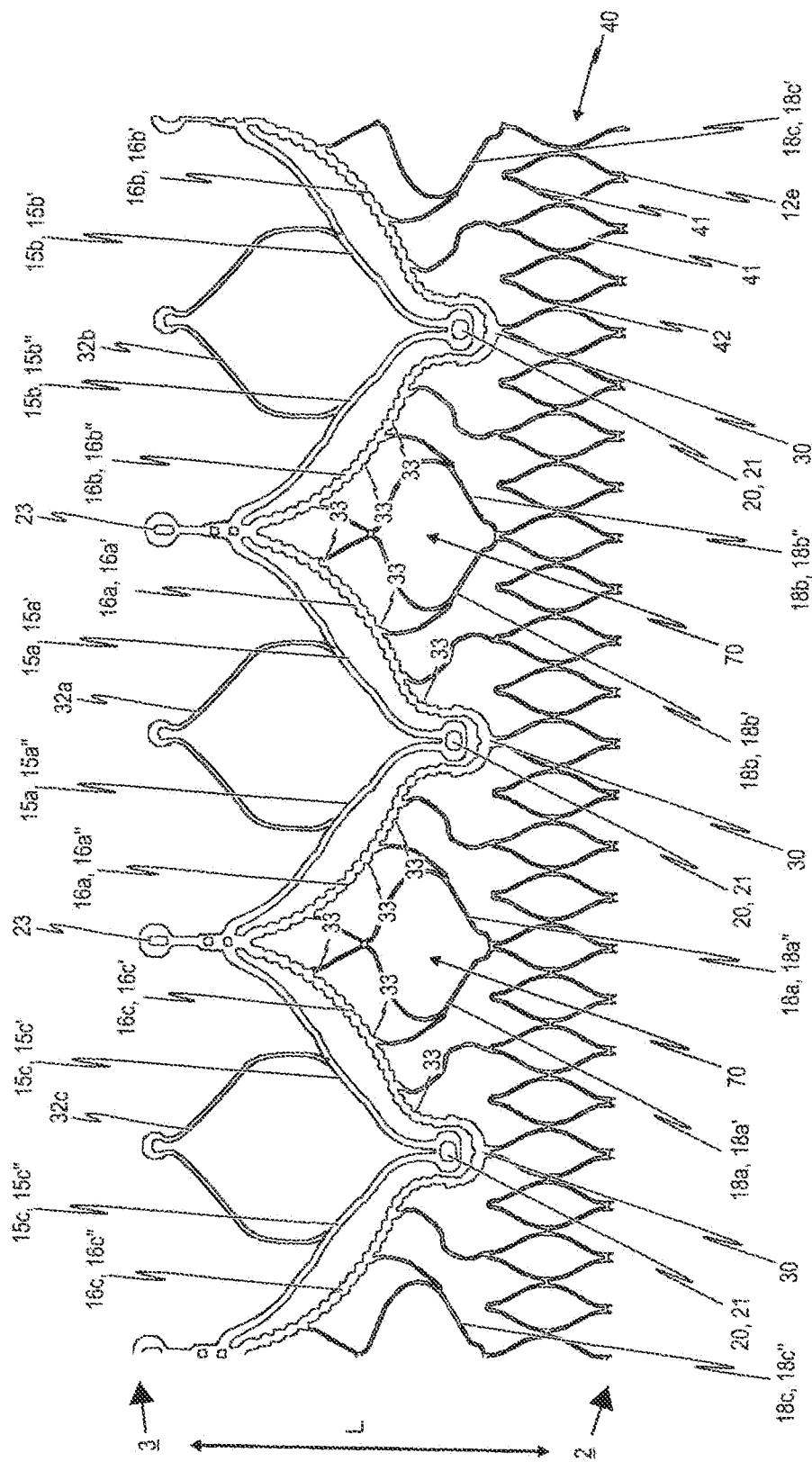
FIG. 9 a flat roll-out view of an exemplary embodiment of a third cardiac valve stent, in its expanded state, which may be used in an endoprosthesis for fixing a prosthetic heart valve according to an exemplary embodiment of the disclosure.
Figure 10:
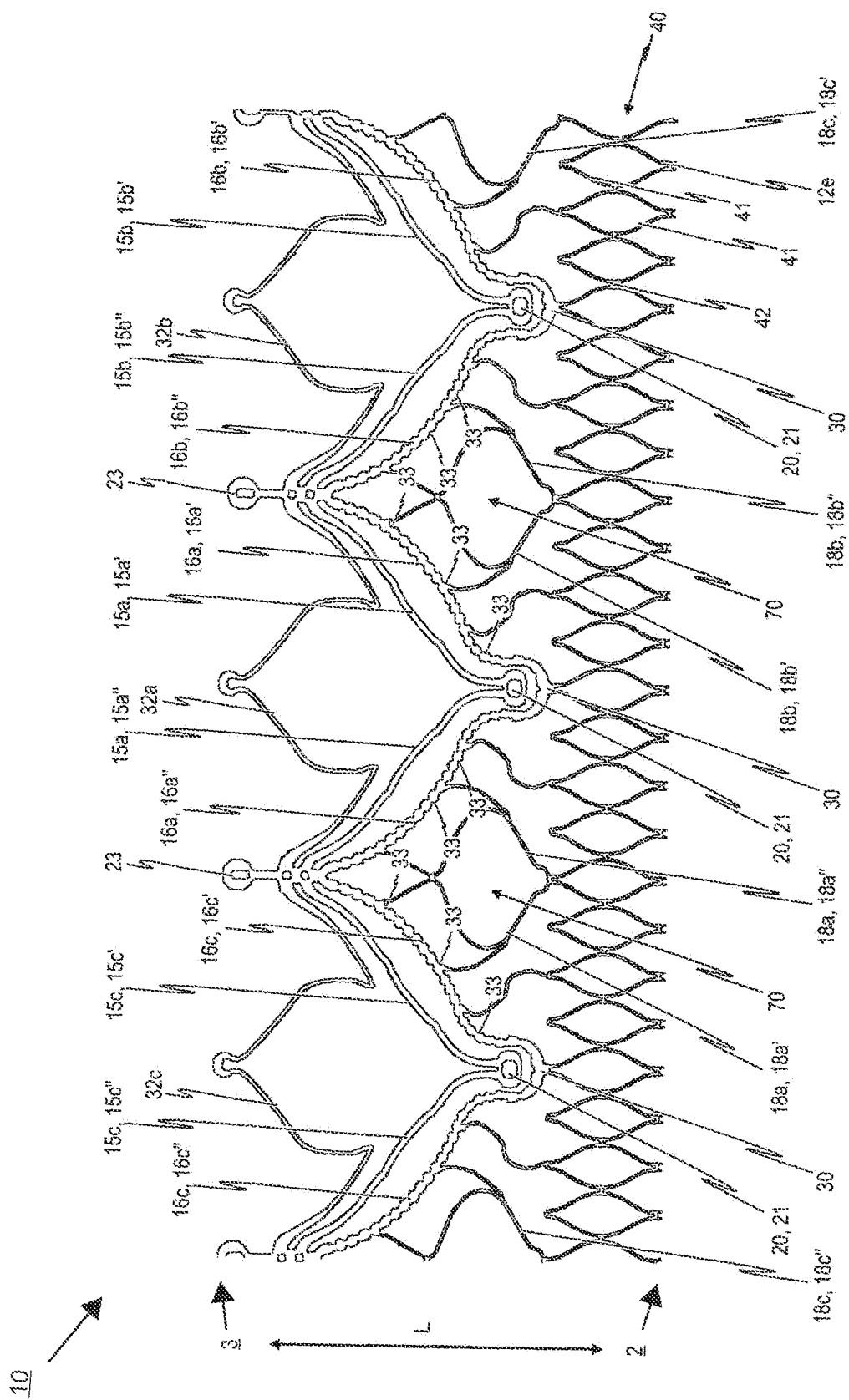
FIG. 10 a flat roll-out view of an exemplary embodiment of a fourth cardiac valve stent, in its expanded state, which may be used an endoprosthesis for fixing a prosthetic heart valve according to an exemplary embodiment of the disclosure.

As can be seen, for example, in FIGS. 5*b-d*, the curvature of the respective arms 16*a*', 16*a*", 16*b*', 16*b*", 16*c*', 16*c*" of the retaining arches 16*a*, 16*b*, 16*c* is achieved by segmenting the arms 16*a*', 16*a*", 16*b*', 16*b*", 16*c*', 16*c*". In detail, the arms 16*a*', 16*a*", 16*b*', 16*b*", 16*c*', 16*c*" are segmented by providing a plurality of bending edges 33. In the expanded state of the stent 10, two neighboring arm segments are angled relative to each other, wherein the bending point of these two neighboring arm segments is defined by the bending edge 33 which is provided in between the both neighboring arm segments. Hence, the greater the number of bending edges 33 provided in an arm 16*a*', 16*a*", 16*b*', 16*b*", 16*c*', 16*c*" of a retaining arch 16*a*, 16*b*, 16*c*, the greater the number of arm segments which may extend in different directions in the expanded state of the stent 10. In this respect, the shape of the respective arms 16*a*', 16*a*", 16*b*', 16*b*", 16*c*', 16*c*" of the retaining arches 16*a*, 16*b*, 16*c* can be precisely adapted to the shape of transition area 104 of a prosthetic heart valve 100 to be affixed to the stent 10. Also, it should be noted that the embodiments depicted in FIGS. 8 to 10 show an even higher number of bending edges 33 providing a plurality of arm segments. Further to this, the bending edges 33 depicted in FIGS. 8 to 10 are formed so as to provide a plurality of fastening notches along the retaining arches 16*a*, 16*b*, 16*c*, as will be described in more detail below.

The stent 10 depicted in FIGS. 5*a-e* is also provided with an annular collar 40 which is arranged at the lower end section of the stent body. The at least one annular collar 40 may serve as an additional anchoring measure for the stent.

In the embodiment depicted in FIGS. 6*a* and 6*b*, the stent 10 corresponds to a stent pursuant the exemplary embodiment previously described with reference to FIGS. 5*a-e*. On the other hand, the prosthetic heart valve 100 affixed to the stent 10 corresponds to the exemplary embodiment of the prosthetic heart valve 100 previously described with reference to FIG. 1 and FIGS. 2*a, b*.

Hence, as shown in the exemplary embodiment of the transcatheter delivered endoprosthesis 1 depicted in FIGS. 6*a, b*, the prosthetic heart valve 100 affixed to the stent 10 comprises three leaflets 102 made from a biological or synthetic material.

To reduce longitudinal displacement of the prosthetic heart valve 100 relative to the stent 10, the stent 10 comprises a plurality of fastening portions in the form of lower leaflet attachment regions 11*c*, essentially extending in the longitudinal direction L of stent 10. In addition, the stent 100 is provided with commissure attachment regions 11*b*. By means of the lower leaflet attachment regions 11*c* and the commissure attachment regions 11*b* (both acting as fastening portion), the tissue components of the prosthetic heart valve 100 are affixed to the stent 10.

In detail, the prosthetic heart valve 100 is fastened to the stent 10 by means of sutures 101, threads or a thin wire which is guided through fastening holes 12*a*, 12*c* of the lower leaflet attachment regions 11*c* and the commissure attachment regions 11*b* respectively. This allows fixing of the tissue components of the prosthetic heart valve 100 to the stent 10 at a predefined position relative to the stent 10.

Alternatively, as will be described with reference to FIGS. 8 to 10, the sutures 101, threads or wires may be guided by fastening notches provided along the retaining arches 16*a*, 16*b*, 16*c*, instead of the aforementioned fastening holes 12*a*. Hence, in the alternative embodiments according to FIGS. 8 to 10, the fastening holes 12*a* of the lower leaflet attachment region 11*c* are replaced by notches (provided by bending edges 33), whereas the commissure attachment region 11*b* may still be provided with fastening holes 12*c*.

It can further be seen from the FIG. 6*a* or FIG. 6*b* illustration how the prosthetic heart valve 100 can be affixed to the stent 10 by means of sutures 101. In the depicted embodiment, a pericardial prosthetic heart valve 100 is used which is sewn to fastening holes 12*a*, 12*c* provided in the fastening portions of the retaining arches 16*a*, 16*b*, 16*c*, i.e. the lower leaflet attachment regions 11*c* on the one hand and in the commissure attachment regions 11*b* on the other hand. In order to improve the attachment of the prosthetic heart valve 100 to the stent 10, the skirt portion 103 may be sewn to the annular collar 40 as well as other parts of the stent structure. The prosthetic heart valve 100 may be tubular with a substantially circular cross-section.

On the other hand, it is conceivable to mount the prosthetic heart valve 100 to the outer surface of a support stent 1. That is, the skirt portion 102 could be in direct contact with the diseased native heart valve and could be attached to the stent 10 by means of sutures. Mounting the prosthetic heart valve 100 to the outer surface of the stent 10 supports the load transfer from the leaflet 102 to the stent 1. This greatly reduces stresses on the leaflets 102 during closing and consequently improves the durability thereof. Also, it is possible to design the valve to obtain improved hemodynamics in the case of mounting the skirt portion and commissures to the outer surface of the stent. Additionally, the heart valve material which is in direct contact with the diseased native heart valve provides a good interface for sealing against leakage (i.e., paravalvular leakage), tissue in-growth and attachment.

The material for the prosthetic heart valve 100 and, in particular the material for the leaflets 102 of the prosthetic heart valve 100 can be made from synthetics, animal valves or other animal tissues such as pericardium. The animal tissues can be from a number of types of animals. Preferably, the leaflet material of the prosthetic heart valve 100 is from either bovine or porcine pericardium, but other animals can also be considered, for example equine, kangaroo, etc.

Reference is made in the following to FIGS. 12 to 17 for describing exemplary embodiments of reinforcement elements 107.1 to 107.8 which may be utilized in the endoprosthesis 1 according to the present disclosure. The reinforcement elements 107.1 to 107.8 may reduce the stress concentration in the tissue material of the prosthetic heart valve 100 at the connection between the bendable transition area 104 and the lower leaflet attachment region 11*c* (FIGS. 12 to 14) and/or the commissure attachment regions 11*b* (FIGS. 15 to 17) of the stent 10.

The reinforcement elements 107.1 to 107.8 can be at discrete locations or continuously along the path of the stitching. For example, they can be placed opposite to the retaining arches of the stent on the other side of the prosthetic heart valve material. The depicted reinforcement elements 107.1 to 107.8 are applied in order to strengthen the attachment to the stent and reduce stress concentrations in the leaflet material that would occur by suturing directly to the bendable transition portion 104 or leaflet support portion 103 respectively. Further to this, the reinforcement elements 107.1 to 107.8 may avoid direct contact between knots of the sutures and the tissue of the prosthetic heart valve. Also, direct contact between the heart valve tissue and the stent structure or any other metallic component of the endoprosthesis can be avoided by the reinforcement elements.

The reinforcement elements 107.1 to 107.8 are preferably designed with rounded edges to avoid abrasion of the valve tissue during opening and closing of the prosthetic heart valve 100.

Figure 11A:
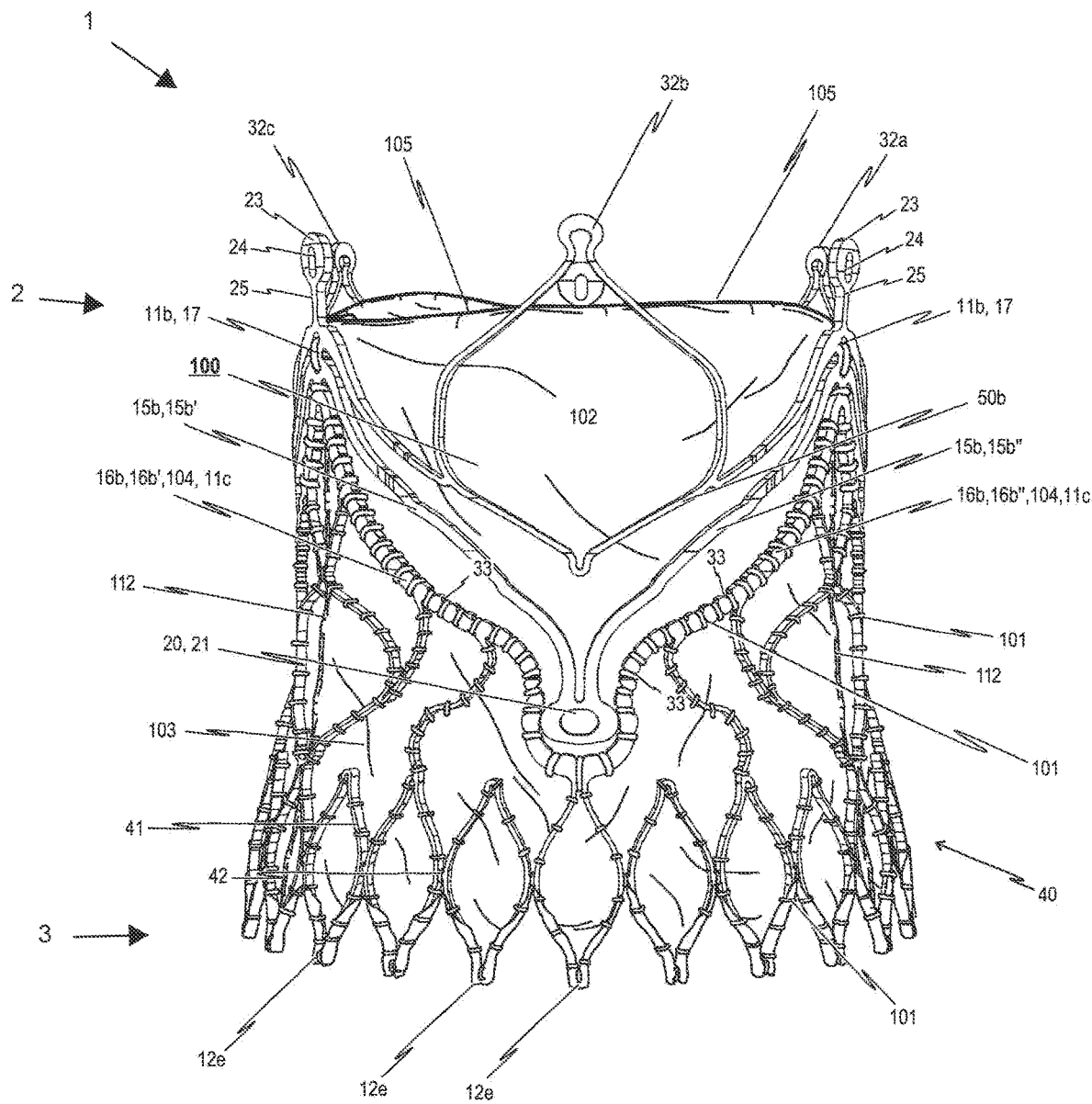
FIG. 11a a first perspective side view of an endoprosthesis for treating a narrowed cardiac valve or a cardiac valve insufficiency, where the endoprosthesis is shown in an expanded state and where the endoprosthesis comprises a cardiac valve stent and a prosthetic heart valve according to an exemplary embodiment of the disclosure, said cardiac valve stent is used for holding the prosthetic heart valve.
Figure 11B:
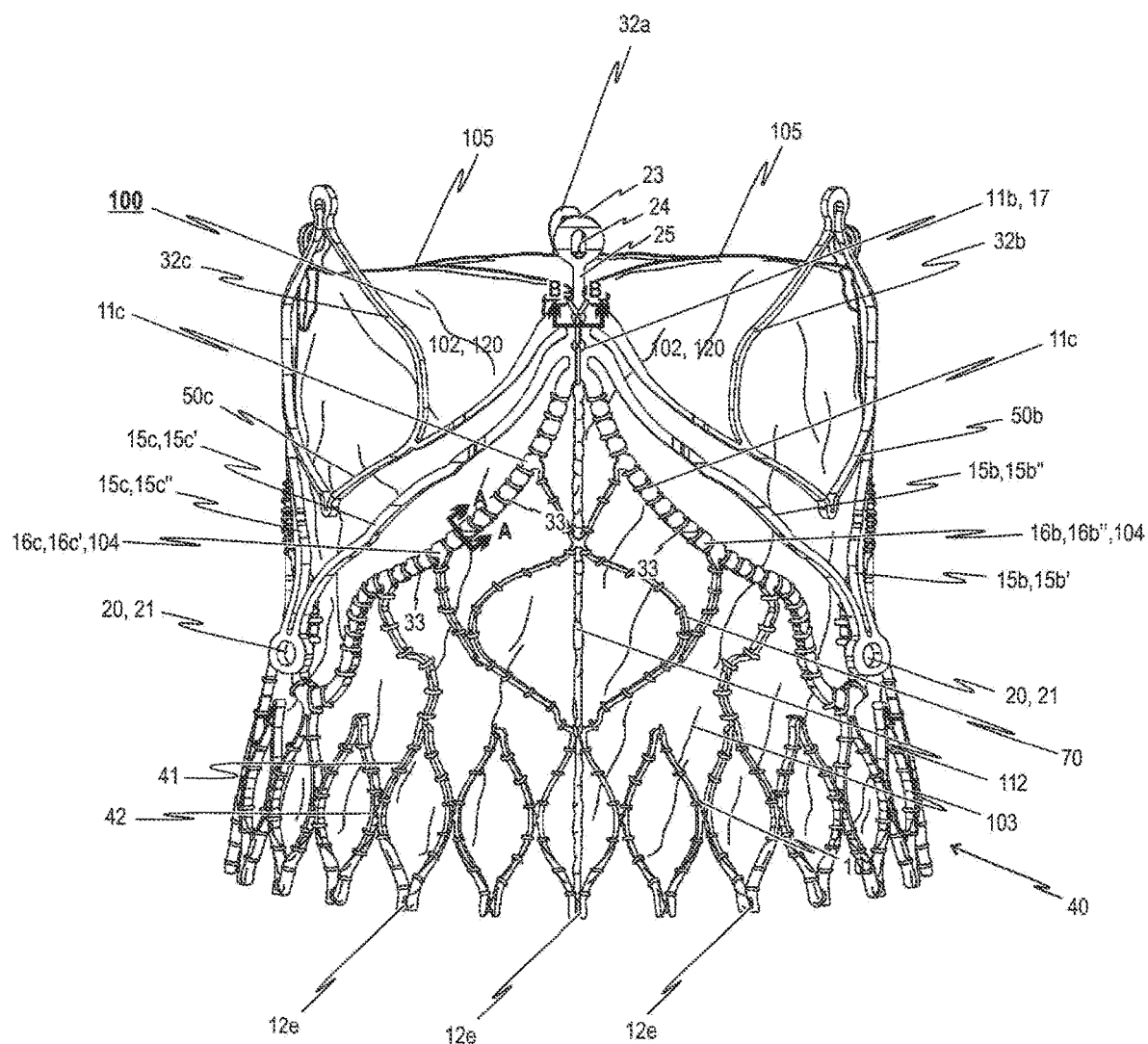
FIG. 11b a second perspective side view of the endoprosthesis depicted in FIG. 11a, where the endoprosthesis is shown in an expanded state and where the endoprosthesis comprises a cardiac valve stent and a prosthetic heart valve according to an exemplary embodiment of the disclosure, said cardiac valve stent is used for holding the prosthetic heart valve.
Figure 12:
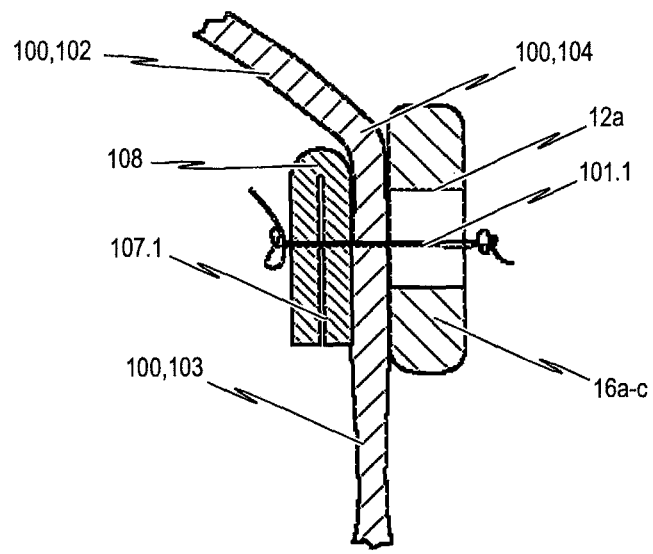
FIG. 12 a cross sectional view along the line A-A shown in FIG. 6b or 11b showing a first exemplary embodiment of reinforcement elements which may be utilized in the endoprosthesis according to the present disclosure for fixing a prosthetic heart valve to a cardiac valve stent.

In more detail, FIG. 12 shows a cross sectional view along the line A-A in FIG. 6b or FIG. 11b respectively, i.e. a cross sectional view of one retaining arch 16a, 16b, 16c of the stent 10 utilized in an endoprosthesis 1 of the present disclosure. As depicted in FIG. 12, a first exemplary embodiment of reinforcement elements 107.1 may be utilized for fixing the prosthetic heart valve 100 to the stent 10.

According to this exemplary embodiment, the connection of the prosthetic heart valve tissue to the stent 10 is reinforced by means of at least one reinforcement element in the form of a inner cushion 107.1 which is intended to reduce stress concentrations in the tissue material of the prosthetic heart valve 100, said that stress concentrations may occur from direct stitching in the tissue material of the prosthetic heart valve 100. The at least one reinforcement element in the form of the inner cushion 107.1 is placed between a suture 101.1 and the tissue material of the prosthetic heart valve 100. In this respect, any stress caused by the suture 101.1 is distributed over a larger area of the tissue material of the prosthetic heart valve 100. The at least one reinforcement element in the form of the inner cushion 107.1 is placed opposite to the corresponding retaining arch 16a, 16b, 16c of the stent 10 on the other side of the tissue material of the prosthetic heart valve 100. That is, the at least one reinforcement element in the form of the inner cushion 107.1 is mounted to the inner surface of the bendable transition area 104 of the prosthetic heart valve 100. The at least one inner cushion 107.1 representing a first embodiment of the reinforcement elements may be folded in such a way that at least one round edge 108 is formed. This at least one round edge 108 is designed to avoid abrasion of tissue material of the leaflets 102 during opening and closing of the prosthetic heart valve 100.

The reinforcement element in the form of the inner cushion 107.1 may be made of one or multiple layer materials, consisting of materials like polyester velour, PTFE, pericardial tissue, or any other material suitable for forming round edges, distributing or buffering stresses in the tissue material of the prosthetic heart valve 100. The reinforcement element in the form of the inner cushion 107.1 can be applied to span across the gap formed between the lower end of two neighbouring arms 16a', 16a"; 16b', 16b"; 16c', 16c" of one retaining arches 16a, 16b, 16c (see FIG. 6a) for supporting the tissue material of the prosthetic heart valve 100 across the gap.

Figure 15:
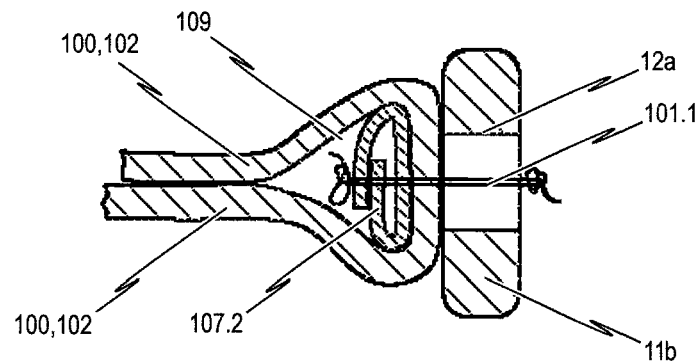
FIG. 15 a cross sectional view along the line B-B shown in FIG. 6b or 11b for explaining a fourth exemplary embodiment of reinforcement elements which may be utilized in the endoprosthesis according to the present disclosure for fixing a prosthetic heart valve to a cardiac valve stent.

Reference is further made to FIG. 15, which is a cross sectional view along the line B-B (commissure attachment region 11b) shown in FIG. 6b or 11b for explaining a second exemplary embodiment of the reinforcement elements which may be utilized in the transcatheter delivered endoprosthesis 1 of the present disclosure, for fixing a prosthetic heart valve 100 to a cardiac valve stent 10.

Again, the reinforcement element may be made of one or multiple layer materials and consisting of materials like polyester velour, PTFE, pericardial tissue or any other material suitable for forming round edges. As shown in FIG. 15, at the upper end section of the prosthetic heart valve 100, the tissue material of the prosthetic heart valve 100 may be attached to the commissure attachment region 11b in such a manner that when the leaflets 102 are folded together, during closure of the heart valve, a small cavity 109 is created. Inside this cavity 109, a reinforcement element in the form of an inner cushion 107.2 is inserted. It has to be noted that the cavity 109 is formed, so as to be as small as possible in order to avoid leakage during the closing phase of the heart valve prosthesis 1.

Figure 13:
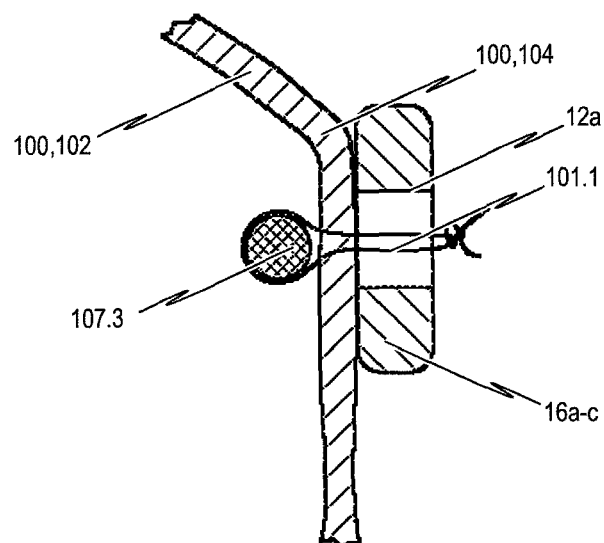
FIG. 13 a cross sectional view along the line A-A shown in FIG. 6b or 11b showing a second exemplary embodiment of reinforcement elements which may be utilized in the endoprosthesis according to the present disclosure for fixing a prosthetic heart valve to a cardiac valve stent.

FIG. 13 is a cross sectional view along the line A-A shown in FIG. 6b or 11b for explaining a third exemplary embodiment of reinforcement elements which may be utilized in the endoprosthesis 1 according the present disclosure. According to this exemplary embodiment, the reinforcement element may consist of a wire rail 107.3 which is substantially at the same place as the reinforcement elements consisting of an inner cushion 107.1 illustrated in FIG. 12. In this case, the sutures 101.1 are coiled around the wire rail 107.3 on the inner surface of the prosthetic heart valve 100, whilst on the outer surface of the biological prosthetic heart valve, the sutures 101.1 are attached to a retaining arch 16a, 16b, 16c by means of a suitable stitch pattern. That is, the wire rail 107.3 is mounted to the inner surface of the bendable transition area 104 of the prosthetic heart valve. The wire rail 107.3 is preferably made of Nitinol, thus allowing for the wire rail 107.3 to collapse together with the stent 10. Again, the reinforcement element of the third embodiment is designed with rounded edges to avoid abrasion of the leaflet tissue during opening and closing of the prosthetic heart valve 100.

Figure 14:
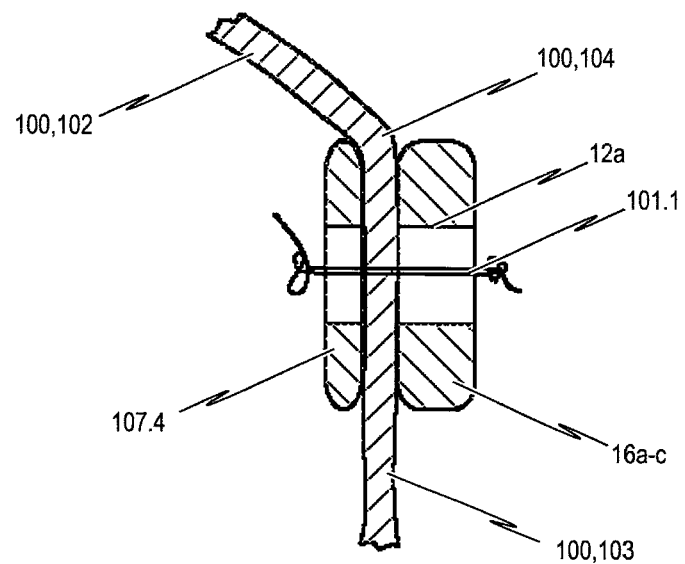
FIG. 14 a cross sectional view along the line A-A shown in FIG. 6b or 11b showing a third exemplary embodiment of reinforcement elements which may be utilized in the endoprosthesis according to the present disclosure for fixing a prosthetic heart valve to a cardiac valve stent.

FIG. 14 is a cross sectional view along the line A-A shown in FIG. 6b or 11b for explaining a fourth exemplary embodiment of reinforcement elements which may be utilized in the endoprosthesis 1 according to the present disclosure. Hence, instead of using inner cushions 107.1, 107.2 which consist of materials like polyester velour or PTFE, the reinforcement element, according to the fourth exemplary embodiment, can be arranged as essential copies of the retaining arches 16a, 16b, 16c. In this embodiment, however, the reinforcement element is an inner attachment rail 107.4 which is thinner than a corresponding retaining arch 16a, 16b, 16c since a thick material would inhibit the endoprosthesis 1 from being collapsed to a small size. In particular, the inner attachment rail 107.4 has the same fastening holes 12a and notches longitudinally distributed at given locations as the corresponding retaining arch 16a, 16b, 16c.

Moreover, the inner attachment rail 107.4 is placed on the inner surface of the tissue material of the prosthetic heart valve 100, opposite to the retaining arches 16a, 16b, 16c. Thus the prosthetic heart valve 100 is clamped in between the retaining arches 16a, 16b, 16c and the inner attachment rail 107.4, wherein the retaining arches 16a, 16b, 16c and the inner attachment rail 107.4 are connected by means of sutures 101.1.

In an alternative embodiment, however, the connection between retaining arches 16 and the inner attachment rail 107.4 may utilize rivets, welding or soldering, so as to clamp the biological prosthetic heart valve tissue without penetrating it with needles or suture. In turn, it is preferable, that the inner attachment rail 107.4 may be made of Nitinol, in order to allow simultaneously collapsing with the stent 10.

Of course, the edges of the inner attachment rail 107.4 may be rounded in order to prevent abrasion of the leaflets 102. In addition, the inner attachment rail 107.4 could be wrapped in tissue or synthetic material to further reduce the potential wear during the contact with the leaflet material upon the heart valve operation.

Figure 16:
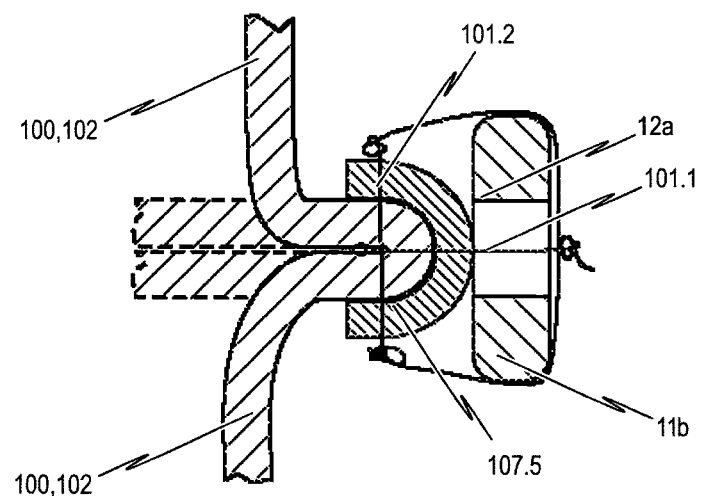
FIG. 16 a cross sectional view along the line B-B shown in FIG. 6b or 11b showing a fifth exemplary embodiment of reinforcement elements which may be utilized in the endoprosthesis according to the present disclosure for fixing a prosthetic heart valve to a cardiac valve stent.

FIG. 16 shows a cross sectional view along the line B-B shown in FIG. 6b or 11b for explaining a fifth exemplary embodiment of reinforcement elements which may be utilized in the endoprosthesis 1 of the present disclosure.

As depicted in FIG. 16, the reinforcement element according to this exemplary embodiment is an outer wrapping element 107.5 attached to the back side of the prosthetic heart valve tissue, at the commissure attachment region 11b of the stent 10. The leaflets 102 are folded without forming a cavity. Rather, the outer wrapping element 107.5 is clamped on the outer surface of the biological prosthetic heart valve 100, more particularly to the outer surface of the bendable transition area 104, pressing the leaflets 102 together. Thereby, a strengthened region is created by folding the prosthetic heart valve tissue and wrapping it with the outer wrapping element 107.5.

The outer wrapping element 107.5 is attached the commissure attachment region 11b by means of sutures 101.1. Additional lateral sutures 101.2 are provided to press the outer wrapping element 107.5 onto the outer surface of the bendable transition area 104 of the prosthetic heart valve 100.

The outer wrapping element 107.5 is preferably made of a polymer material such as PTFE, PET fabric or sheet or a piece of pericardial tissue. However, it could also be a more rigid u-shaped clip or bendable material that can pinch the folded tissue material of the prosthetic heart valve 100 without the use of additional lateral sutures 101.2. In addition, this outer wrapping element 107.5 acts as a bumper to limit the opening of the leaflets 102 in order to prevent them from hitting stent 10.

The dashed lines in FIG. 16 represent the closed position of the leaflets 102.

Figure 18:
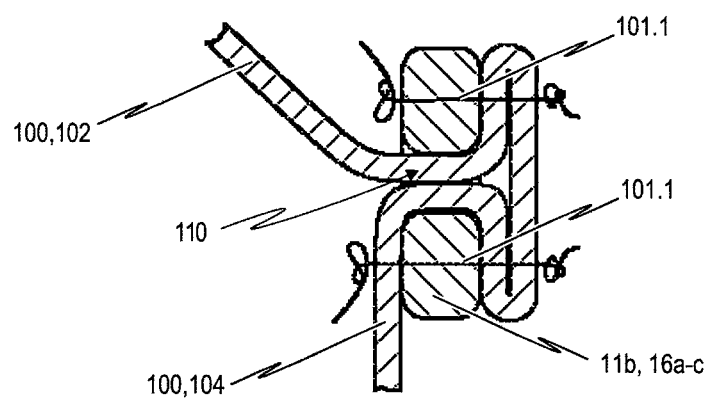
FIG. 18 a cross sectional view along the line B-B shown in FIG. 6b or 11b showing an alternative attachment solution for fixing a prosthetic heart valve to a cardiac valve stent.

FIG. 18 shows an alternative attachment solution where the prosthetic heart valve 100 is mounted to the stent 10 from the outside. For this purpose, the tissue material of the prosthetic heart valve 100 is folded and passes through slots 110 provided in the retaining arches 16a, 16b, 16c. The edges of the slots 110 are preferably rounded and smooth to avoid abrading or wearing the tissue material of the prosthetic heart valve 100. Furthermore, to further reduce wear of the tissue, the slots 110 could be wrapped in thin pericardial tissue. In this design, there is some material thickness on the outside of the stent 10, which could impinge on the anchoring of the stent 10 at the position of the diseased natural prosthetic heart valve.

One embodiment might include thinning the retaining arches 16a, 16b, 16c on the outer surface relative to the rest of the stent structure, to accommodate the tissue material on the outside surface. This would also allow for a recess when the stent 10 is compressed so that the collapsed prosthesis does not require a larger delivery catheter.

Figure 17:
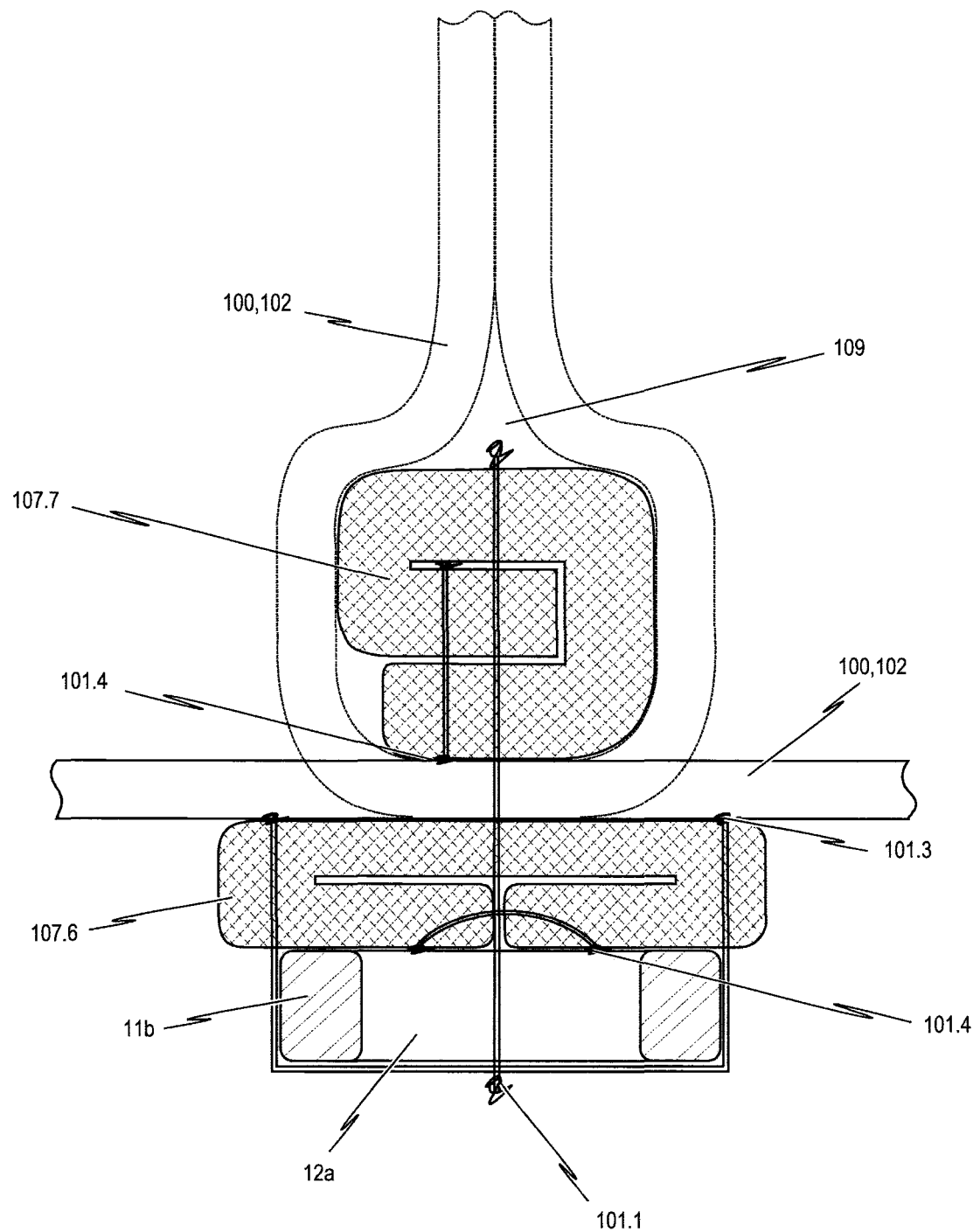
FIG. 17 a cross sectional view along the line B-B shown in FIG. 6b or 11b showing a sixth exemplary embodiment of reinforcement elements which may be utilized in the endoprosthesis according to the present disclosure for fixing a prosthetic heart valve to a cardiac valve stent.

FIG. 17 is a cross sectional view along the line B-B depicted in FIG. 6b or 11b showing a sixth exemplary embodiment of reinforcement elements 107.6, 107.7 which may be utilized in the endoprosthesis according present disclosure.

In detail, FIG. 17 shows an embodiment where reinforcement elements 107.6 and 107.7 are attached to the inner surface and the outer surface of the transition area 104 of the prosthetic heart valve 100. Although FIG. 17 only shows a cross sectional view along the line B-B, it should be noted that the depicted sixth embodiment of the reinforcement elements may also be applied along the retaining arches 16a, 16b, 16c (line A-A) of the stent. In this regard, the outer reinforcement element 107.6 may consist of a wide strip of 200 µm thick porcine pericardium that is long enough to cover the entire length of the retaining arches 16a, 16b, 16c (lower leaflet attachment region 11c) and the commissure attachment region 11b. This strip of pericardium which forms the outer reinforcement element 107.6 can be cut into three short segments of about 5 mm each to match the length of the commissure attachment region 11b and three long segments of about 45 mm each to match the length along the retaining arches 16a, 16b, 16c (lower leaflet attachment region 11c) from one commissure attachment region 11b to the adjacent.

The 4 mm wide porcine pericardium outer reinforcement element 107.6 may be folded in half and sutured using a fine clinging suture 101.4 (e.g. a 8-0 suture) with a running stitch very close to the free edges. The sutured outer reinforcement element 107.6 is then placed along the inner surface of the retaining arches 16a, 16b, 16c and/or the commissure attachment region lib with a 8-0 running stitch placed along the stent surface. The outer reinforcement element 107.6 is sutured to the stent to line the inner surface using 6-0 surrounding sutures 101.3 and zig-zag crossing stitches that wrap around the commissure attachment region 11b and/or the retaining arches 16a, 16b, 16c (not through the eyelets).

With regards to the inner reinforcement element 107.7, the material is preferably a strip of 200 µm porcine pericardium, which is about 3.5 mm wide and cut and overlapped or rolled to three layers. The length of the piece of tissue depends on whether only the commissure attachment region 11b or the retaining arches 16a, 16b, 16c are reinforced. For only the commissure attachment region 11b, three short segments of about 5 mm are needed. The strip is held in the overlapped or rolled shape by clinging sutures 101.4 with an 8-0 running stitch. The inner reinforcement element 107.7 may be constructed such as to exhibit minimal size to avoid causing too big of a cavity 109 in between the leaflets 102 during closure of the prosthetic heart valve 100. The inner reinforcement element 107.7 is secured on the inner surface of the bendable transition area 104 of the prosthetic heart valve 100 and to the stent 10 through the eyelets 12a. Preferably, 4-0 sutures 101.1 with a locking stitch on the outer diameter are used for this purpose. These sutures 101.1 are the most critical in the assembly and need to be very tight with no slack and locking. Instead of a single 4-0 suture 101.1, it is contemplated that two 6-0 sutures for redundancy and similar overall total strength are used. Furthermore, the 4-0 sutures 101.1 hold the outer reinforcement element 107.6 in place.

When opening and closing the leaflets 102 of the prosthetic heart valve 100, the outer reinforcement element 107.6 acts as a bumper to absorb shocks which affect the leaflets 102 during opening. In turn, the inner reinforcement element 107.7 spreads out the compressive forces induced by the sutures 101.1, thus avoiding stress concentration at the transition area 104 of the prosthetic heart valve 100.

Figure 7A:
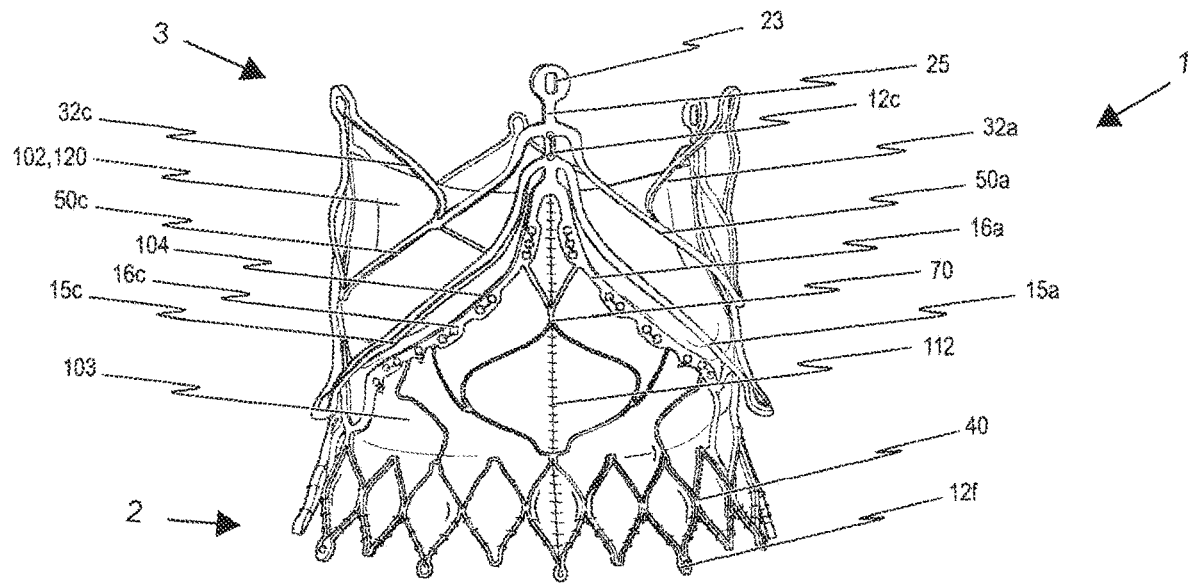
FIG. 7a a first perspective side view of an endoprosthesis for treating a narrowed cardiac valve or a cardiac valve insufficiency, where the endoprosthesis is shown in an expanded state and where the endoprosthesis comprises a cardiac valve stent and a prosthetic heart valve according to an exemplary embodiment of the disclosure, said cardiac valve stent is used for holding the prosthetic heart valve.
Figure 7B:
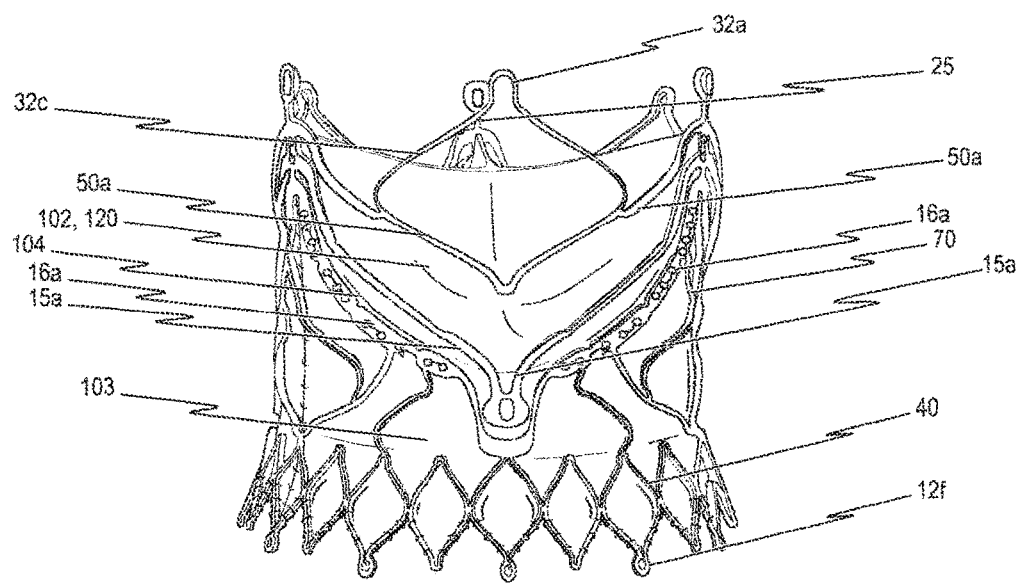
FIG. 7b a second perspective side view of the endoprosthesis depicted in FIG. 7a, where the endoprosthesis is shown in an expanded state and where the endoprosthesis comprises a cardiac valve stent and a prosthetic heart valve according to an exemplary embodiment of the disclosure, said cardiac valve stent is used for holding the prosthetic heart valve.

In the following, reference is made to FIGS. 7a, b for describing a further exemplary embodiment of a cardiac valve stent capable of supporting and anchoring a prosthetic heart valve. In detail, FIG. 7a shows a first perspective side view of a transcatheter delivered endoprosthesis 1 for treating a narrowed cardiac valve or a cardiac valve insufficiency, where the endoprosthesis 1 comprises a cardiac valve stent 10 according to the first exemplary embodiment of the stent (FIGS. 5a-e) for holding a prosthetic heart valve. FIG. 7b shows a second perspective side view of the endoprosthesis 1 depicted in FIG. 7a.

In contrast to the exemplary embodiment shown in FIGS. 6a and 6b, the endoprosthesis depicted in FIGS. 7a, b shows the prosthetic heart valve 100 according to the second valve embodiment. That is, the prosthetic heart valve 100 attached to the stent 10 of FIGS. 7a, b consists of three separate pieces 120 being sewn together along their contiguous edges 112. These three separate pieces 120 may either be cut from a single pericardial sack (xenograft or homograft) or from a plurality of pericardial sacks.

The endoprosthesis 1 according to the exemplary embodiment illustrated by FIGS. 7a and 7b comprises a stent 10 according to the first stent embodiment depicted by FIGS. 5a to 5e. This stent 10 comprises a plurality of positioning arches 15a, 15b, 15c configured to be positioned within a plurality of pockets of the patient's native heart valve and positioned on a first side of a plurality of native heart valve leaflets, and a plurality of retaining arches 16a, 16b, 16c configured to be positioned on a second side of the plurality of native heart valve leaflets opposite the first side, wherein furthermore a plurality of leaflet guard arches 50a, 50b, 50c are provided, each interspaced between the two arms 15a', 15a", 15b', 15b", 15c', 15c" of one of the plurality of positioning arches 15a, 15b, 15c. In addition, the respective arms 16a', 16a", 16b', 16b", 16c', 16c" of the retaining arches 16a, 16b, 16c are preferably provided with a plurality of bending edges 33 in order to divide each arm 16a', 16a", 16b', 16b", 16c', 16c" into a plurality of arm segments, wherein the structure of the stent 10 is programmed such that the respective arms 16a', 16a", 16b', 16b", 16c', 16c" of the retaining arches 16a, 16b, 16c have a curved shape at least in the expanded state of the stent 10. In particular, the shape of the respective arms 16a', 16a", 16b', 16b", 16c', 16c" of the retaining arches 16a, 16b, 16c shall be such defined that the arms follow the shape of the leaflets 102 of a prosthetic heart valve 100 to be affixed to the stent 10.

In the structure of the stent 10 according to the embodiment depicted in FIGS. 7a and 7b, one leaflet guard arch 50a, 50b, 50c is provided in between each positioning arch 15a, 15b, 15c. Hence, one leaflet guard arch 50a, 50b, 50c is allocated to each positioning arch 15a, 15b, 15c.

Each leaflet guard arch 50a, 50b, 50c has a substantially U-shaped or V-shaped structure which is closed to the lower end 2 of the stent 10. In particular, each leaflet guard arch 50a, 50b, 50c has a shape that is roughly similar to the shape of the positioning arch 15a, 15b, 15c and each leaflet guard arch 50a, 50b, 50c is arranged within the arms of the corresponding positioning arch 15a, 15b, 15c. Furthermore, each of the leaflet guard arches 50a, 50b, 50c extends in the same direction as the positioning arch 15a, 15b, 15c.

The leaflet guard arches 50a, 50b, 50c are preferably programmed so that they extend in a radial direction outside the circumference of the stent 10 when the stent 10 is in its expanded state. In this way, an increased contact force can be applied to the leaflets of the native (diseased) cardiac valve when the stent 10 is in its expanded and implanted state. This, in turn, allows an increased security in the fixing of the stent 10 in situ.

When the stent 10 is in its expanded and implanted state, the leaflet guard arches 50a, 50b, 50c actively keep the diseased leaflets, i.e. the leaflets of the native cardiac valve, from impinging the leaflets 102 of a prosthetic heart valve 100 attached to the stent 10, when the positioning arches 15a, 15b, 15c are placed outside the native leaflets. In addition, the leaflet guard arches 50a, 50b, 50c may also provide additional anchoring and securing against migration.

An alternative embodiment of a stent 10 is shown in FIGS. 8a-d (hereinafter also named "second stent embodiment"). The stent 10 according to the embodiment depicted in FIGS. 8a-d essentially comprises the same features as the stent described with reference to FIGS. 5a-e. In particular, the stent 10 also comprises positioning arches 15a, 15b, 15c as well as retaining arches 16a, 16b, 16c and an annular collar 40.

In contrast to the first embodiment of a stent 10 depicted in FIGS. 5a-e, the stent 10 of the second stent embodiment comprises retaining arches 16a, 16b, 16c which are not provided with a number of lower leaflet attachment regions 11c, each having a number of additional fastening holes 12a or eyelets provided for fastening the tissue components of a prosthetic heart valve 100. Rather, the stent of the second stent embodiment is provided with retaining arches 16a, 16b, 16c whose arms 16a', 16a", 16b', 16b", 16c', 16c" are segmented by a plurality of bending edges 33 which are not only used for defining a bending point of two neighboring arm segments, but also as fastening notches which can be used for fixing the prosthetic heart valve prosthesis 100 to the stent 10. It is conceivable, of course, that the fastening notches are adapted to the thickness of the suture, thread or wire. In particular, the additional notches may be radiused to minimize damage to the suture, thread or wire. Due to the increased number of bending edges 33 providing fastening notches along the retaining arches 16a, 16b, 16c, the retaining arches 16a, 16b, 16c allow for more continuous bending along the entire length of their respective arms 16a', 16a", 16b', 16b", 16c', 16c", simplifying the attachment of said retaining arches 16a, 16b, 16c to the bendable transition area 104 of the prosthetic heart valve 100.

Figure 8A:
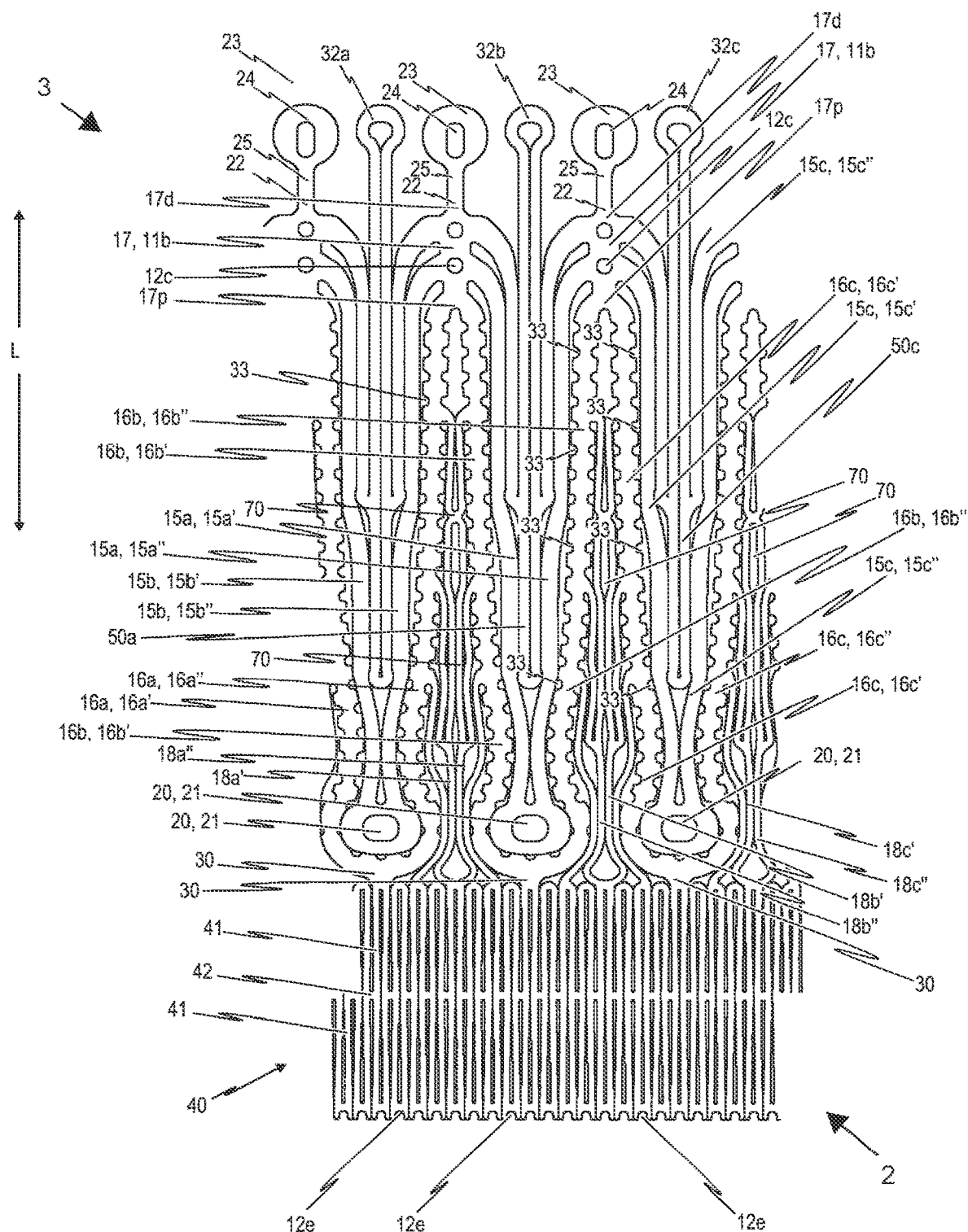
FIG. 8a a flat roll-out view of an exemplary embodiment of a second cardiac valve stent, in its compressed state, which may be used in the endoprosthesis according to FIG. 11a or FIG. 11b for fixing a prosthetic heart valve according to an exemplary embodiment of the disclosure.

In more detail, FIG. 8a shows a flat roll-out view of a cardiac valve stent 10 pursuant the second embodiment of the stent 10, whereby the stent 10 is in its non-expanded state. This flat roll-out view corresponds to a two-dimensional projection of a cutting pattern which can be used in the manufacture of the stent 10 pursuant the second embodiment. This enables a one-piece stent 10 to be cut from a portion of tube, in particular a metal tube.

Figure 8B:
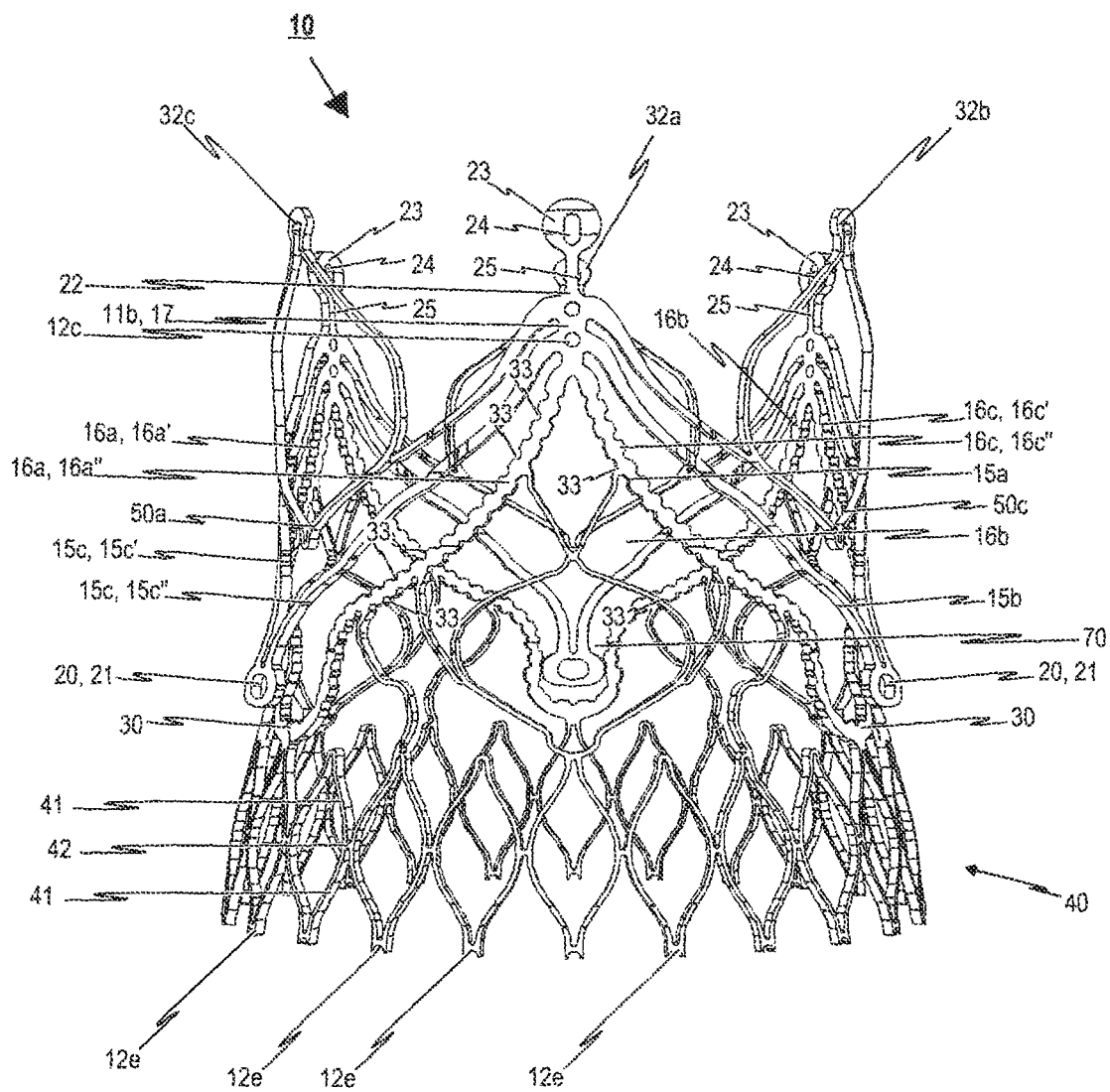
FIG. 8b a first perspective side view of the second cardiac valve stent capable of supporting and anchoring a prosthetic heart valve according to an exemplary embodiment of the disclosure, whereby the cardiac valve stent is shown in its expanded state.
Figure 8C:
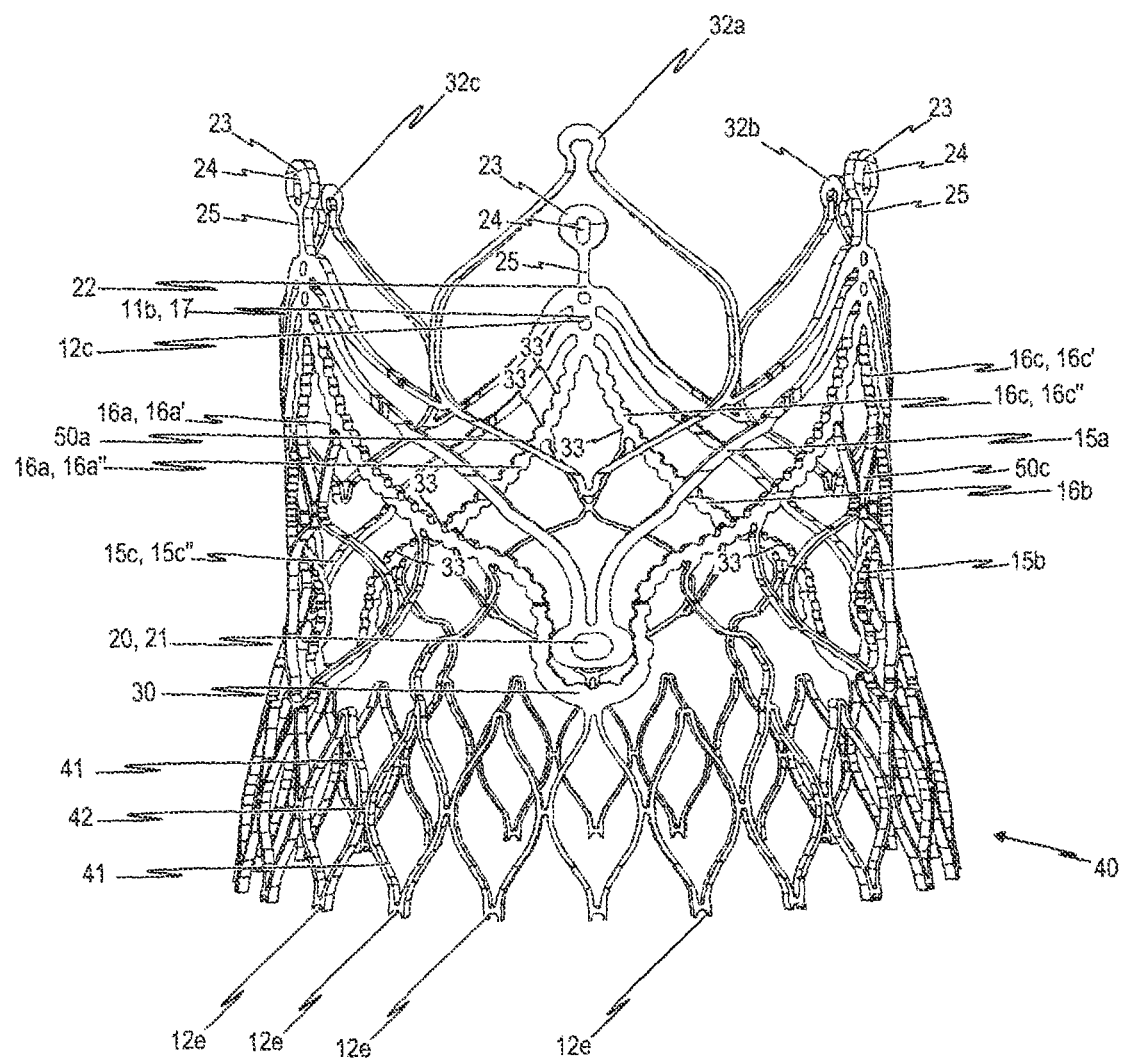
FIG. 8c a second perspective side view of the second cardiac valve stent capable of supporting and anchoring a prosthetic heart valve according to an exemplary embodiment of the disclosure, whereby the cardiac valve stent is shown in its expanded state.

FIG. 8b shows a first perspective side view of a cardiac valve stent 10 according to the second stent embodiment, whereby the cardiac valve stent 10 is shown in its expanded state, and FIG. 8c shows a second perspective side view the stent 10 according to the second stent embodiment, whereby the cardiac valve stent is also shown in its expanded state.

Figure 8D:
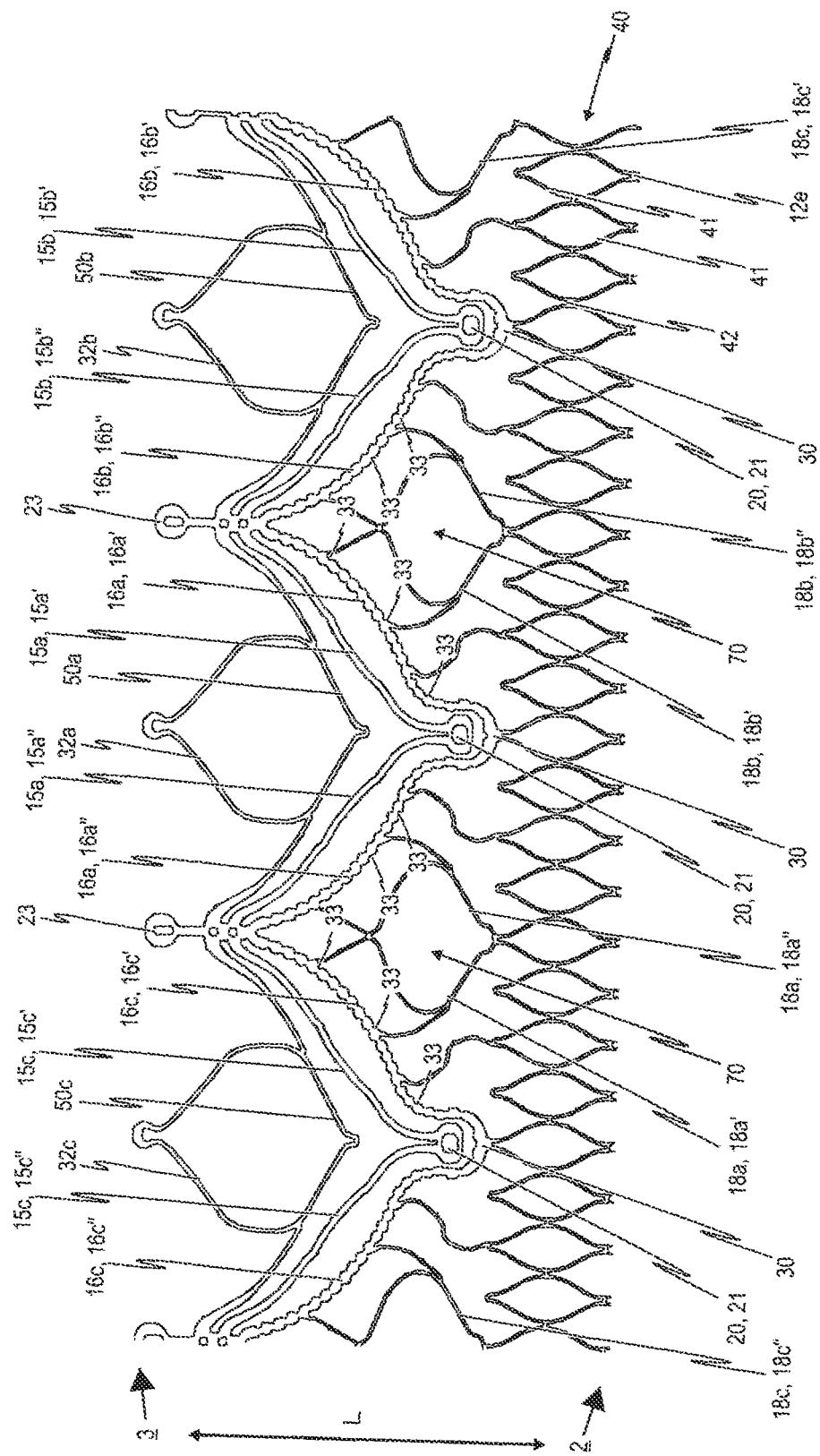
FIG. 8d a second flat roll-out view of an exemplary embodiment of a second cardiac valve stent, in its expanded state, which may be used in the endoprosthesis according to FIG. 11a or FIG. 11b for fixing a prosthetic heart valve according to an exemplary embodiment of the disclosure.

FIG. 8d shows a flat roll-out view of a cardiac valve stent 10 according to the second embodiment of the stent. Contrary to the flat roll-out view depicted in FIG. 8a, however, the flat roll-out view according to FIG. 8d shows the cardiac valve stent 10 is in its expanded state.

Thus, the stent 10 according to the second stent embodiment comprises a plurality of positioning arches 15a, 15b, 15c and a plurality of retaining arches 16a, 16b, 16c. Each of the plurality of positioning arches 15a, 15b, 15c is configured to be positioned within a plurality of pockets of the patient's native heart valve and positioned on a first side of a plurality of native heart valve leaflets. On the other hand, each of the plurality of retaining arches 16a, 16b, 16c is configured to be positioned on a second side of the plurality of native heart valve leaflets opposite the first side.

Furthermore, a plurality of leaflet guard arches 50a, 50b, 50c are provided, each interspaced between the two arms 15a', 15a", 15b', 15b", 15c', 15c" of one of the plurality of positioning arches 15a, 15b, 15c. In addition, the respective arms 16a', 16a", 16b', 16b", 16c', 16c" of the retaining arches 16a, 16b, 16c are preferably provided with a plurality of bending edges 33 in order to divide each arm 16a', 16a", 16b', 16b", 16c', 16c" into a plurality of arm segments, wherein the structure of the stent 10 is programmed such that the respective arms 16a', 16a", 16b', 16b", 16c', 16c" of the retaining arches 16a, 16b, 16c have a curved shape at least in the expanded state of the stent 10. In particular, the shape of the respective arms 16a', 16a", 16b', 16b", 16c', 16c" of the retaining arches 16a, 16b, 16c shall be such defined that the arms follow the shape of the bendable transition area 104 of the prosthetic heart valve 100 to be affixed to the stent 10.

In detail and as depicted in the flat roll-out view shown in FIG. 8a, the respective arms 16a', 16a", 16b', 16b", 16c', 16c" of the retaining arches 16a, 16b, 16c are provided with a plurality of bending edges 33. These bending edges 33 may be uniformly distributed along the length of each retaining arch arm 16a', 16a", 16b', 16b", 16c', 16c" thereby dividing each arm 16a', 16a", 16b', 16b", 16c', 16c" into a plurality of arm segments. The arm segments of a corresponding retaining arch arm 16a', 16a", 16b', 16b", 16c', 16c" are interconnected thereby constituting a retaining arch arm which describes an essentially straight line in the not-expanded state of the stent 10. In this regard, reference is made to the flat roll-out view depicted in FIG. 8a which shows the uncurved configuration of the respective arms 16a', 16a", 16b', 16b", 16c', 16c" of the retaining arches 16a, 16b, 16c.

When manufacturing the stent 10, the stent structure and in particular the structure of the retaining arches 16a, 16b, 16c is programmed such that the respective retaining arch arms 16a', 16a", 16b', 16b", 16c', 16c" have a curved shape in the expanded state of the stent 10. The shape of the respective retaining arch arms 16a', 16a", 16b', 16b", 16c', 16c" is such defined that the arms follow the shape of the leaflets of a prosthetic heart valve 100 to be affixed to the stent 10 (cf. FIG. 8d).

Hence, the respective retaining arch arms 16a', 16a", 16b', 16b", 16c', 16c", onto which the prosthetic heart valve 100 is sewn or sewable, will change their shape when the stent 10 expands, wherein the retaining arches 16a, 16b, 16c are curved in the expanded state of the stent 10, but relatively straight when the stent 10 is collapsed. Thus, when in the expanded state, the retaining arches 16a, 16b, 16c of the stent 10 are adapted to fit to the shape of the bendable transition area 104 of the prosthetic heart valve 100. In detail, in their expanded state, the retaining arches 16a, 16b, 16c are adapted to progress in an essentially u-shaped manner, similar to the shape of a natural aortic or pulmonary heart valve, for reducing tissue stresses during the opening and closing motion of the leaflets 102.

As can be seen, for example, in FIG. 8d, the essentially u-shaped curvature of the respective retaining arch arms 16a', 16a", 16b', 16b", 16c', 16c" is achieved by segmenting the arms 16a', 16a", 16b', 16b", 16c', 16c". In detail, the arms 16a', 16a", 16b', 16b", 16c', 16c" are segmented by providing a plurality of bending edges 33. In the expanded state of the stent 10, two neighboring arm segments are angled relative to each other, wherein the bending point of these two neighboring arm segments is defined by the bending edge 33 which is provided in between neighboring arm segments. Hence, the greater the number of bending edges 33 provided in an arm 16a', 16a", 16b', 16b", 16c', 16c" of a retaining arch 16a, 16b, 16c, the greater the number of arm segments which may extend in different directions in the expanded state of the stent 10. In this respect, the shape of the respective retaining arch arms 16a', 16a", 16b', 16b", 16c', 16c" can be adapted to the shape of the leaflets 102 of the prosthetic heart valve 100 to be affixed to the stent 10.

According to the design of the second stent embodiment, the respective arms 16a', 16a", 16b', 16b", 16c', 16c" of the retaining arches 16a, 16b, 16c are not provided with fastening holes 12a, as it is the case, for example, in the first embodiment of the stent (FIGS. 5a to 5e). Rather, in the second stent embodiment, the bending edges 33 provided in the retaining arch arms 16a', 16a", 16b', 16b", 16c', 16c" are not only used for defining a bending point of two neighboring arm segments, but also as fastening notches which can be used for fixing a prosthetic heart valve 100 to the stent 10.

A comparison with, for example, the flat roll-out view pursuant to FIG. 5a (first stent embodiment) illustrates directly that the respective retaining arch arms 16a', 16a", 16b', 16b", 16c', 16c" of the stent design according to the second stent embodiment is at least partly much more thinner compared with the respective retaining arch arms of the first stent embodiment which are provided with lower leaflet attachment regions having fastening holes 12a. By reducing the width of the retaining arch arms 16a', 16a", 16b', 16b", 16c', 16c", the bendability of the arms is increased which allows a more precise adaptation of the shape of the respective retaining arch arms 16a', 16a", 16b', 16b", 16c', 16c" to the shape of the bendable transition area 104 of the prosthetic heart valve 100 to be affixed to the stent 10.

Moreover, by using the bending edges 33 provided in the retaining arch arms 16a', 16a", 16b', 16b", 16c', 16c" as fastening notches for fixing a heart valve prosthesis to the stent 10, a greater number of attachment points compared with the number of fastening holes 12a can be generated. In this regard, high stress concentrations at each single attachment point can be effectively avoided. Furthermore, the fastening notches provide space and allow for the sutures 101 to be protected during collapsing of the valve 100 into the catheter. Therefore, adjacent members of the stent 10 do not impinge on and damage the sutures 101 used to attach the prosthetic heart valve 100 to the retaining arches 16a, 16b, 16c, during collapsing and deployment of the prosthetic heart valve 100.

In addition, in the second embodiment of the stent, the attachment points (bending edges 33) to be used for fixing a heart valve prosthesis to the retaining arch arms 16a', 16a", 16b', 16b", 16c', 16c" of the stent 10 are more uniformly distributed along the respective retaining arch arms 16a', 16a", 16b', 16b", 16c', 16c", thereby providing a more uniform fixation of a heart valve prosthesis to the stent. Hence, the risk of an axial displacement of the heart valve prosthesis relative to the stent may be further reduced. Each individual bending edge 30 provided in the respective retaining arch arms 16a', 16a", 16b', 16b", 16c', 16c" thereby serves to guide a thread or thin wire with which the tissue component(s) of the prosthetic heart valve is affixed or sewn to the corresponding retaining arch arm 16a', 16a", 16b', 16b", 16c', 16c" of the stent 10. In detail, the means (thread or thin wire) provided for fastening the tissue component(s) of the prosthetic heart valve to the respective retaining arch arms 16a', 16a", 16b', 16b", 16c', 16c" is guided by way of the bending edge 33 acting as fastening notch so that a longitudinal displacement of the prosthetic heart valve relative to the stent 10 is substantially minimized. This also allows exact positioning of the prosthetic heart valve relative the stent 10.

In addition, the stent 10 according to the second stent embodiment may further include at least one auxiliary arch 18a, 18b, 18c interspaced between two adjacent retaining arches 16a, 16b, 16c, wherein the at least one auxiliary arch 18a, 18b, 18c includes a first arm 18a', 18b', 18c' connected at a first end thereof to a first retaining arch 16a, 16b, 16c and a second arm 18a'', 18b'', 18c'' connected at a first end thereof to a second retaining arch 16a, 16b, 16c, and wherein the first and second arms 18a', 18a'', 18b', 18b'', 18c', 18c'' of the at least one auxiliary arch 18a, 18b, 18c each include respective second ends connected to an annular collar 40 which is arranged at the lower end section of the stent body. As in the previously described stent design (first stent embodiment), this at least one collar 40 serves as an additional anchoring measure for a stent cut from a portion of a tube by using the cutting pattern depicted in FIG. 8a.

In detail, the respective first and second arms 18a', 18a'', 18b', 18b'', 18c', 18c'' of the at least one auxiliary arch 18a, 18b, 18c are part of a strut or web structure which is provided between the first and second arms 18a', 18a'', 18b', 18b'', 18c', 18c'' of two adjacent auxiliary arches 18a, 18b, 18c in order to support the prosthetic heart valve 100 to be affixed to the stent 10 (see, for example, FIGS. 11a and 11b). As can be seen, for example, from FIG. 8d the strut or web structure may be composed by a plurality of struts or strut-like members which are interconnected such as to form a reinforcement structure. Each strut or strut-like element of the reinforcement structure serves as reinforcement member in order to increase the strength or resistance to deformation of the area between the first and second arms 18a', 18a'', 18b', 18b'', 18c', 18c'' of two adjacent auxiliary arches 18a, 18b, 18c. The reinforcement structure thereby provides mechanical reinforcement to the stent 10. Moreover, the reinforcement members of the reinforcement structure between the first and second arms 18a', 18a'', 18b', 18b'', 18c', 18c'' of two adjacent auxiliary arches 18a, 18b, 18c provides for an additional support for the skirt portion 103 of a prosthetic heart valve 100 to be attached to the stent 10. In fact, it is conceivable to attach the skirt portion 103 of a prosthetic heart valve 100 directly to the auxiliary arches 18a, 18b, 18c by means of sutures, threads or thin wires, as will be explained in more detail with reference to FIGS. 11a and 11b below.

The terms "strength" or "resistance to deformation" as used herein may be used to denote any of a number of different properties associated with the reinforcement members. For example, the terms may be used to refer to properties of the material from which the reinforcement members are made, such as the yield strength, the modulus of elasticity, the modulus of rigidity, or the elongation percentage.

Similarly, the terms may be used to refer to the hardness of the reinforcement members. Hardness may be characterized as the "durometer" of the material, in reference to the apparatus used to measure the hardness of the material. The terms may also be used to denote geometric characteristics of the reinforcement members, such as the thickness of the reinforcement members. The terms "strength" or "resistance to deformation" may also be used to characterize any combination of the above properties as well as additional properties and/or characteristics.

The strength or resistance to deformation of the area between the first and second arms 18a', 18a'', 18b', 18b'', 18c', 18c'' of two adjacent auxiliary arches 18a, 18b, 18c can be increased in any number of ways. As can be seen from FIG. 8d, the strength or resistance to deformation of the area between the first and second arms 18a', 18a'', 18b', 18b'', 18c', 18c'' of two adjacent auxiliary arches 18a, 18b, 18c can be increased, for example, by providing a reinforcement structure formed by at least one, and preferably by a plurality of reinforcement elements (e.g. struts or strut-like members) which are interconnected to each other.

It is also conceivable that a reinforcement web is provided in order to increase the strength or resistance to deformation of the area between the first and second arms 18a', 18a'', 18b', 18b'', 18c', 18c'' of two adjacent auxiliary arches 18a, 18b, 18c. This reinforcement web may also be composed by a plurality of reinforcement elements (e.g. struts or strut-like members) which are interconnected to each other thereby forming a rhomboidal pattern.

The strength or resistance to deformation of the area between the first and second arms 18a', 18a'', 18b', 18b'', 18c', 18c'' of two adjacent auxiliary arches 18a, 18b, 18c can be increased, for example, by increasing the thickness of the reinforcement members, by eliminating stress concentration risers in the design of the stent 10, or by changing other aspects of the geometry of the reinforcement members. The strength can also be increased by changing the material properties of the stent 10 and/or the reinforcement members. For example, the reinforcement members can be made from a number of different materials, preferably shape memory materials, each having a different level of hardness. In this regard, it is conceivable to vary the stoichiometric composition of the material used for forming the stent and the reinforcement members such as to adapt the material properties of the stent 10 and/or the reinforcement members to the specific needs of each stent application. It is also conceivable to use different materials, for example nitinol and a shape-memory polymer, for forming the stent and the reinforcement members. In this manner, the selection of the reinforcement members can be tailored to the specific needs of each stent application. For example, in regions where a high external force is expected, reinforcement members having a high hardness may be preferred. The strength may also be increased by combining material properties with geometric changes.

As can be seen from FIG. 8d, the stent 10 according to the second stent embodiment is provided with a reinforcement structure which is constituted by a plurality of lattice cells 70 formed by a plurality of struts in the area between the arms 16a', 16a'', 16b', 16b'', 16c', 16c'' of two neighbouring (adjacent) retaining arches 16a, 16b, 16c, thereby providing for an additional support for the bendable transition area 104 of a prosthetic heart valve 100 to be attached to the stent 10.

In addition, this structure of the lattice cells 70 formed by a plurality of struts in the area between the adjacent arms of two neighbouring retaining arches 16a, 16b, 16c may provide uniform stent structure which may minimize blood leakage in the implanted stage of the stent 10 having a heart valve prosthesis attached thereto.

The upper end sections of the respective struts which are forming the structure of the lattice cells 70 are connected to the respective arms of the retaining arches 16a, 16b, 16c. Preferably, the upper end sections of the struts comprise a widened diameter in order to strengthen the connection between the upper end sections of the struts and the arms of the retaining arches 16a, 16b, 16c.

The already mentioned annular collar 40, which is provided at the lower end section of the stent body, is connected with the stent body via the retaining arches 16a, 16b, 16c on the one hand and the second ends of the respective arms 18a', 18a'', 18b', 18b'', 18c', 18c'' of the at least one auxiliary arch 18a, 18b, 18c on the other hand, wherein these arms 18a', 18a'', 18b', 18b'', 18c', 18c'' of the at least one auxiliary arch 18a, 18b, 18c are part of the structure of the lattice cells 70. In particular, the stent 10 according to the second embodiment is provided with an annular collar 40 which is shortened in its length by having only a single row of cells.

As can be seen from the flat roll-out view pursuant to FIG. 8a, the annular collar 40 at the lower end section of the stent body exhibits a plurality of supporting webs 41 which run parallel to the longitudinal axis L of the stent 10 in the non-expanded state of the stent 10 and are inter-connected by transversal webs 42. As can be seen from the two-dimensional roll-out view pursuant to FIG. 8c, however, in the expanded state of the stent 10, the supporting webs 41 and the transversal webs 42 forms a rhomboidal or serpentine-like annular collar 40 which abuts against the vascular wall in the implanted state of the stent 10.

In order to further improve securing of the position of an implanted and expanded endoprosthesis 1 and preventing antegrade migration, the stent 10 according to the second stent embodiment is provided with a flared or tapered section with a radius shape at its lower end section 2. In detail and as depicted in FIGS. 8b and 8c, in the expanded state of the stent 10, the lower end section of the annular collar 40 constitutes the flared or tapered section of the stent 10. As has been described before, the prosthetic heart valve 100 according to the present disclosure, may comprise a flared or tapered lower end section so as to fit to the described stent shapes.

The stent 10 depicted in FIGS. 8b and 8c has at its lower end section 2 a flared or tapered section with a radius shape; however, it is also conceivable that the flared or tapered section is not uniformly around the circumference of the stent 10. For example, the stent 10 may have a flare only near the locations of the positioning arches 15a, 15b, 15c, wherein no flare is provided near the commissure regions, i.e. the regions in between the two arms 15a', 15a'', 15b', 15b'', 15c', 15c'' of two neighboring positioning arches 15a, 15b, 15c.

As depicted in FIGS. 8b and 8c, the stent 10 according to the second stent embodiment comprises a continuous design of its lower end section 2. Due to this continuous design, in the implanted and expanded state of the stent 10, via the lower end section 2 of the stent 10 an uniform radial force is applied to the wall of the blood vessel into which the stent 10 is deployed.

If the implanted and expanded stent together with a prosthetic heart valve affixed thereto extend too far below the annulus of the heart, there may be the risk that the implanted endoprosthesis consisting of the stent 10 on the one hand and the prosthetic heart valve 100 on the other hand contacts the nerve bundles and heart block. The nerve bundles may enter at a location approximately 6 to 10 mm below the annulus of the heart.

In order to avoid the lower end section 2 of the implanted stent 10 touching the atrioventricular node, the stent 10 pursuant to the second stent embodiment is provided with an annular collar 40 which is shortened in its length by having only a single row of cells. In this regard, the total height of the stent 10 and thus the total height of the endoprosthesis 1 to be implanted into the body of the patient are reduced.

Moreover, in the programming process during which the shape of the desired (expanded) stent structure is fixed, the supporting webs 41 of the annular collar 40 may be programmed so that—when the stent 10 of the second embodiment is in its expanded state—only the upper section of the annular collar 40 extends in a radial direction outside the circumference of the stent 10, whereas the lower end section of the annular collar 40 bended relative to the upper section of the annular collar 40 in the radial direction inside the circumference of the stent 10. The lower end section of the annular collar 40 may be bent such that it extends, for example, approximately parallel to the longitudinal direction L of the stent 10. In this way, an increased contact force (radial force) is applied by the upper section of the annular collar 40 to the wall of the blood vessel into which the stent 10 is deployed, whereas the risk is reduced that the lower end section of the annular collar 40 can touch the atrioventricular node.

It is important to note, that the stent 10 according to the second stent embodiment comprises a number of notches 12e uniformly distributed around the lower end section of the annular collar 40. These notches 12e can be used for fixing a heart valve prosthesis (not shown in FIGS. 8b and 8c) to the stent 10, which may reduce the risk of an axial displacement of the heart valve prosthesis 100 relative to the stent 10. Since a plurality of notches 12e are used as additional fastening means it is possible to utilize the lower end sections of every supporting web 41 of the annular collar 40 for additionally fastening a heart valve prosthesis to the stent 10. This appears directly from the flat roll-out view pursuant to FIG. 8a.

A comparison with, for example, the flat roll-out view pursuant to FIG. 5a (first stent embodiment) illustrates directly that the provision of eyelets 12f at the lower end sections of every supporting web 41 of the annular collar 40 requires much more material for each eyelet 12f compared with the amount of material which is necessary for forming respective notches 12e. Since it is conceivable for the stent 10 to exhibit a structure integrally cut from a portion of tube, in particular from a metal tube, which incorporates all structural components of the stent 10, in particular the positioning arches 15a, 15b, 15c, the retaining arches 16a, 16b, 16c and the annular collar 40 with defined additional fastening means at the lower end thereof, an elaborate cutting pattern for forming the design of the stent 10 from the original tube portion is important. In particular, it must be taken into account that the structure of the stent 10 with all structural stent components must be cut from the limited lateral area of the original tube portion.

Hence, by providing notches 12e instead of eyelets 12f as additional fastening means at the lower end section of the annular collar 40, a greater number of notches 12e compared with the number of eyelets 12f can be generated. In detail, according to the second stent embodiment, the lower end sections of every supporting web 41 of the annular collar 40 is provided with a corresponding notch 12e acting as additional fastening means. In contrast, in the first embodiment of the stent (FIGS. 5a to 5e) only the lower end sections of every second supporting web 41 of the annular collar 40 can be provided with a corresponding eyelet 12f acting as additional fastening means.

In this regard, the stent design according to the second stent embodiment differs from the first stent design in that at the lower end section of every supporting web 41 of the annular collar 40 an additional fastening means is provided. This is due to the fact that, in the second embodiment of the stent 10, notches 12e are used as additional fastening means.

Hence, in the second stent embodiment, the additional fastening means to be used for fixing a heart valve prosthesis to the stent 10 are more uniformly distributed around the lower end section of the annular collar 40, thereby providing a more uniform fixation of a prosthetic heart valve to the stent. Hence, the risk of an axial displacement of the heart valve prosthesis relative to the stent may be further reduced. Each individual notch 12e provided at the lower end section of the annular collar 40 thereby serves to guide a thread or thin wire with which the tissue component(s) of the prosthetic heart valve is affixed or sewn to the lower end section of the annular collar 40 of the stent 10. In detail, the means (thread or thin wire) provided for fastening the tissue component(s) of the prosthetic heart valve 100 to the lower end section of the annular collar 40 is guided by way of the notches 12e so that a longitudinal displacement of the prosthetic heart valve relative to the stent 10 is substantially minimized. This also allows positioning of the prosthetic heart valve relative the stent 10. To this end, as can be seen in FIG. 1, the prosthetic heart valve 100 may further comprise an essentially zig-zag shaped pattern at a lower end section.

Moreover, by using corresponding notches 12e for the secure and defined fixing of the tissue component(s) of the prosthetic heart valve to the lower end section of the annular collar 40 of the stent 10, the means (threads or thin wires) used to fasten the tissue component(s) to the stent 10 are effectively prevented from being squeezed and thus degraded when the stent 10 with the prosthetic heart valve affixed thereto, i.e. the endoprosthesis 1, is compressed and brought into its collapsed shape such as to be ready for being inserted into a catheter system which is used for implanting the endoprosthesis 1. In this regard, the risk of structural deterioration in the threads or thin wires used to fasten the tissue component(s) of the prosthetic heart valve 100 to the stent 10 is reduced.

The cross-sectional shape of the notches 12e may be adapted to the cross-sectional shape of the thread or thin wire used to fasten the tissue component(s) of the prosthetic heart valve 100. This allows fixing of the tissue component(s) of the prosthetic heart valve 100 to the stent 10 at a precise predefined position relative to the stent 10. Because the fastening holes 12 are adapted to the thickness and/or the cross-sectional shape of the thread or thin wire used to affix the prosthetic heart valve 100 to the stent 10, relative movement between the stent 10 and the tissue component(s) of the prosthetic heart valve 100 due to the peristaltic motion of the heart can be effectively prevented when the endoprosthesis 1 is implanted. In the fully expanded and implanted state of the endoprosthesis 1, the tissue component(s) of the prosthetic heart valve 100 is/are thus fastened to the stent 10 with minimal play, based on which friction-induced wear of the thread or thin wire used to affix the prosthetic heart valve is minimized. As shown in, for example, in FIG. 8a, the notches 12e have a semi-circular cross-sectional shape.

As can be seen, in particular from FIGS. 8b to 8d, the stent 10 according to the second stent embodiment of the invention may further comprise at least one radial arch 32a, 32b, 32c which enables a particularly secure anchoring of the stent 10 in the site of implantation in the heart and which is substantially circumferentially aligned with at least one of the plurality of positioning arches 15a, 15b, 15c. In addition to its radial arches 32a, 32b, 32c, the stent 10 is further provided with a total of three leaflet guard arches 50a, 50b, 50c, each comprising two leaflet guard arms. It can be seen from the flat roll-out view shown in FIG. 8a that, in the structure of the stent according to the second stent embodiment, a leaflet guard arch 50a, 50b, 50c is provided in between each positioning arch 15a, 15b, 15c. Hence, in the stent according to the second stent embodiment, a leaflet guard arch 50a, 50b, 50c is allocated to each positioning arch 15a, 15b, 15c.

Referring to the flat roll-out view shown in FIG. 8a, the radial arches 32a, 32b, 32c of the stent 10 according to the second stent embodiment extend from the leaflet guard arches 50a, 50b, 50c towards the upper end 3 of the stent 10. As is shown most clearly in FIG. 8a, the stent 10 has three radial arches 32a, 32b, 32c, with each arch 32a, 32b, 32c located between the two arms of each leaflet guard arch 50a, 50b, 50c. Each radial arch 32a, 32b, 32c has a shape that is roughly inverse to each positioning arch 15a, 15b, 15c and extends in the opposite direction to each one of the positioning arches 15a, 15b, 15c.

On the other hand, each leaflet guard arch 50a, 50b, 50c has a substantially U-shaped or V-shaped structure which is closed to the lower end 2 of stent. Again, each leaflet guard arch 50a, 50b, 50c has a shape that is roughly similar to the shape of the positioning arch 15a, 15b, 15c in between the corresponding leaflet guard arch 50a, 50b, 50c is arranged. Furthermore, each leaflet guard arch 50a, 50b, 50c extends in the same direction as the positioning arch 15a, 15b, 15c.

In the stent design of the second stent embodiment, each arm of a leaflet guard arch 50a, 50b, 50c merges at about the mid-point of the length of an arm of a radial arch 32a, 32b, 32c into the arm of an opposing radial arch 32a, 32b, 32c. According to the stent design of the second stent embodiment, the leaflet guard arches 50a, 50b, 50c project in the longitudinal direction L of the stent and have a reduced length such that the positioning arches 15a, 15b, 15c can deploy during the expansion of the stent 10 and the leaflet guard arches 50a, 50b, 50c do not interfere during deployment.

The positioning arches 15a, 15b, 15c disposed on the stent 10 and also the retaining arches 16a, 16b, 16c may be curved in convex and arched fashion in the direction to the lower end section of the stent; i.e. toward the lower end 2 of the stent, whereby such a rounded form may reduce injuries to the artery as well as facilitate the unfolding during the self-expansion. Such a design may enable an easier insertion of the positioning arches 15a, 15b, 15c into the pockets of the native cardiac valve without correspondingly injuring the neighbouring tissue or blood vessels.

Although not explicitly illustrated in the flat roll-out view according to FIG. 8a, in the programming process during which the shape of the desired (expanded) stent structure is fixed, the leaflet guard arches 50a, 50b, 50c are preferably programmed so that they extend in a radial direction outside the circumference of the stent 10 when the stent 10 of the second stent embodiment is in its expanded state. In this way, an increased contact force can be applied to the leaflets of the native (diseased) cardiac valve when the stent of the second stent embodiment is in its expanded and implanted state. This, in turn, allows an increased security in the fixing of the stent in situ.

When the stent is in its expanded and implanted state, the leaflet guard arches 50a, 50b, 50c actively keep the diseased leaflets, i.e. the leaflets of the native cardiac valve, from impinging the leaflet tissue of the prosthetic heart valve 100 attached to the stent 10, when the positioning arches 15a, 15b, 15c are placed outside the native leaflets. In addition, the leaflet guard arches 50a, 50b, 50c may also provide additional anchoring and securing against migration. This feature may be unique compared to the cage known from the prior art stent designs which are not provided with positioning arches to push the diseased leaflets out of the way.

As can be seen from the roll-out view depicted in FIG. 8a, according to the stent design of the second stent embodiment, the two arms 32', 32" of each radial arch 32a, 32b, 32c are connected together at the upper end 3 of the stent 10 by means of a radiused connecting portion or head. This head is not only radiused but also widens at the tip so that the head abuts against the interior wall of the vessel over as large a contact area as possible when the stent 10 is in its expanded and implanted state. The heads of each radial arch 32a, 32b, 32c may also serve as additional means by which the stent 10 may be retained in a catheter before and during implantation and/or to recapture the stent after implantation.

In the programming process during which the shape of the desired (expanded) stent structure is fixed, the radial arches 32a, 32b, 32c are programmed so that they extend in a radial direction outside the circumference of the stent 10 when the stent 10 is in its expanded state. In this way an increased contact force can be applied to the vessel wall by the upper end region of the stent 10. This, in turn, allows an increased security in the fixing of the stent 10 in situ, thereby reducing the likelihood of migration of the stent 10. Therefore, in its expanded state, in addition to the clamping effect of the positioning arches 15a, 15b, 15c and in addition to the additional anchoring obtainable by the leaflet guard arches 50a, 50b, 50c, the stent 10 of the second stent embodiment is secured in place on implantation via radial forces exerted by the retaining arches 16a, 16b, 16c, the auxiliary arches 18a, 18b, 18c, the radial arches 32a, 32b, 32c, and the annular collar 40, all of which project outwards in a radial direction from the circumference of the stent 10.

It can be seen from the flat roll-out view shown in FIG. 8a that the radial arches 32a, 32b, 32c do not project in the longitudinal direction L of the stent 10 beyond the plane in which the catheter retaining means 23 or the fastening means with fastening eyelets 24 are situated. This may ensure that the catheter retaining means 23 can co-operate with corresponding means within a suitable implantation catheter without interference from the heads of the radial arches 32a, 32b, 32c. Indeed, as explained above, the heads themselves can be used as additional catheter retaining means or additional means to effect explanation of the stent 10.

In principle, the stent 10 may have more than three radial arches 32 in order to increase the radial contact force further. It is also possible to provide barb elements on all or some of the radial arches 32a, 32b, 32c, for example, to allow a still better anchoring of the stent 10 at the implantation site.

Moreover, with respect to fixing the upper area 3 of stent 10 to the wall of the blood vessel into which the stent 10 is deployed, it would be conceivable for the stent 10 to comprise barb members arranged, for example, on the eyelets 24, the tips of the barbs pointing toward the lower end 2 of stent 10.

In addition, a liner or sheath, typically a fabric, polymeric or pericardial sheet, membrane, or the like, may be provided over at least a portion of the exterior of the stent 10 to cover all or most of the surface of the outside of the stent 10, extending from a location near the lower end section of the stent to a location near the upper end section of the stent. The liner may be attached to the stent 10 at at least one end, as well as at a plurality of locations between said ends thereby forming an exterior coverage. Such exterior coverage provides a circumferential seal against the inner wall of the blood vessel lumen in order to inhibit leakage of blood flow between the stent 10 and the luminal wall thereby and to prevent a blood flow bypassing the endoprosthesis 1.

For example, the liner may be stitched or otherwise secured to the stent 10 along a plurality of circumferentially spaced-apart axial lines. Such attachment permits the liner to fold along a plurality of axial fold lines when the stent 10 is radially compressed. The liner will further be able to open and conform to the luminal wall of the tubular frame as the frame expands. Alternatively, the liner may heat welded, or ultrasonically welded to the stent 10. The liner may be secured to the plurality of independent arches (positioning arches 15a, 15b, 15c, retaining arches 16a, 16b, 16c, auxiliary arches 18a, 18b, 18c, leaflet guard arches 50a, 50b, 50c) preferably along axial lines. In addition, the liner may be secured to the annular collar 40 provided at the lower end section 2 of the stent 10. The liner will preferably be circumferentially sealed against the stent 10 at at least one end.

By covering at least a part of the outside surface of the stent 10 with the liner or sheath, thrombogenicity of the endoprosthesis 1 resulting from exposed stent elements is greatly reduced or eliminated. Such reduction of thrombogenicity is achieved while maintaining the benefits of having a stent structure which is used for spreading up a prosthetic heart valve 100 and for anchoring the prosthetic heart valve 100 in place.

As already mentioned, the stent 10 can be compressed from a relaxed, large diameter configuration to a small diameter configuration to facilitate introduction. It is necessary, of course, that the outer liner remain attached to the stent 10 both in its radially compressed configuration and in its expanded, relaxed configuration.

The liner is composed of pericardial material or conventional biological graft materials, such as polyesters, polytetrafluoroethylenes (PTFE's), polyurethanes, and the like, usually being in the form of woven fabrics, non-woven fabrics, polymeric sheets, membranes, and the like. A presently preferred fabric liner material is a plain woven polyester, such as Dacron® yarn (Dupont, Wilmington, Del.).

A third embodiment of the stent 10 according to the present invention is described in the following with reference to FIG. 9 which is a flat roll-out view of this embodiment, whereby the cardiac valve stent 10 is shown in its expanded state.

The third embodiment of the stent 10 is similar in structure and function with respect to the second embodiment. To avoid repetition, reference is therefore made to the above description of the second embodiment. In particular, the lower end section of the stent 10 is constituted by an annular collar 40 which is likewise provided with notches 12e acting as additional fastening means.

In addition, the stent 10 according to the third stent embodiment is provided with retaining arches 16a, 16b, 16c whose arms 16a', 16a", 16b', 16b", 16c', 16c" are segmented by a plurality of bending edges 33 which are not only used for defining a bending point of two neighboring arm segments, but also as fastening notches which can be used for fixing a heart valve prosthesis 100 to the stent 10. In turn, the retaining arches 16a, 16b, 16c of the third stent embodiment are adapted to extend along the bendable transition area 104 of the prosthetic heart valve, when the endoprosthesis is assembled.

The third embodiment of the stent 10 also includes radial arches 32a, 32b, 32c extending from the positioning arches 15a, 15b, 15c towards the upper end 3 of the stent 10. As is shown in the FIG. 9, the stent 10 has three radial arches 32a, 32b, 32c, with each arch 32a, 32b, 32c located between the two arms 15a, 15a', 15b, 15b', 15c, 15c' of each positioning arch 15a, 15b, 15c. Each radial arch 32a, 32b, 32c has a shape that is roughly inverse to each positioning arch 15a, 15b, 15c and extends in the opposite direction to each one of the positioning arches 15a, 15b, 15c.

Contrary to the stent design of the second stent embodiment, however, the stent design of the third embodiment is not provided with leaflet guard arches 50a, 50b, 50c. Furthermore, each arm of a radial arch 32a, 32b, 32c merges at about the mid-point of the length of the stent 10 into an arm 15a', 15a", 15b', 15b", 15c', 15c" of an opposing positioning arch 15a, 15b, 15c.

A fourth embodiment of the stent 10 according to the present invention is described in the following with reference to FIG. 10. In detail, FIG. 10 is a flat roll-out view of the fourth stent embodiment, whereby the cardiac valve stent 10 is shown in its expanded state.

From a comparison of FIG. 10 with FIG. 8*d* it is derivable that the fourth embodiment of the stent 10 is similar in structure and function with respect to the second embodiment. To avoid repetition, reference is therefore made to the above description of the second embodiment.

The fourth embodiment of the stent 10 only differs from the second stent embodiment in that the respective lower end sections of the leaflet guard arches 50*a*, 50*b*, 50*c* are removed. In particular, the lower end sections of the leaflet guard arches 50*a*, 50*b*, 50*c* between the points where each arm of a radial arch 32*a*, 32*b*, 32*c* merges is removed.

Figure 11C:
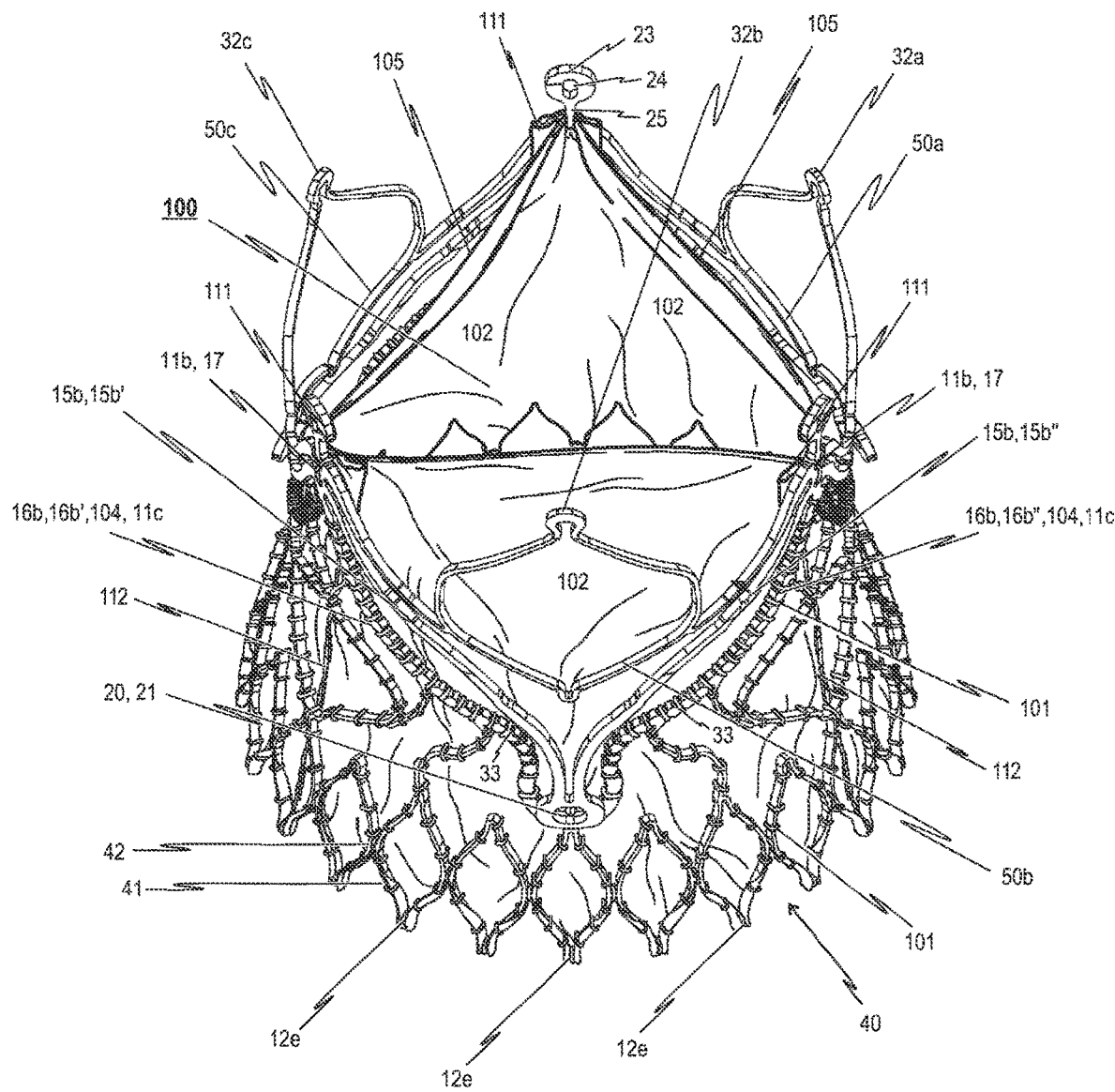
FIG. 11c a perspective top view of the endoprosthesis depicted in FIG. 11a, where the endoprosthesis is shown in an expanded state and where the endoprosthesis comprises a cardiac valve stent and a prosthetic heart valve according to an exemplary embodiment of the disclosure, said cardiac valve stent is used for holding the prosthetic heart valve.

Another embodiment of an endoprosthesis 1 according to the present disclosure is shown by FIGS. 11*a* to 11*c*. In detail, this third embodiment of an endoprosthesis 1 includes a stent 10 according to the second stent embodiment (FIGS. 8*a* to 8*d*) and a prosthetic heart valve 100, in accordance with the second heart valve embodiment (FIGS. 3 and 4), affixed thereto.

In particular, FIG. 11*a* shows a first side view of the third embodiment of the endoprosthesis 1. From this first side view, the characteristic U-shape of the retaining arches 16*a*, 16*b*, 16*c* becomes readily apparent.

As indicated hereinbefore, this U-shape of the respective arms 16*a'*, 16*a"*, 16*b'*, 16*b"*, 16*c'*, 16*c"* of the retaining arches 16*a*, 16*b*, 16*c* is achieved by segmenting the arms 16*a'*, 16*a"*, 16*b'*, 16*b"*, 16*c'*, 16*c"*. In detail, the arms 16*a'*, 16*a"*, 16*b'*, 16*b"*, 16*c'*, 16*c"* are segmented by providing a plurality of bending edges 33. In the depicted expanded state of the stent 10, two neighboring arm segments are angled relative to each other, wherein the bending point of these two neighboring arm segments is defined by the bending edge 33 which is provided in between the both neighboring arm segments. Hence, the greater the number of bending edges 33 provided in an arm 16*a'*, 16*a"*, 16*b'*, 16*b"*, 16*c'*, 16*c"* of a retaining arch 16*a*, 16*b*, 16*c*, the greater the number of arm segments which may extend in different directions in the expanded state of the stent 10. In this respect, the shape of the respective arms 16*a'*, 16*a"*, 16*b'*, 16*b"*, 16*c'*, 16*c"* of the retaining arches 16*a*, 16*b*, 16*c* can be adapted to the shape of transition area 104 of a prosthetic heart valve 100 to be affixed to the stent 10 adapted so as to fit the retaining arches 16*a*, 16*b*, 16*c* to the progression of the bendable transition area 104 of the prosthetic heart valve 100.

Further to this, FIG. 11*a* shows the bending edges providing a number of fastening notches which are used to fix the bendable transition area 104 to stent 10. Thus, in this third endoprosthesis embodiment, there are no additional fastening holes 12*a* needed along the respective arms 16*a'*, 16*a"*, 16*b'*, 16*b"*, 16*c'*, 16*c"* of the retaining arches 16*a*, 16*b*, 16*c*. Rather, the sutures 101 are wrapped around the retaining arches 16*a*, 16*b*, 16*c* and sewn to the bendable transition area 104, whilst being held in place by the fastening notches which extend essentially in the same direction as the bendable transition area 104 of the prosthetic heart valve. That is, the prosthetic heart valve 100 of the present third embodiment of the endoprosthesis 1 is more securely attached to the stent 10 as the fastening notches provide a greater number of attachment points compared with the number of fastening holes 12*a*, used in the embodiment according to FIGS. 6*a* and 6*b* of the present disclosure. In this regard, high stress concentrations at each single attachment point can be effectively avoided.

Another feature which has already been described with reference to the second embodiment of the endoprosthesis 1 depicted by FIGS. 7*a* and 7*b*, is the provision of leaflet guard arches 50*a*, 50*b*, 50*c*. To avoid repetition, reference is therefore made to the above description of the second endoprosthesis embodiment depicted by FIGS. 7*a* and 7*b*.

FIG. 11*b* shows the connection between the skirt portion 103 and the aforementioned plurality of lattice cells 70. This plurality of lattice cells 70 formed by a plurality of struts in the area between the arms 16*a'*, 16*a"*, 16*b'*, 16*b"*, 16*c'*, 16*c"* of two neighbouring (adjacent) retaining arches 16*a*, 16*b*, 16*c*, provides for an additional support for the bendable transition area 104 of a prosthetic heart valve 100 to be attached to the stent 10. As depicted by FIG. 11*b*, the prosthetic heart valve 100 may be directly sewn to the lattice cells 70 by means of sutures 101, threads or thin wires.

As can further be derived from FIG. 11*b*, the prosthetic heart valve 100 according to the third embodiment of the endoprosthesis 1, comprises three separate pieces 120 being sewn together at their contiguous edges 112. FIG. 11*c* shows a perspective top view of the third embodiment of the endoprosthesis. In detail, FIG. 11*c* illustrates the attachment of the three separate pieces 120 being sewn together in a cylindrical manner along their contiguous edges 112. After the contiguous edges 112 of the separate pieces 120 are aligned and sewn together, the sleeves 111 of the separate pieces 120 are turned to the outside and attached to the commissural attachment region 11*b* of the stent 10. A more detailed description of this particular attachment method will be described with reference to FIGS. 19*a-c* and 20.

It should be noted that this third endoprosthesis embodiment is not meant to be restrictive. Of course, it is also conceivable to attach a one piece prosthetic heart valve, in accordance with the first valve embodiment (FIG. 1) of the present disclosure, to the stent 10 shown in FIGS. 8*a* to 8*d*.

In the figures of this specification, the prosthetic heart valve 100 is generally mounted to the inner surface of the stent 10. Of course, it is also conceivable to mount the prosthetic heart valve 100 to the outer surface of a support stent 10. That is, the skirt portion 102 could be in direct contact with the diseased native heart valve and could be attached to the stent 10 by means of sutures. Mounting the prosthetic heart valve 100 to the outer surface of the stent 10 supports the load transfer from the leaflet 102 to the stent 10 and reduces the stress concentration near the attachment regions 11*b*, 11*c*. This greatly reduces stresses on the leaflets 102 during closing and consequently improves the durability thereof. Also, it is possible to design the valve to obtain improved hemodynamics in the case of mounting the skirt portion to the outer surface of the stent. Additionally, the heart valve material which is in direct contact with the diseased native heart valve provides a good interface for sealing against leakage (i.e., paravalvular leakage), tissue in-growth and attachment.

Figure 3:
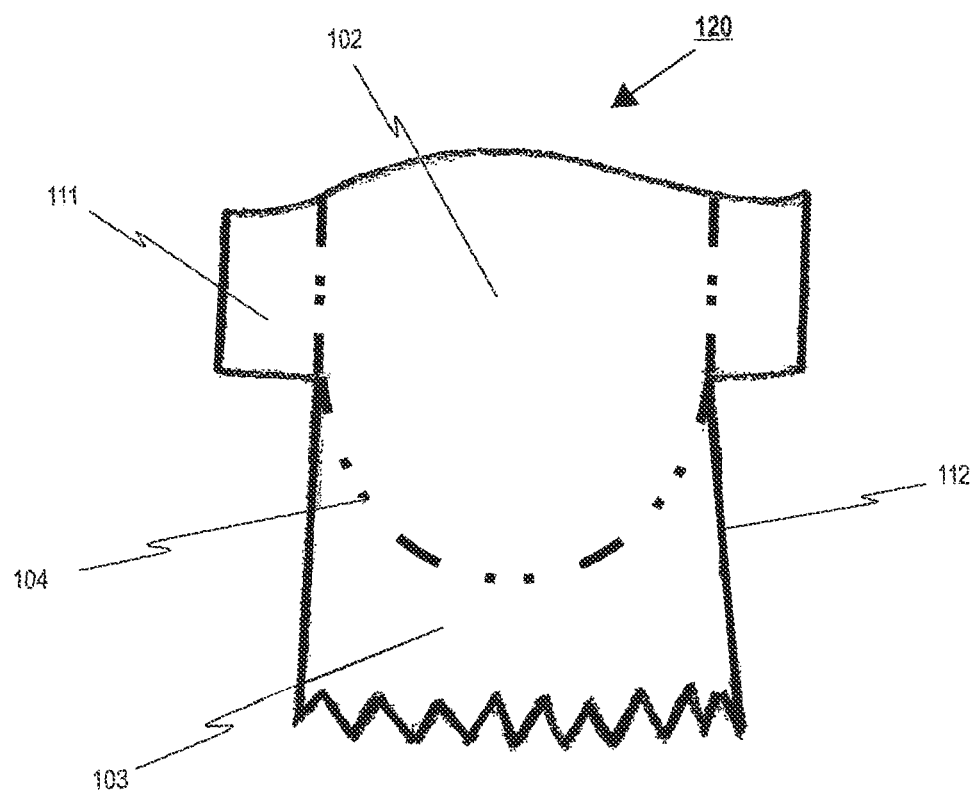
FIG. 3 a flat pattern of a prosthetic heart valve material piece having an essentially t-shirt like shape for a prosthetic heart valve according to a further exemplary embodiment of the disclosure.
Figure 4:
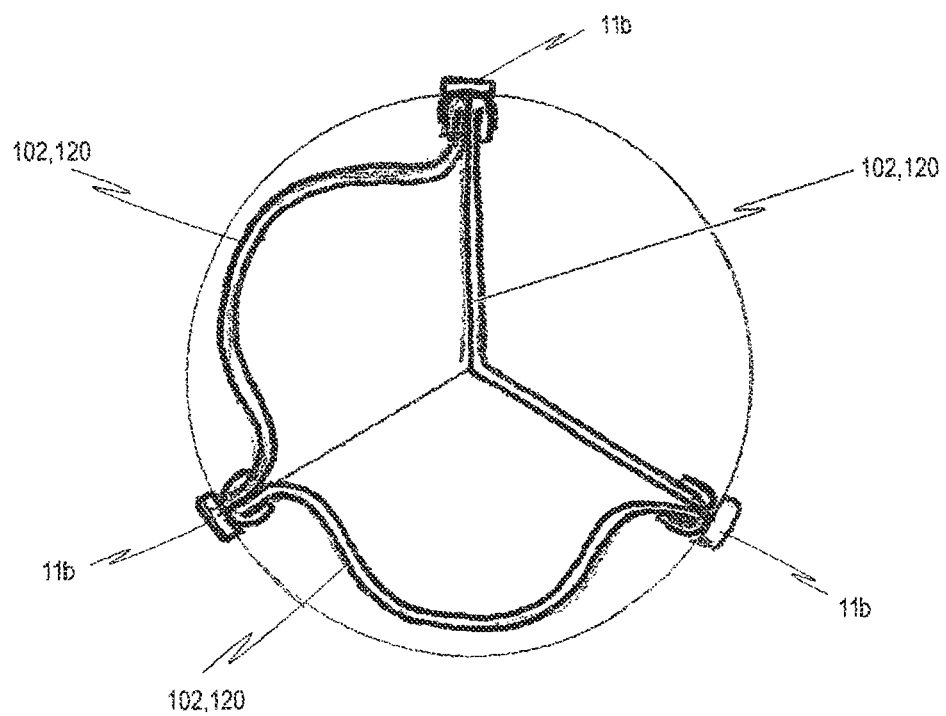
FIG. 4 a top view of the three prosthetic heart valve material pieces sewn together and attached to commissure attachment regions of a stent according to the further exemplary embodiment of the disclosure.

An alternative second embodiment of a prosthetic heart valve 100 is shown in FIGS. 3 and 4 as well as FIGS. 19*a-c* and 20.

In particular, FIGS. 3 and 4 illustrate a flat pattern of the prosthetic heart valve material, which has an essentially t-shirt like shape. According to this realisation, the prosthetic heart valve 100 is made of three separate pieces 120 exhibiting the depicted t-shirt like shape. The three separate pieces 120 are connected to each other at their contiguous edges 112 by suturing, in order to form the cylindrical or conical shape of the prosthetic heart valve 100. The three separate pieces 120 may be cut from more than one pericardial sack, so as to obtain three pieces 120 having matching characteristics, e.g., tissue thickness and properties. In addition, the bendable transition area 104 is implied in the drawing of FIG. 3. That is, that each of the separate pieces 120 is intended to represent one of the three leaflets 102 of the prosthetic heart valve 100, in addition to the transition area 104 and skirt portion 103. FIG. 4 shows a top view of the three separate pieces 120 sewn together and attached to a commissure attachment regions 11*b* of a stent according to the further exemplary embodiment of the disclosure.

Figure 19A:
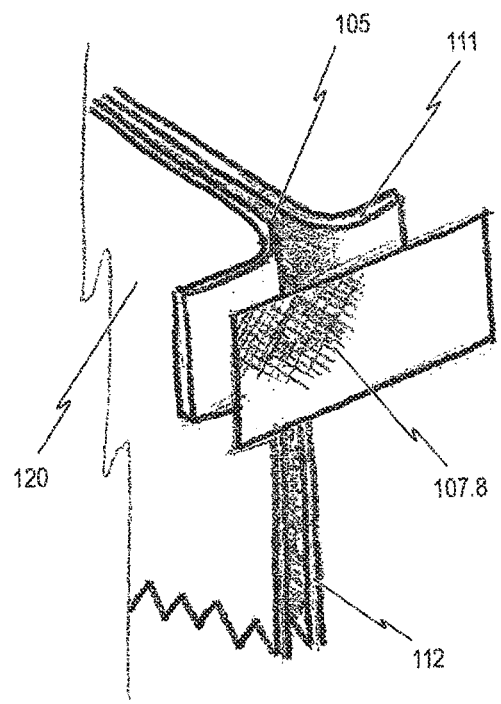
FIG. 19a-c the steps for connecting two separate prosthetic heart valve material pieces along their contiguous edges according to the second exemplary embodiment of the prosthetic heart valve.
Figure 19B:
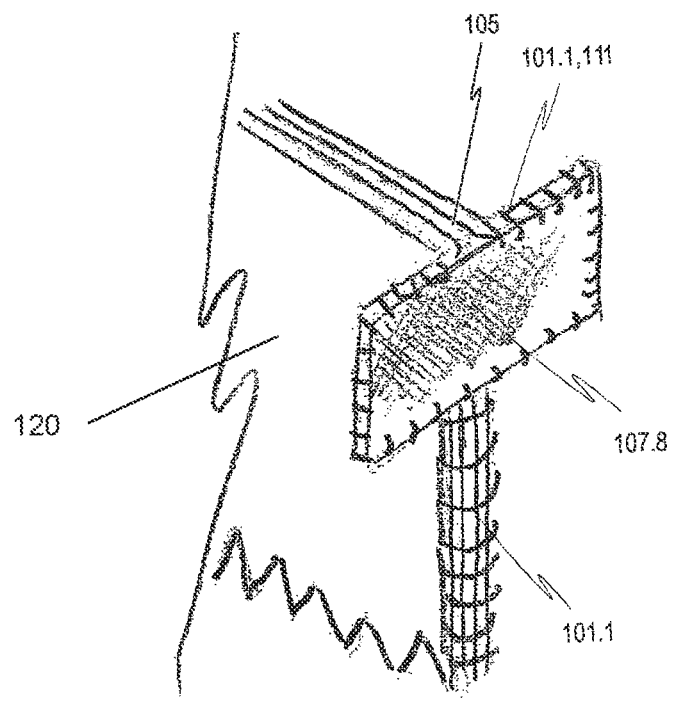
Figure 19C:
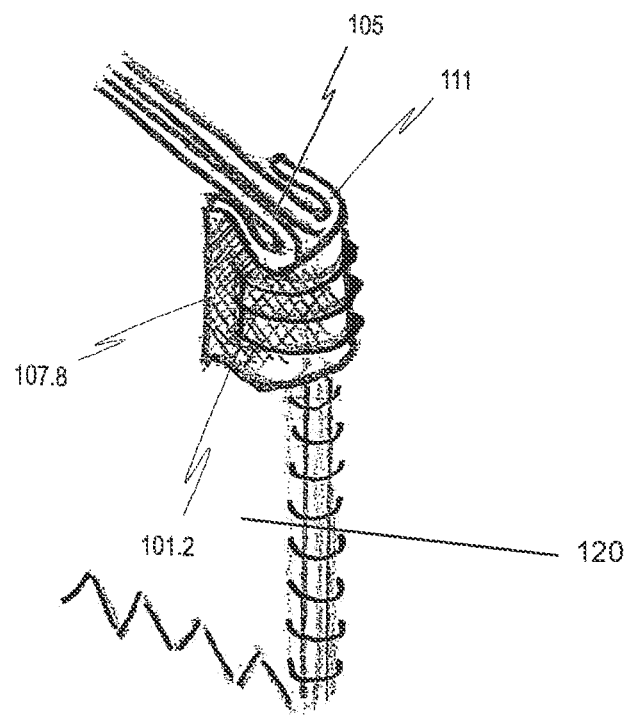

The steps for the connection of two of the three separate pieces 120 on their contiguous edges 112 are depicted in FIGS. 19*a-c*.

In a first step, the contiguous edges 112 are brought together and sleeves 111 of the separate pieces 120 are turned to the outside, as shown in FIG. 19*a*.

A reinforcement element 107.8 may then be attached to the front surface of the sleeves 111 by means of sutures 101.1, preferably applying a blanket stitch. At the same time, the continuous edges 112 are sewn together by means of the same sutures 101.1, again preferably applying a blanket stitch.

In a third step, the reinforced sleeves 111 are turned even further to the outside, so that they end up being folded rearwards onto the surface of the leaflets 102. This rearward folded position is then secured by means of lateral sutures 101.2 stitched on the outer surface of the reinforcement element 107.8.

A top view of the three separate pieces 120 sewn together and attached to the commissure attachment regions 11*b* of a stent 10 is illustrated in FIG. 4. As mentioned before, each of the three separated pieces 120 represents one of the three leaflets 102 of the prosthetic heart valve 100.

Figure 20:
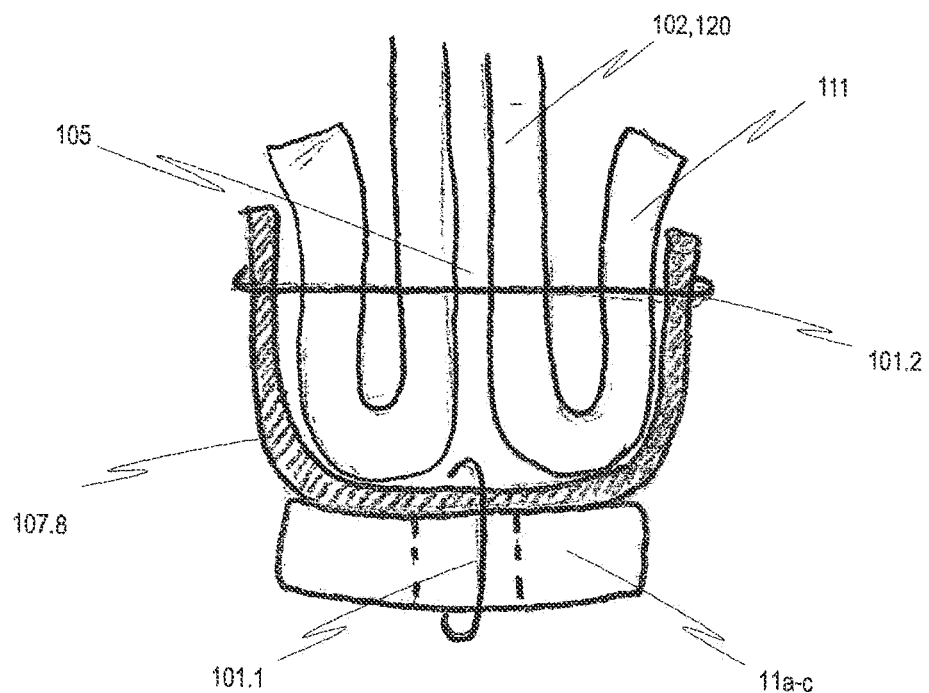
FIG. 20 a top view of the attachment of the prosthetic heart valve to the commissure attachment regions of a stent according to the second exemplary embodiment of the prosthetic heart valve.

A detailed perspective view of the attachment of the prosthetic heart valve 100 to the commissure attachment regions 11*b* of the present embodiment is shown in FIG. 20. The reinforcement element 107.8 is wrapped around the rearward folded sleeves 111. This rearward folded position is held by the lateral suture 101.2 connecting the opposite ends of the reinforcement element 107.8. The material of the reinforcement element 107.8 preferably has much higher suturing retention strength than the heart valve material of the three separate pieces 120.

For this reason, the reinforcement element 107.8 is used to attach the prosthetic heart valve 100 to the commissure attachment regions 11*b* of the stent 10, by means of suturing 101.1. Thus, stresses due to the suturing 101.1 between the stent 10 and the prosthetic heart valve 100 are mainly introduced into the material of the reinforcement element 107.8, avoiding high stress concentrations in the prosthetic heart valve 100. Additionally, the intent of this design is to limit the leaflet travel during the opening phase by pinching the commissure area to prevent the leaflets 102 from hitting the stent 10. Also, this assembly method displaces the valve commissures inward radially from the stent post to further limit the leaflets from hitting the stent.

Figure 21:
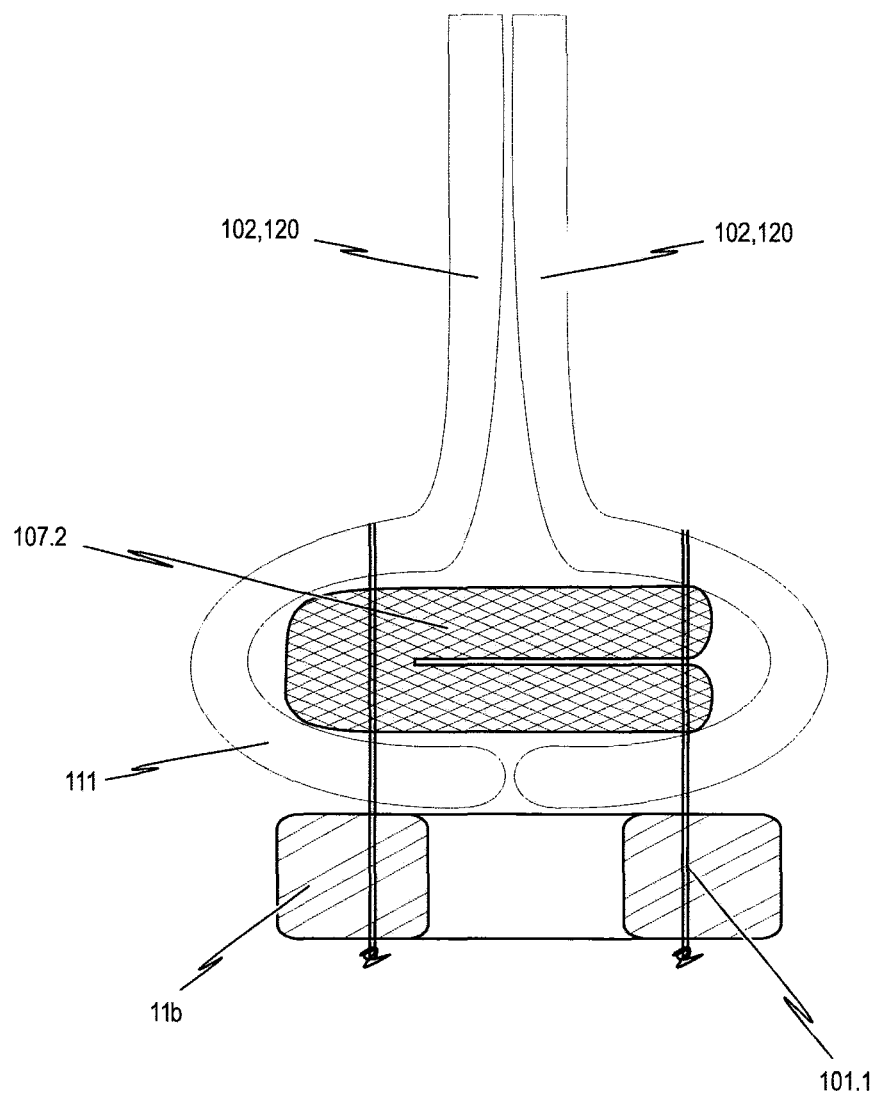
FIG. 21 a detailed perspective view of an alternative attachment of the prosthetic heart valve to the commissure attachment regions of a stent according to the second exemplary embodiment of the prosthetic heart valve.

FIG. 21 illustrates an alternative way of attachment of the prosthetic heart valve 100 according to FIGS. 3 and 4 of the present disclosure. In detail, the sleeves 111 of adjacent separate pieces 120 are formed to enclose an inner cushion 107.2. Therefore, in turn, the leaflets 102 are displaced from the commissure attachment region 11*b* to limit the leaflets 102 form hitting the stent. Furthermore, the sutures 101.1 extending through the sleeves 111 and the inner cushion 107.2 are more hidden and the edges of the sleeves 111 are tucked under the inner cushion 107.2. Therefore, in this embodiment, the wear of the prosthetic heart valve 100, is significantly reduced as the leaflets 102 of the prosthetic heart valve are not in direct contact with knots of the sutures 101.1 or the edges of the sleeves 111 respectively. Of course, it is generally advantageous for any of the described embodiments, to avoid direct contact between the knots of the sutures 101 and the prosthetic heart valve material by means of reinforcement elements 107.1-107.8, in order to reduce wear.

The above disclosure is intended to be illustrative and not exhaustive. This description will suggest many variations and alternatives to one of ordinary skill in this art. All these alternatives and variations are intended to be included within the scope of the claims where the term "comprising" means "including, but not limited to". Those familiar with the art may recognize other equivalents to the specific embodiments described herein which equivalents are also intended to be encompassed by the claims.

Further, the particular features presented in the dependent claims can be combined with each other in other manners within the scope of the disclosure such that the disclosure should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g. each claim depending directly from claim 1 should be alternatively taken as depending from all previous claims). In jurisdictions where multiple dependent claim formats are restricted, the following dependent claims should each be also taken as alternatively written in each singly dependent claim format which creates a dependency from a prior antecedent-possessing claim other than the specific claim listed in such dependent claim below.

LIST OF REFERENCE NUMERALS 1 endoprosthesis
2 lower end of the stent/endoprosthesis
3 upper end of the stent/endoprosthesis
10 cardiac valve stent/stent
11*b* commissure attachment region of the stent
11*c* lower leaflet attachment region of the stent
12*a*, 12*c* additional fastening holes
12*b* auxiliary fastening holes
15*a*-15*c* positioning arches
15*a*'-15*a*" arms of the first positioning arch
15*b*'-15*b*" arms of the second positioning arch
15*c*'-15*c*" arms of the third positioning arch
16*a*-16*c* retaining arches
16*a*'-16*a*" arms of the first retaining arch
16*b*'-16*b*" arms of the second retaining arch
16*c*'-16*c*" arms of the third retaining arch
17 first connecting web
17*d* upper end of the first connecting web
17*p* lower end of the first connecting web
20 head portion of the positioning arch
21 reference marker
22 connecting portion between the arms of neighbouring positioning arches
23 catheter retaining means
24 eyelet
25 second connecting web
30 head portion/connecting portion of the retaining arch
32*a*-32*c* radial arches
33 bending edges in the arms of the retaining arches 40 annular collar
41 supporting web
42 transversal web
50a-50c leaflet guard arches
70 structure of lattice cells
100 prosthetic heart valve
101 thread
101.1 suture
101.2 lateral suture
101.3 surrounding suture
101.4 clinging suture
102 leaflet of the prosthetic heart valve
103 skirt portion
104 transition area
105 commissures
106 fastening holes
107.1-107.8 reinforcement element
108 round edge
109 cavity
110 slot
111 sleeves
112 contiguous edges
120 separate piece of prosthetic heart valve
L longitudinal direction of the stent

The invention claimed is:

1. A prosthetic heart valve assembly comprising:
at least two pieces of tissue comprising:
a distal portion including a leaflet between a first sleeve and a second sleeve; and
a proximal portion having a width less than a width of the distal portion; and
at least two reinforcement elements;
wherein the first sleeve of each piece is coupled to the second sleeve of an adjacent piece to form a commissure of the prosthetic heart valve assembly, and an outer surface of each commissure is covered by one of the reinforcement elements; and
wherein the proximal portion of each piece includes (1) a first side edge extending from the first sleeve to a proximal zigzag edge and (2) a second side edge extending from the second sleeve to the proximal zigzag edge, and wherein the first side edge of each piece is sutured to the second side edge of an adjacent piece.

2. The prosthetic heart valve assembly of claim 1, wherein each piece of tissue is a monolithic piece of natural tissue or synthetic tissue.

3. The prosthetic heart valve assembly of claim 1, wherein each reinforcement element of the at least two reinforcement elements is flexible and comprises a polymer.

4. The prosthetic heart valve assembly of claim 1, wherein each reinforcement element of the at least two reinforcement elements is made of polytetrafluoroethylene or polyethylene terephthalate.

5. The prosthetic heart valve assembly of claim 1, wherein each piece of tissue is a monolithic piece of pericardial tissue that includes the distal portion and the proximal portion and has a thickness ranging from 160 μm to 300 μm.

6. The prosthetic heart valve assembly of claim 1, wherein, for each commissure, end portions of the first sleeve and the second sleeve are folded away from each other.

7. The prosthetic heart valve assembly of claim 1, wherein, for each commissure, end portions of the first sleeve and the second sleeve are sutured to a perimeter of the reinforcement element.

8. The prosthetic heart valve assembly of claim 1, wherein the at least two pieces are cut from a single sheet of pericardial tissue.

9. The prosthetic heart valve assembly of claim 1, wherein the at least two pieces are cut from different sheets of pericardial tissue.

10. The prosthetic heart valve assembly of claim 1, wherein the prosthetic heart valve assembly is attached to an inner surface of an expandable stent, the at least two reinforcement elements being sutured to respective commissure posts of the stent.

11. The prosthetic heart valve assembly of claim 10, wherein each commissure post includes two holes distributed along a longitudinal axis of the commissure post.

12. The prosthetic heart valve assembly of claim 10, wherein a distal end of each commissure post includes a rounded element for attachment to a catheter, each reinforcement element being sutured to a respective commissure post at a location proximal to the rounded element.

* * * * *